(12) United States Patent
Cattaneo et al.

(10) Patent No.: US 11,137,393 B2
(45) Date of Patent: Oct. 5, 2021

(54) INTRABODIES TARGETING POST-TRANSLATIONAL MODIFICATIONS OF NATIVE PROTEINS AND METHOD FOR OBTAINING THEM

(71) Applicant: SCUOLA NORMALE SUPERIORE, Pisa (IT)

(72) Inventors: Antonino Cattaneo, Pisa (IT); Michele Chirichella, Pisa (IT)

(73) Assignee: SCUOLA NORMALE SUPERIORE, Pisa (IT)

( * ) Notice: Subject to any disclaimer, the term of this patent is extended or adjusted under 35 U.S.C. 154(b) by 0 days.

(21) Appl. No.: 15/772,941

(22) PCT Filed: Nov. 2, 2016

(86) PCT No.: PCT/EP2016/076447
§ 371 (c)(1),
(2) Date: May 2, 2018

(87) PCT Pub. No.: WO2017/076916
PCT Pub. Date: May 11, 2017

(65) Prior Publication Data
US 2019/0361013 A1 Nov. 28, 2019

(30) Foreign Application Priority Data
Nov. 2, 2015 (IT) .......................... 102015000068085

(51) Int. Cl.
| | | |
|---|---|---|
| *G01N 33/542* | (2006.01) | |
| *C07K 16/18* | (2006.01) | |
| *C07K 16/40* | (2006.01) | |
| *C12N 15/10* | (2006.01) | |
| *G01N 33/68* | (2006.01) | |

(52) U.S. Cl.
CPC .......... *G01N 33/542* (2013.01); *C07K 16/18* (2013.01); *C07K 16/40* (2013.01); *C12N 15/1055* (2013.01); *G01N 33/6845* (2013.01); *G01N 33/6857* (2013.01); *C07K 2317/21* (2013.01); *C07K 2317/33* (2013.01); *C07K 2317/565* (2013.01); *C07K 2317/569* (2013.01); *C07K 2317/622* (2013.01); *C07K 2317/81* (2013.01); *C07K 2317/82* (2013.01); *C07K 2317/92* (2013.01)

(58) Field of Classification Search
CPC ............ G01N 33/542; G01N 33/6845; G01N 33/6857; G01N 33/6854; C12N 15/1055; C12N 9/1029; C12Q 33/6845; C12Q 2565/531; C07K 16/44; C07K 16/18; C07K 16/40; C07K 2317/21; C07K 2317/33; C07K 2317/565; C07K 2317/569; C07K 2317/622; C07K 2319/70; C07K 2319/80; C07K 2319/61; C07K 2317/81; C07K 2317/82; C07K 2317/92
See application file for complete search history.

(56) References Cited

U.S. PATENT DOCUMENTS

| | | | |
|---|---|---|---|
| 4,676,980 A | 6/1987 | Segal et al. | |
| 4,954,617 A | 9/1990 | Fanger et al. | |
| 7,569,390 B1 * | 8/2009 | Eric ....................... | C07K 16/08 |
| | | | 435/328 |
| 2013/0196867 A1 | 8/2013 | Strahl et al. | |

FOREIGN PATENT DOCUMENTS

| | | |
|---|---|---|
| EP | 0239400 A2 | 9/1987 |
| WO | 90/07861 A1 | 7/1990 |
| WO | 92/01047 A1 | 1/1992 |
| WO | 95/22625 A1 | 2/1995 |
| WO | 95/11922 A1 | 5/1995 |
| WO | 96/06213 A1 | 2/1996 |
| WO | 97/08320 A1 | 3/1997 |
| WO | 97/28261 A1 | 8/1997 |
| WO | 00/54057 A1 | 9/2000 |

OTHER PUBLICATIONS

Guo et al., Nature Biothechnology 22(7): 888-892. (Year: 2004).*
Visintin et al,m J Immunol Methods 290: 135-153. (Year: 2004).*
Meli et al., J Mol Biol 387: 584-606. (Year: 2009).*
Yuko Sato, et al., Genetically Encoded System to Track Histone . . . , Scientific Reports, vol. 3, No. 2436, pp. 1-7, 2013.
Yoko Hayashi-Takanaka, et al., Tracking Epigenetic Histone Modifications in Single . . . , Nucleic Acids Research, vol. 39, No. 15, pp. 6475-6488, 2011.
Hiroshi Kimura, et al., Visualizing Posttranslational and Epigenetic . . . , Histochemistry and Cell Biology, vol. 144, No. 2, pp. 101-109, 2015.
Giovanni Meli, et al., Direct In Vivo Intracellular Selection of Conformation-Sensitive . . . , Journal of Molecular Biology, vol. 387, No. 3, pp. 584-606, 2009.
Michela Visintin, et al., In Vivo Selection of Intrabodies Specifically Targeting . . . , Journal of Biotechnology, vol. 135, No. 1, pp. 1-15, 2008.
Dawei Guo, et al., A Tethered Catalysis, Two-Hybrid System to Identify . . . , Nature Biotechnology, vol. 22, No. 7, pp. 888-892, 2004.
Michela Visintin, et al., Intracellular Antibodies for Proteomics, Journal of Immunological Methods, vol. 290, No. 1-2, pp. 135-153, 2004.
International Search Report and Written Opinion for International Application No. PCT/EP2016/076447 (12 Pages) (dated Apr. 26, 2017).

(Continued)

*Primary Examiner* — Phuong Huynh
(74) *Attorney, Agent, or Firm* — Lucas & Mercanti, LLP

(57) ABSTRACT

The present invention refers to a method for determining the ability of an immunoglobulin to bind to a post-translationally modified target in an intracellular environment, which folds and it is post-translationally modified as a native protein intracellularly. The present invention also refers to antibodies obtained by the above method and uses thereof.

Figure 1:
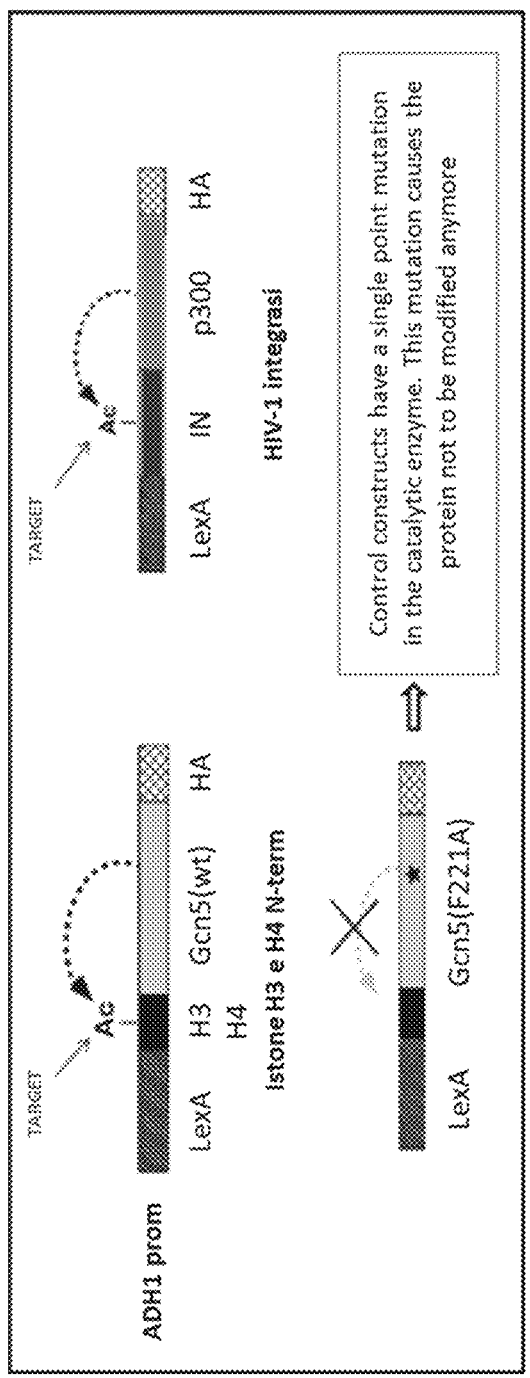

9 Claims, 28 Drawing Sheets
Specification includes a Sequence Listing.

(56) References Cited

OTHER PUBLICATIONS

Italian Search Report for corresponding IT Application No. 102015000068085 (14 pages) (dated Mar. 18, 2016).
Okamoto, T; et al. "Optimal construction of non-immune scFv phage display libraries from mouse bone marrow and spleen established to select specific scFvs efficiently binding to antigen." Biochemical and biophysical research communications vol. 323, No. 2 (2004): pp. 583-591.
Marks, Jd; et al. "PCR cloning of human immunoglobulin genes." Methods in molecular biology (Clifton, N.J.) vol. 248(2004): pp. 117-134.
European Patent Office, "Partial European Search Report," which was issued in connection with European Patent Application No. 21153091.0 and dated Aug. 10, 2021 (17 pages).

* cited by examiner

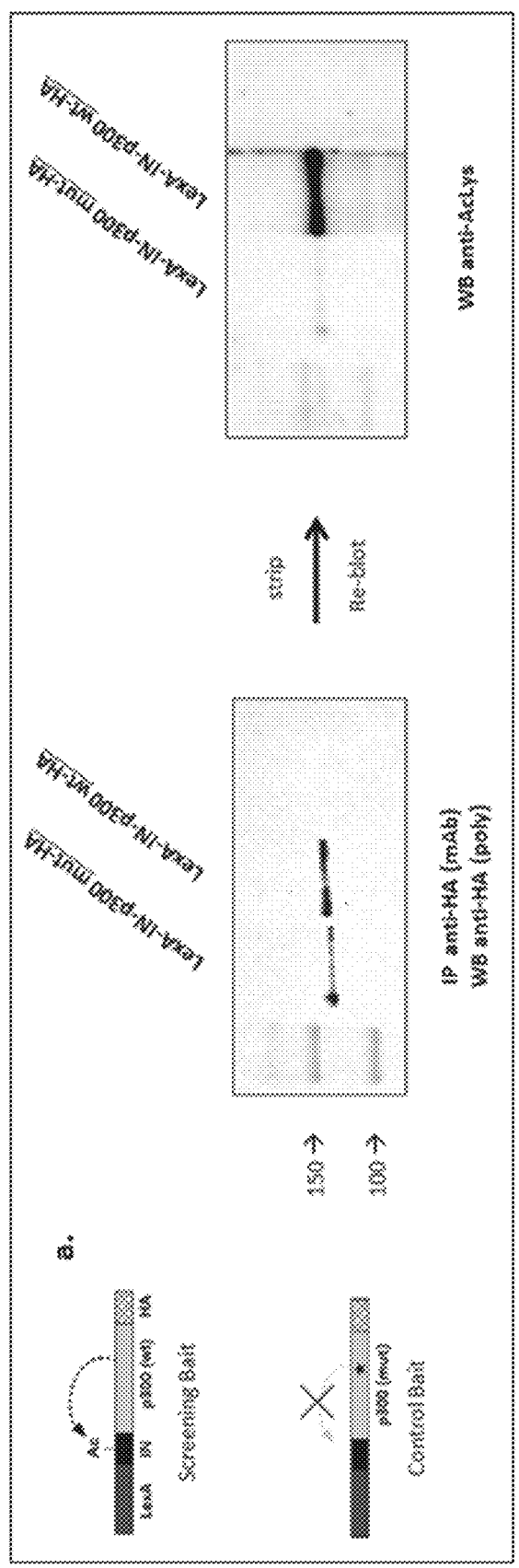
Fig. 2 (1/3)

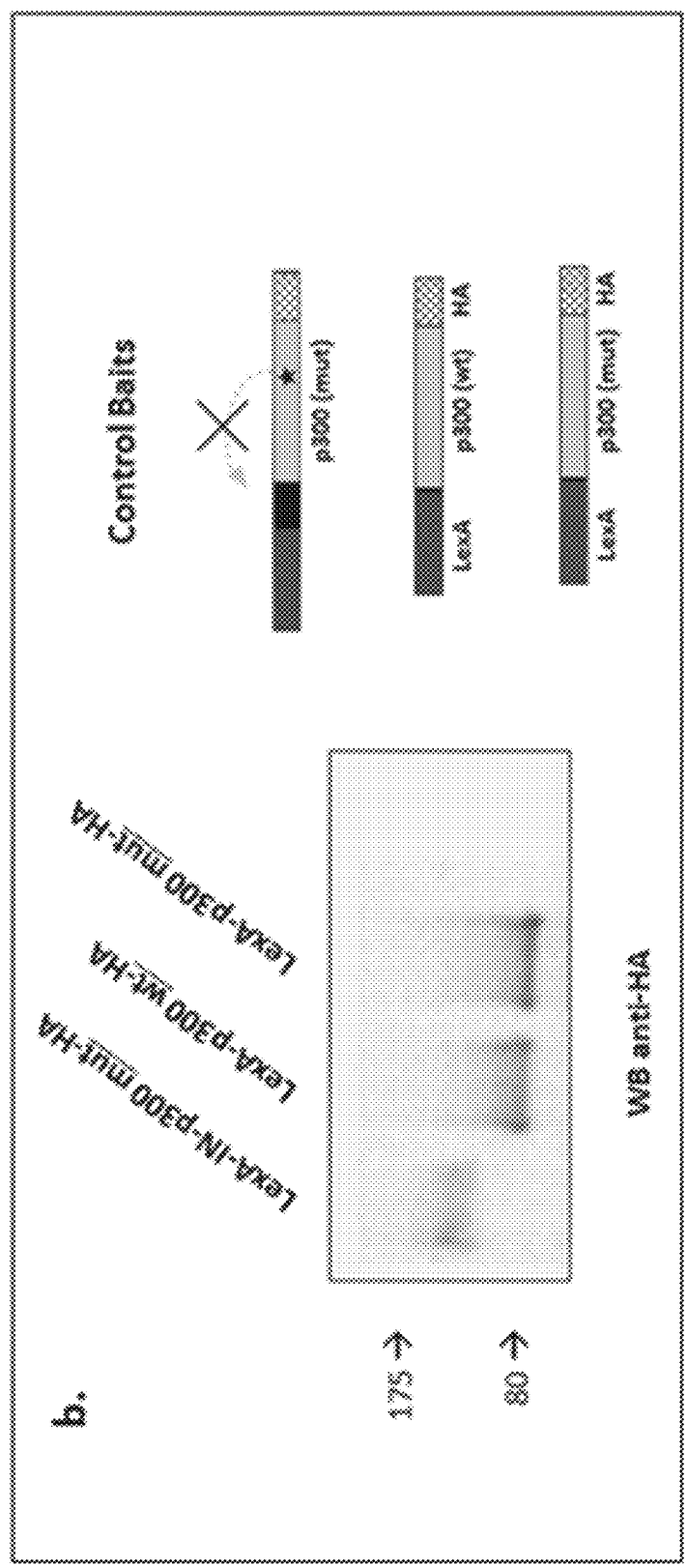
Fig. 2 (2/3)

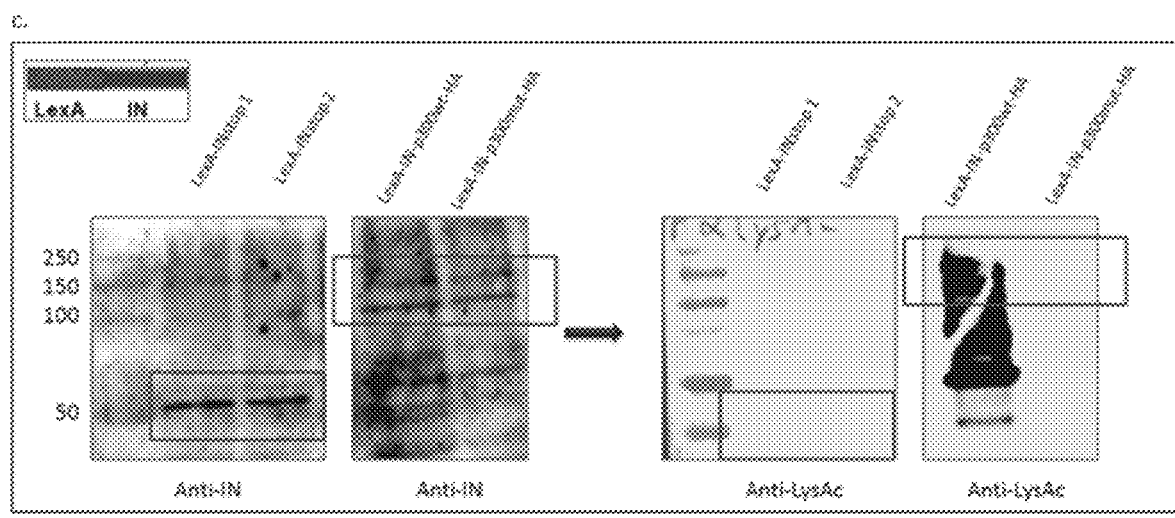
Fig. 2 (3/3)

Fig. 5

Fig. 6

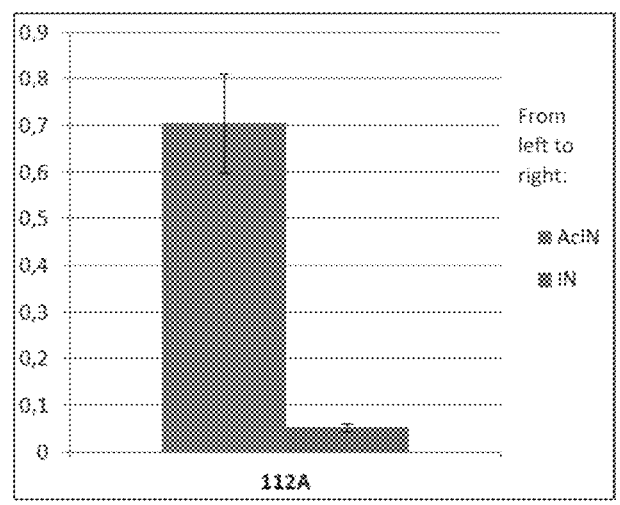
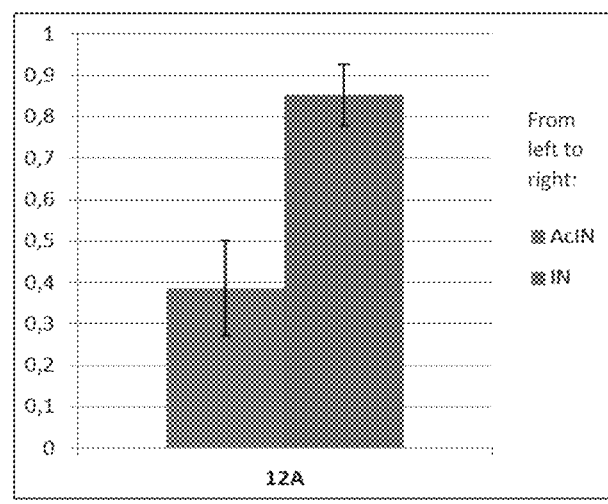
Fig. 13 a
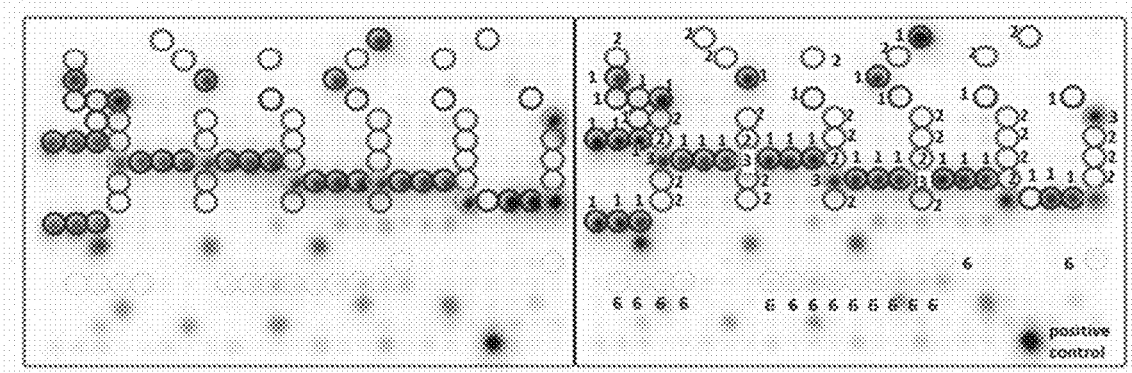
b
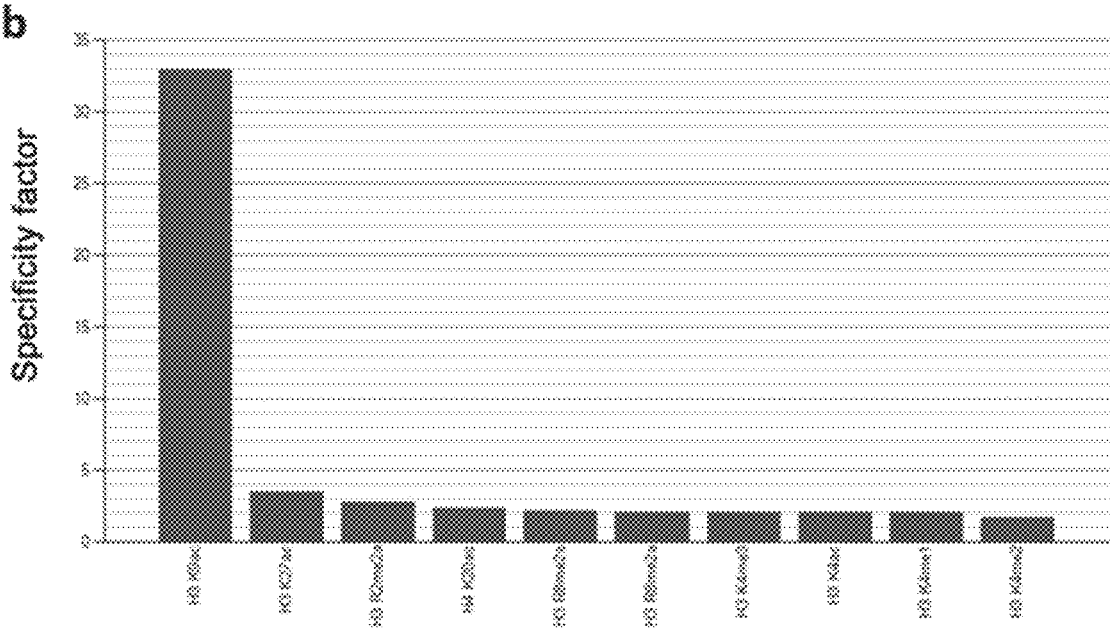
Fig. 15

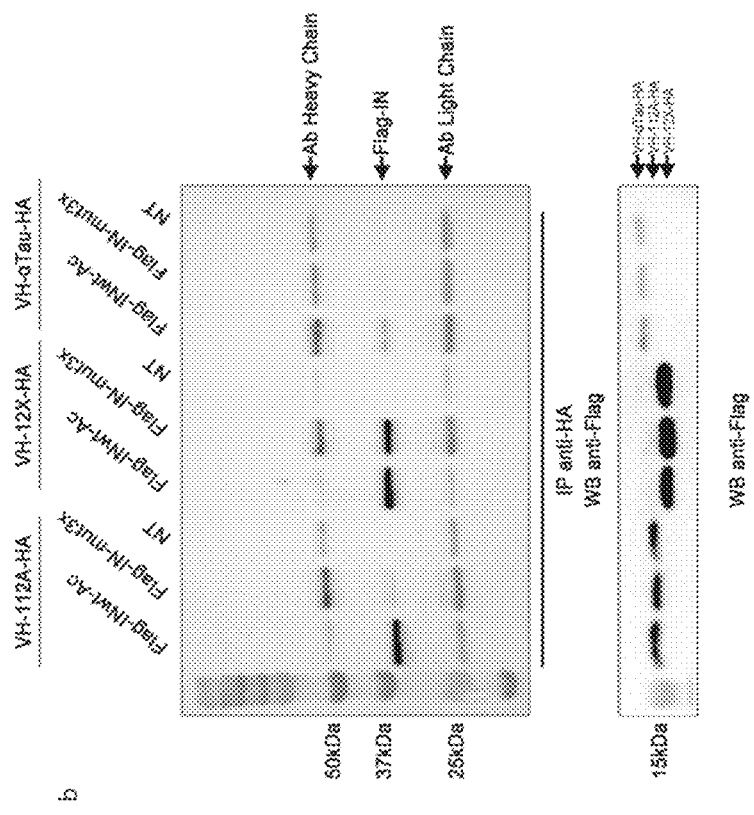
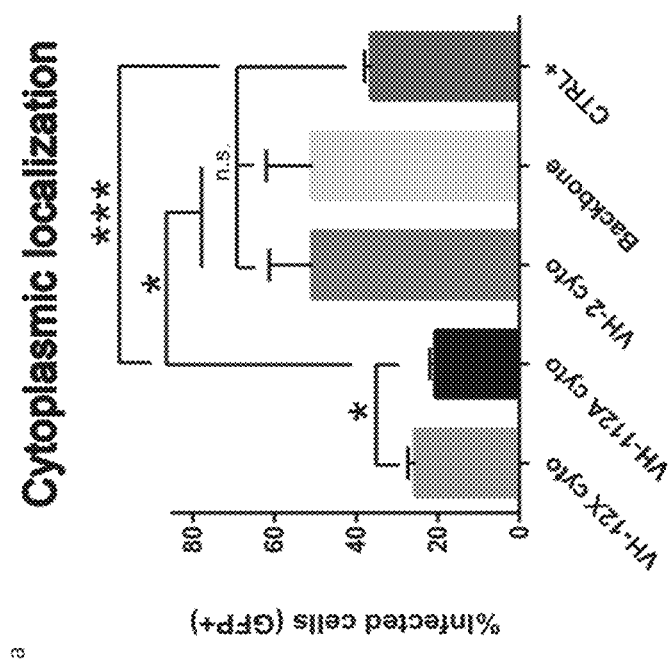
Fig. 19

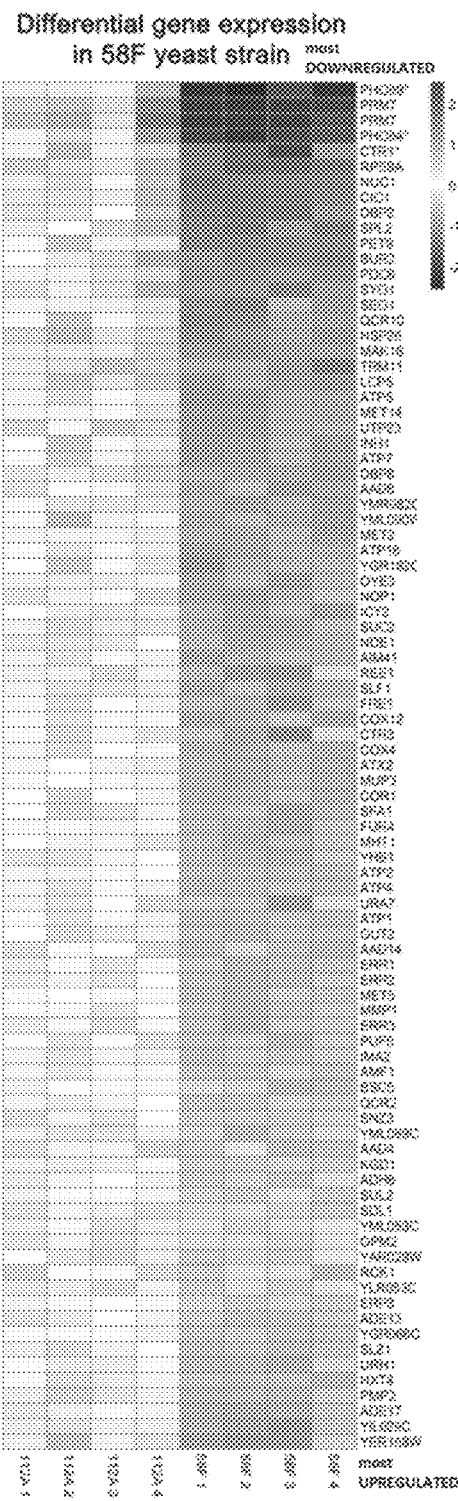
Fig. 20 (1/3)

b
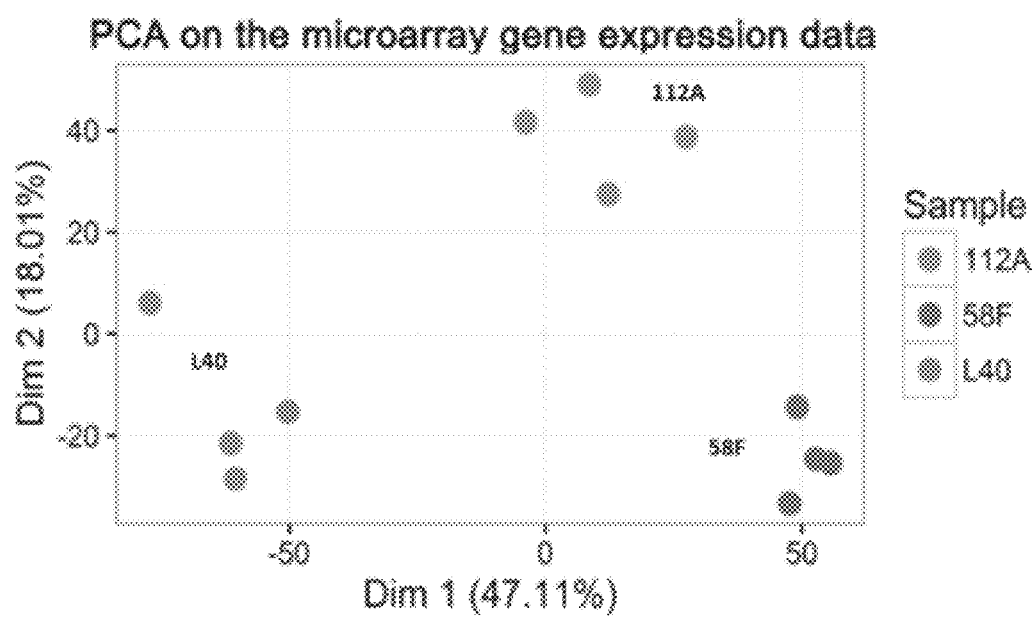
Fig. 20 (2/3)

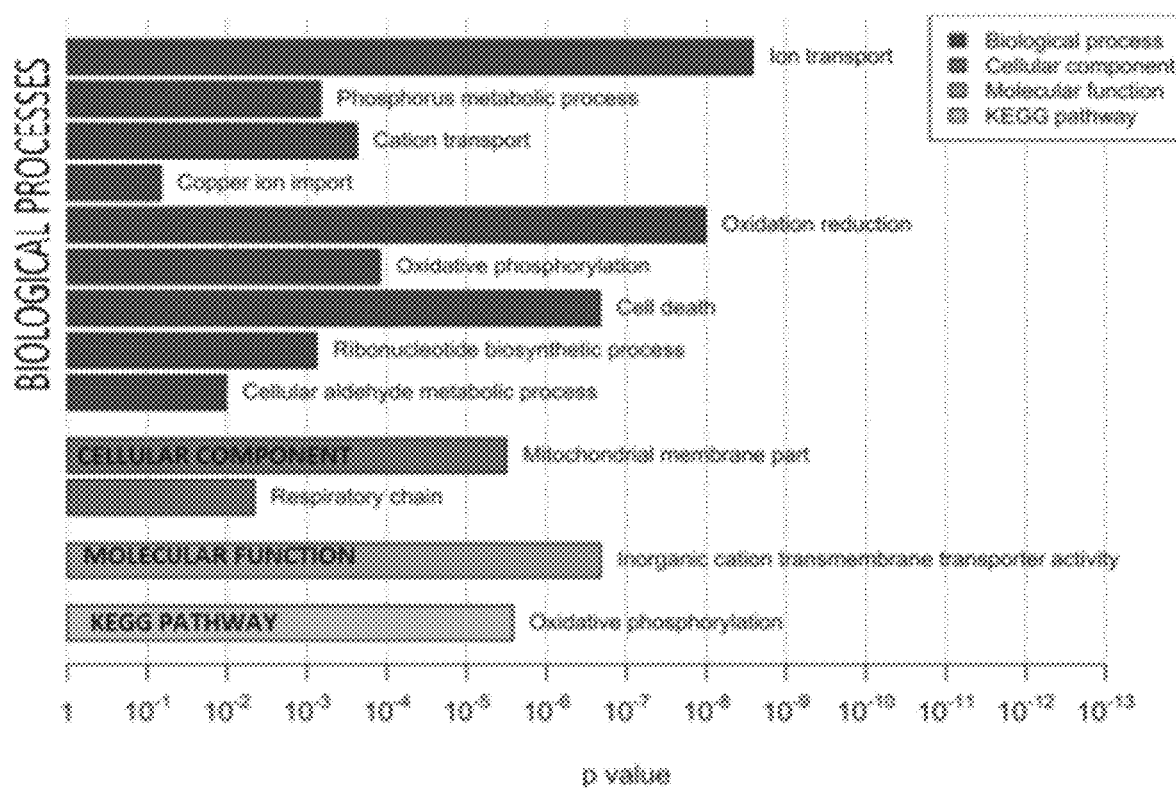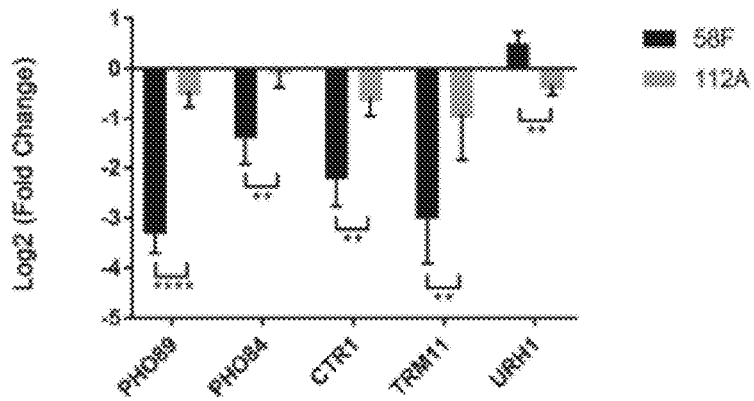
Fig. 20 (3/3)

INTRABODIES TARGETING POST-TRANSLATIONAL MODIFICATIONS OF NATIVE PROTEINS AND METHOD FOR OBTAINING THEM

CROSS-REFERENCE TO RELATED APPLICATIONS

This application is a 371 of PCT/EP2016/076447, filed Nov. 2, 2016, which claims the benefit of Italian Patent Application No. 102015000068085, filed Nov. 2, 2015.

FIELD OF THE INVENTION

The present invention relates to a method for determining the ability of an immunoglobulin to bind to a post-translationally modified target in an intracellular environment and to immunoglobulins targeting post-translationally modified targets.

BACKGROUND OF THE INVENTION

Protein Post-Translational Modifications (PTMs), such as acetylation, phosphorylation, ubiquitination, are crucial for the life of a cell. Thanks to PTMs, cells can exert plenty of physiological processes like signal transduction, gene regulation, protein clearance, chromatin remodeling, endocytosis. Therefore, after its modification, a protein acquires a new role in the cell, becoming now able to interact with totally different partners to create new ramification pathways. PTMs increase the diversity of the proteome by orders of magnitude and represent the most universal switch element connecting or interrupting the contacts between proteins in intracellular protein networks. In the proteomic and epigenetic era, exploring and dissecting finely these PTM-depending interactions has become an urgent need. Post translationally modified proteins represent a large universal class of targets for drug development or for diagnostic purposes. Validating these post translationally modified proteins as targets important for pharmaceutical developments is a daunting task, as no general technology exists today, that would allow a functional validation of PTMs. Indeed, the most commonly, widely and successfully used techniques for functional studies, needed to validate a target for pharmaceutical development, such as Gene K.O., RNAi or CRISPRs, fail to discriminate between two different modified versions of a same protein, since they can only deplete, or interfere with, the whole gene or its transcripts. Small chemical molecules have also been used for PTM interference, but they are poorly specific, non-generally selectable, and they cannot be targeted to a particular sub-cellular compartment. Most importantly, no general technology exists that would allow to streamline the isolation of small chemical molecules against PTM and small molecules have to be discovered on a one-to-one ad hoc basis. Antibodies represent a very useful class of reagents with the potential of recognizing a virtually unlimited chemical repertoire of specificities, including PTMs and could in principle represent a solution to the problem. Indeed, antibodies against PTMs are currently being produced, isolated and used for functional studies. However, no technology exists currently to stream line the isolation of antibodies against PTMs and to generate a pipeline of anti PTM antibodies to be used for target validation functional studies or for diagnostic and therapeutic purposes. The current state of the art in generating antibodies against PTMs is greatly limited by the fact that the antigen, used for antibody isolation, is a peptide chemically synthetized to harbor the desired post translational modification. This synthetic antigen is then used for immunization of animals. In this way, isolated antibodies (usually polyclonal or monoclonal antibodies) are anti peptide antibodies, with all the limitations and difficulties of recognizing the native protein harboring the PTM. Moreover, the use of these current generation anti PTM antibodies for functional studies is forcedly limited to biochemical and immunofluorescence studies, or in vitro functional assays. No PTM-selective functional interference in vivo is possible with current generation antibodies.

Yuko Sato et al., Genetically encoded system to track histone modification in vivo, Scientific Reports, vol. 3, no. 2436, p. 1-7, 2013, refers to fluorescent-modification-specific intracellular antibodies (mintbodies) that can be expresses in vivo, as e.g. an H3 lysine 9 acetylation specific mintbody (H3K9ac-mintbody)

Y. Hayashi-Takanaka et al., Nucleic Acids Research, vol. 39, no. 15, p. 6475-6488, 2011 refers to fluorescently labeled specific antigen biding fragments (Fabs) to monitor endogenous H3 lysine modifications, Kimura Hiroshi et al., Histochemistry and cell biology, springer, vol. 144, no. 2, p. 101-109, 2015 refers to fluorescently labeled Fabs loaded into the cells which bind to target modifications in the nucleus. Said publication also discloses the production of H3K9ac-specific mintbody by cloning the scFV coding sequence from hybridoma cells producing the specific antibody against histone H3 Lys9 acetylation (H3K9ac) and then genetically fused the scFV with EGFP.

The above described mintbody is only used for imaging histone acetylation in cells. Thus, said mintbody is able to bind chromatin and track it in living systems thanks to the fusion of a EGFP protein. No functional interference whatsoever is described.

US2013/0196867 refers to antibodies against acetylated histone.

WO00/54057 refers to a general immunoglobulin-target assay system, in which a positive outcome (the generation of a signal) depends only on the intracellular interaction of immunoglobulin with target. This can be accomplished for many immunoglobulins expressed in yeast and/or in mammalian cells and allows the selection of immunoglobulins which are capable of functioning in an intracellular environment.

WO02/35237 refers to a method for the in vivo identification of epitopes of an intracellular antigen comprising the steps of: a) co-transforming of cells by a first vector including the nucleotide sequence encoding the region of an antibody able to recognise and bind the intracellular antigen and by a second vector comprising the nucleotide sequence encoding a peptide; b) growing co-transformed cells in such an environment that only cells wherein the antibody region and peptide recognize and interact each other are able to replicate and/or be recognized because: the antibody region able to recognize and bind the intracellular antigen is associated with a first molecule; the peptide is associated with a second molecule; the interaction of the first with the second molecule generates a selectable phenotype and/or recognizable signal; and the interaction of the first with the second molecule occurs only when the antibody region and peptide recognize and interact each other; c) selecting the b) cells and identify the peptide as epitope.

WO03/014960 refers to a method of identifying at least one consensus sequence for an intracellular antibody (ICS) comprising the steps of: creating a database comprising sequences of validated intracellular antibodies (VIDA database) and aligning the sequences of validated intracellular antibodies according to Kabat; determining the frequency with which a particular amino acid occurs in each of the positions of the aligned antibodies; selecting a frequency threshold value (LP or consensus threshold) in the range from 70% to 100%; identifying the positions of the alignment at which the frequency of a particular amino acid is greater than or equal to the LP value; and identifying the most frequent amino acid, in the positions of said alignment.

WO2004/046192 refers to a method for isolating neutralizing intracellular antibodies of an interaction between a protein ligand x and a protein ligand y inside a cell and to a method to identify a protein ligand x able to bind to a known y ligand using intracellular antibodies able to disrupt the interaction between x and y. A method for the isolation of a set of antibody fragments against a significant proportion of the protein-protein interactions of a given cell (interactome) or against the protein interactions that constitute an intracellular pathway or network is also described.

None of the cited documents disclose methods allowing the selection of antibodies which specifically bind to recombinant proteins carrying post-translational modifications.

SUMMARY OF THE INVENTION

With this invention, inventors have overcome the above issues, by developing "P.I.S.A." platform (Posttranslational Intracellular Silencing Antibody Platform), a new selection platform for Intracellular Antibodies (Intrabodies), either in the ScFv format (linked VH and VL) or Nanobody format (either VH or VL domain), which allows general and robust intracellular selection of specific antibody domains against virtually any PTM-protein. In this technology, there is no need to chemically synthetize the PTM in a peptide, but the PTM is introduced by the cell into the native target protein. Thus, the technology generates antibody domains that are targeted to the PTM modified protein in its native state. Also, the technology generates antibodies that are ensured to function as intracellular antibodies (while antibodies generated by the current state of the art methods are not) that can be used downstream for functional PTM-specific interference in cells. No other general method is currently available to achieve a functional PTM specific protein silencing in cells. This method is based on the novel combination of two different technologies: i) the IAC technology (Intracellular Antibody Capture Technology) (Visintin et al., 1999; Visintin et al. 2002 and described in international patent application PCT WO00/54057, herein incorporated by reference), that permits in vivo isolation of the required intrabody from a library of antibody domains and ii) Tethered Catalysis (Guo D., Nature Biotechnology, 2004, 22(7)), by which it is possible to create two-hybrid system baits that present a constitutive post-translational modification. The new PISA method allows for the isolation of antibody domains recognizing PTMs in the native proteins, directly from gene sequences, with no manipulation whatsoever of the PTM antigen. The method provides not only the antibodies but also the genes coding for the antibodies, so downstream uses are greatly facilitated and made more general. In particular, this allows to perform a PTM-selective and PTM-specific protein interference in cells, thus allowing a general method to validate PTM targets for pharmaceutical purposes. Tethered Catalysis has been developed originally to find natural partners for PTM-proteins. Tethered catalysis works by genetically fusing the enzyme that modifies in vivo the target at the c-term of the target itself (e.g. Histone H3 (which may be represented by the sequence of gene ID 852295 or fragments thereof) fused with Gcn5 (which may be represented by the sequence of gene ID 853167 or fragments thereof) HAT enzyme). In the original method the whole construct is then fused at the C-term of Gal4 DNA binding domain (DBD) and it is used to screen cDNA yeast protein libraries only. The present platform uses the principle of tethered catalysis (i.e. target bait fused to the modifying enzyme), but the fusion protein exploits the LexA/VP16 two-hybrid system, and the PTM-modified bait is challenged NOT with a library of endogenous genes, but with a library of cDNA encoding naïve antibody domains, for PTM-specific intrabody selection. However, the presented method is not intrinsically dependent on tethered catalysis. Indeed, in a further embodiment of the invention, the tethered catalysis step can be substituted by the direct, site-specific genetic encoding of the PTM into the target protein, and using IAC to isolate antibodies from the genetically PTM-encoding bait.

It is therefore an object of the present invention a method for selecting an immunoglobulin able to bind in an intracellular environment to a post-translationally modified target or for determining the ability of an immunoglobulin to bind in an intracellular environment to a post-translationally modified target, said method comprising the steps of:

a) providing a nucleic acid encoding an intracellular immunoglobulin which is associated with a first molecule; and b) providing a nucleic acid encoding an intracellular target which is associated to:

an enzyme that modifies in vivo the target or subjected to a direct site-specific genetic encoding of the Post-Translational Modifications (PTM) into the target protein and a second molecule, wherein said first and second molecules are separable domains of a reporter molecule; and c) expressing said first nucleotide sequence together with said second nucleotide sequence in an intracellular environment, wherein binding of said immunoglobulin with said target leads to stable interaction of the first molecule and second molecule, thus producing a detectable reporter molecule that generates a signal, and d) detecting said signal from said detectable reporter molecule, wherein said detection of a signal is indicative of stable binding activity between said immunoglobulin and said target in the intracellular environment;

e) isolating those immunoglobulins that stably bind to the target and optionally f) selecting those immunoglobulins that do not bind to target that is not post-translationally modified.

Another object of the invention is a method for selecting an immunoglobulin able to bind in an intracellular environment to a post-translationally modified target or for determining the ability of an immunoglobulin to bind in an intracellular environment to a post-translationally modified target, said method comprising the steps of:

a) providing a nucleic acid encoding an intracellular immunoglobulin which is associated with a first molecule; and b) providing a nucleic acid encoding an intracellular target which incorporates a post translational modification that is genetically encoded via expanded genetic code methods and a second molecule, wherein said first and second molecules are separable domains of a reporter molecule; and c) expressing said first nucleotide sequence together with said second nucleotide sequence in an intracellular environment of a cell able to decode such genetically encoded post translational modification, wherein binding of said immunoglobulin with said target leads to stable interaction of the first molecule and second molecule, thus producing a detectable reporter molecule that generates a signal, and d) detecting said signal from said detectable reporter molecule, wherein said detection of a signal is indicative of stable binding activity between said immunoglobulin and said target in the intracellular environment;

e) isolating those immunoglobulins that stably bind to the target and optionally f) selecting those immunoglobulins that do not bind to target that is not post-translationally modified.

Preferably, the nucleic acid encoding the immunoglobulin is obtained from a library encoding a repertoire of immunoglobulin-encoding nucleic acids and/or no prior application of phage display is used to isolate immunoglobulins which bind to a target.

The post-translational modification is preferably at least one modification selected from the group consisting of: acetylation, phosphorylation, SUMOylation, polyubiquitination and monoubiquitination, methylation, trimethylation, succynilation, S-glutathionylation, adenylylation, amidation, myristoylation, palmitoylation, prenylation, alkylation, tyrosylation, nitrosylation.

The post-translation modified target is preferably acetylated histone.

The post-translation modified target is preferably acetylated histone H3, acetylated HIV-integrase or phosphorylated Tau.

A post-translationally modified target refers to a intracellular native protein which folds and is post-translationally modified as a native protein within the cell.

The reporter molecule is preferably selected from the group consisting of a transcription factor, an enzyme and a bioluminescent molecule, more preferably the reporter molecule is an enzyme and the method is performed in the presence of a substrate for the enzyme.

In a preferred embodiment of the invention, the first molecule is the activation domain of VP16 and the second molecule is the DNA-binding domain of LexA.

LexA may be represented by the sequence of gene ID 948544 or fragments thereof.

Preferably, the detecting step is selected from the group consisting of: a change in an optical property and the activation of a reporter gene, and/or allows the sorting of cells.

Preferably, the immunoglobulin is selected from the group consisting of an intact immunoglobulin, a Fv, a scFv (single chain Fv fragment), a Fab, a F(ab')2, an "antibody-like" domain, an "antibody-mimetic domain", a single antibody domain (VH domain or VL domains).

The antibody like domain comprises binding proteins structurally related to antibodies such as T cell receptors.

The term "antibody mimetics" refers to those organic compounds that are not antibody derivatives but that can bind specifically an antigen like antibodies do. They include anticalins, DARPins, affibodies, affilins, affimers, affitins, alphabodies, avimers, fynomers, monobodies and others.

The single antibody domain is also called Nanobody (VH domain or VL domains).

The library is preferably a naive SPLINT human or mouse ScFv library, or a naïve SPLINT human VH library or a phage library encoding a repertoire of immunoglobulins, suitably preselected before being expressed in the IAC format.

Optionally, the library is constructed from nucleic acids isolated from an organism which has been challenged with an antigen.

Other objects of the invention is an intracellular immunoglobulin, recombinant or synthetic antigen-binding fragments thereof obtainable by the method above described, which preferably recognizes and binds acetylated histone, preferably acetylated histone H3, or acetylated HIV-integrase or phosphorylated Tau.

The intracellular immunoglobulin, recombinant or synthetic antigen-binding fragments according to the invention preferably specifically binds acetylated lysine 9 of histone H3 and/or competes for biding to acetyl histone 3.

The intracellular immunoglobulin, recombinant or synthetic antigen-binding fragments of the invention is preferably able to recognise and bind an epitope comprising the SEQ ID NO: 6.

The intracellular immunoglobulin, recombinant or synthetic antigen-binding fragments thereof according to the invention preferably specifically binds acetyl-HIV1-integrase and/or competes for biding to acetyl-HIV1-integrase.

The intracellular immunoglobulin, recombinant or synthetic antigen-binding fragments thereof according to the invention preferably comprises at least one heavy chain complementary determining region (CDRH3) amino acid sequence having at least 80% identity to an amino acid sequence selected from the group consisting of: SEQ. ID NO:82, SEQ. ID NO: 88 and SEQ. ID NO: 91.

The intracellular immunoglobulin, recombinant or synthetic antigen-binding fragments thereof according to the invention preferably further comprises a heavy chain complementary determining region (CDRH2) amino acid sequence having at least 80% identity to an amino acid sequence selected from the group consisting of: SEQ ID NO: 81, SEQ. ID NO: 87, SEQ. ID NO: 90.

The intracellular immunoglobulin, recombinant or synthetic antigen-binding fragments thereof according to the invention preferably further comprise a heavy chain complementary determining region (CDRH1) amino acid sequence having at least 80% identity to an amino acid sequence selected from the group consisting of: SEQ ID No. 80, SEQ. ID NO: 86, SEQ. ID NO: 89.

The intracellular immunoglobulin, recombinant or synthetic antigen-binding fragments thereof according to the invention preferably further comprise:
  at least one light chain complementary determining region (CDRL3) amino acid sequence having at least 80% identity to SEQ. ID NO: 85 and/or
  at least one light chain complementary determining region (CDRL2) amino acid sequence having at least 80% identity to SEQ. ID NO: 84 and/or
  at least one light chain complementary determining region (CDRL1) amino acid sequence having at least 80% identity to SEQ. ID NO: 83.

In a preferred embodiment, the intracellular immunoglobulin, recombinant or synthetic antigen-binding fragments thereof comprise a heavy chain complementary determining region (CDRH1) amino acid sequence having at least 80% identity to an amino acid sequence of SEQ ID NO: 80 and a heavy chain complementary determining region (CDRH2) amino acid sequence having at least 80% identity to an amino acid sequence of SEQ ID NO: 81 and a heavy chain complementary determining region (CDRH3) amino acid sequence having at least 80% identity to an amino acid sequence of SEQ ID NO: 82.

In a more preferred embodiment, the intracellular immunoglobulin, recombinant or synthetic antigen-binding fragments thereof further comprise a light chain complementary determining region (CDRL1) amino acid sequence having at least 80% identity to an amino acid sequence of SEQ. ID NO: 83 and a light chain complementary determining region (CDRL2) amino acid sequence having at least 80% identity to an amino acid sequence of SEQ. ID NO: 84 and a light chain complementary determining region (CDRL3) amino acid sequence having at least 80% identity to an amino acid sequence of SEQ. ID NO:85.

Preferably, the intracellular immunoglobulin, recombinant or synthetic antigen-binding fragments thereof according to the invention comprise a heavy chain complementary determining region (CDRH1) amino acid sequence having at least 80% identity to an amino acid of SEQ ID NO: 80 and a heavy chain complementary determining region (CDRH2) amino acid sequence having at least 80% identity to an amino acid sequence of SEQ ID NO: 81 and a heavy chain complementary determining region (CDRH3) amino acid sequence having at least 80% identity to an amino acid sequence of SEQ ID NO: 82, and a light chain complementary determining region (CDRL1) amino acid sequence having at least 80% identity to an amino acid sequence of SEQ. ID NO: 83 and a light chain complementary determining region (CDRL2) amino acid sequence having at least 80% identity to an amino acid sequence of SEQ. ID NO: 84 and a light chain complementary determining region (CDRL3) amino acid sequence having at least 80% identity to an amino acid sequence of SEQ. ID NO:85.

In a preferred embodiment, the intracellular immunoglobulin, recombinant or synthetic antigen-binding fragments thereof comprise a CDRH1 amino acid sequence having at least 80% identity to SEQ ID No. 86, a CDRH2 amino acid sequence having at least 80% identity to SEQ ID No. 87 and a CDRH3 amino acid sequence having at least 80% identity to SEQ ID No. 88.

In a further preferred embodiment, the intracellular immunoglobulin, recombinant or synthetic antigen-binding fragments thereof comprise a CDRH1 amino acid sequence having at least 80% identity to SEQ ID No. 89, a CDRH2 amino acid sequence having at least 80% identity to SEQ ID No. 90 and a CDRH3 amino acid sequence having at least 80% identity to SEQ ID No. 91.

Preferably, the intracellular immunoglobulin, recombinant or synthetic antigen-binding fragments thereof as abode defined, comprise a heavy chain variable region amino acid sequence having at least 80% identity to the amino acid sequence selected from the group consisting of SEQ ID NOs: 92, 2 or 1 or fragments thereof and/or a light chain variable region amino acid sequence having at least 80% identity to the amino acid sequence of SEQ ID NOs: 93, or fragments thereof.

More preferably, the intracellular immunoglobulin, recombinant or synthetic antigen-binding fragments thereof of the invention comprise a sequence having a % of amino acid sequence identity of at least 80% with SEQ ID NO:3, SEQ ID NO:2 or SEQ ID NO:1.

Further object of the invention is an isolated nucleic acid molecule encoding the intracellular immunoglobulin, recombinant or synthetic antigen-binding fragments thereof as defined above or hybridizing with said nucleic acid, or a degenerate sequence thereof. Preferably, said nucleic acid molecule has sequence having at least 80% identity to the nucleotide sequence of SEQ ID NOs: 99, 98 or 97 or fragments thereof.

Other objects of the invention are an expression vector encoding the intracellular immunoglobulin, recombinant or synthetic antigen-binding fragments thereof as above defined, an isolated host cell comprising the nucleic acid as above defined, said cell preferably producing the intracellular immunoglobulin, recombinant or synthetic antigen-binding fragments thereof as above defined.

Another object of the invention is the intracellular immunoglobulin, recombinant or synthetic antigen-binding fragments of the invention or the nucleic acid molecule of the invention or the expression vector of the invention or the host cell of the invention for medical use, preferably for use in the prevention and/or treatment of a pathology in which the immunoglobulin is able to bind a key molecule implicated in the pathological process, preferably said condition being AIDS (Acquired Immune Deficiency Syndrome) or cancer.

In particular, the intracellular immunoglobulin, recombinant or synthetic antigen-binding fragments thereof as above defined comprising a sequence having a % of amino acid sequence identity of at least 80% with SEQ ID NO:1 or 2 or SEQ ID NOs: 86 and/or 87 and/or 88, or SEQ ID Nos: 89 and/or 90 and/or 91 and the nucleic acid molecule encoding it are preferably for use in the prevention and/or treatment of a pathology in which the immunoglobulin is able to bind a key molecule implicated in the pathological process, more preferably said condition being AIDS.

The intracellular immunoglobulin, recombinant or synthetic antigen-binding fragments thereof as above defined comprising a sequence having a % of amino acid sequence identity of at least 80% with SEQ ID NOs:3, or SEQ ID Nos: 92 and/or 93, or SEQ ID Nos: 80 and/or 81 and/or 82 and/or 83 and/or 84 and/or 85 or the nucleic acid molecule encoding it is preferably for use in the prevention and/or treatment of any pathology in which the immunoglobulin is able to bind a key molecule implicated in the pathological process, more preferably said condition being cancer. In the context of the present invention, the term "cancer" includes e.g. lukemia, glioblastoma, lymphomas, blood cell cancers, brain tumors, breast cancer, colon cancer, pancreatic cancer.

A further object of the invention is the use of the intracellular immunoglobulin, recombinant or synthetic antigen-binding fragments thereof as above defined or the nucleic acid molecule encoding it or the expression vector or the host cells as above defined for PTM-selective functional interference in cells, for gene therapy, for Chromatin immunoprecipitation, for in vitro assays such as ELISA, Western Blot, Dot Blot, or functional effector coupling. Another object of the invention is the use of the intracellular immunoglobulin, recombinant or synthetic antigen-binding fragments thereof according to the invention or the nucleic acid molecule according to the invention as scaffolds to derive small chemical mimics.

A further object of the invention is the use of the intracellular immunoglobulin, recombinant or synthetic antigen-binding fragments thereof as above defined or the nucleic acid molecule of the invention for silencing genes by silencing the action of acetylated chromatin, wherein preferably the silencing leads to transcriptomic functional effects.

Another object of the invention is a method of producing the immunoglobulin as above defined comprising culturing the cell that produces the immunoglobulin of the invention and recovering the immunoglobulin from the cell culture.

Another object of the invention is a pharmaceutical composition comprising at least one immunoglobulin, recombinant or synthetic antigen-biding fragments thereof or nucleic acid molecule according to the invention and pharmaceutically acceptable excipients.

Preferably, said composition is for use in intraperitoneal, intramuscular or intranasal administration. In the case of nucleic acid molecule, the administration may be by gene therapy by ex vivo genetic modification of cells or by direct infection of tissue cells in the organism, using viral vectors or other gene delivery methods.

Another object of the invention is a recombinant yeast strain comprising a pair of tRNA/AA-RNA synthetase matching set.

The recombinant yeast strain preferably comprises a sequence having a % of nucleotide sequence identity of at least 80% with SEQ ID NO: 79. Said yeast is preferably L40.

Other objects of the invention are the use of the above defined genetically engineered yeast strain to select intrabodies against PTMs genetically encoded in the target antigen through the use of intragenic amber stops; an isolated nucleotide sequence comprising a sequence having a % of nucleotide sequence identity of at least 80% with SEQ ID NO: 79; an isolated amino acidic sequence comprising a sequence having a % of amino acid sequence identity of at least 80% with SEQ ID NOs: 78, 12, 13, 14, 15, 16, 17, 18, 19, 20 or 21.

Another object of the invention is a method for obtaining a human naïve VH SPLINT (Single Pot Library of INTracellular antibodies) library, with the VH domains deriving from antibodies of the IgM isotype, comprising the steps of:

a) amplifying human germline VH regions, from a cDNA sample, preferably made from human isolated splenocytes or isolated peripheral blood lymphocytes, with primers for the 5' and the 3' specific for VH bearing two different restriction sites to obtain VH products;

b) digesting the obtained VH products with the specific restriction enzymes and ligating them to a digested vector.

Preferably, the primers used in step a) are: SEQ ID NOs: 34 and/or 35 and/or 36 and/or 37.

Another object of the invention is a method for obtaining a human naïve single domain scFv SPLINT (Single Sot Library of INTracellular antibodies) library, with the VH and VL domains deriving from antibodies of the IgM isotype comprising the steps of:

a) amplifying human germline VH, Vk and Vλ regions, from a cDNA sample, preferably made from isolated human splenocytes or isolated human peripheral blood lymphocytes, more preferably from isolated peripheral blood lymphocytes, with primers able to anneal at the beginning of the external framework regions of the V gene, producing a blunt product (Variable region amplicon);

b) amplifying a linker blunt specific for VH, Vk or Vλ regions, with primers having the same 3' region annealing on the linker and different protruding 5', overlapping perfectly either with VH framework 4 or VL framework 1 to obtain a semi-blunt linker;

c) carrying out an overlap amplification between the Variable region amplicons and the semi-blunt linkers, obtaining VH-linker and linker-VL, i.e. VH and VL protruding with the same linker sequence at 3' and 5' respectively;

d) joining VH-linker and linker-VL by overlapping amplification;

e) inserting restriction sites at the 5' of the VH regions and at the 3' of the Vk and Vγ regions to obtain scFv products;

f) digesting the scFv products with the specific restriction enzymes and ligating them to a digested vector.

Said linker preferably consists of a sequence of from 15aa to 19aa which is not subjected to intracellular cleavage by proteases, preferably said linker has a sequence of SEQ ID NO: 94 (GGGGSGGGGSGGGGS).

The linker used for scFv human SPLINT library is the (Gly4-Ser)3 linker, which has a length of 15 amino acids (45 bp) and has a sequence: GGGGSGGGGSGGGGS (SEQ ID NO:94) (or in nucleotides: 5' ggtggaggcggttcaggcggaggtggctctggcggtggcggatcg 3' (SEQ ID NO:95))

All the variants in nucleotide sequence (according to genetic code) that produce the same proteic sequences will work equally as linker, but this specific nucleotide sequence is preferred because of codon usage and easiness of amplification during PCR step.

Another example of linker is the sequence GSTSGSGKPGSGEGSSST (SEQ ID NO:96).

Preferably, the primers used in step a) for Vk are: SEQ ID NOs: 38 and/or 39 and/or 40 and/or 41 and/or 42 and/or 43 and/or 44 and/or 45 and/or 46 and/or 47 and/or 48.

Preferably, the primers used in step a) for Vλ are: SEQ ID NOs: 49 and/or 50 and/or 51 and/or 52 and/or 53 and/or 54 and/or 55 and/or 56 and/or 57 and/or 58.

The primers used in step a) for VH are preferably: SEQ ID NOs: 24 and/or 25 and/or 26 and/or 27 and/or 29 and/or 30 and/or 31 and/or 32 and/or 33.

Preferably, the primers used in step b) are: SEQ ID NOs: 59 and/or 60 and/or 61 and/or 62 and/or 63 and/or 64 and/or 65 and/or 66 and/or 67 and/or 68 and/or 69 and/or 70 and/or 71 and/or 72 and/or 73 and/or 74 and/or 75 and/or 76 and/or 77.

Preferably, the cDNA of step a) is obtained by retrotranscribing heavy and light chains of IgM antibodies from RNA to cDNA.

Preferably, the primers used for cDNA amplification are SEQ ID NOs:22 and 23. The above methods preferably further comprises a preliminary step of extracting total RNA from isolated human splenocytes or isolated human peripheral blood lymphocites (PBLs). The amplification is preferably carried out by PCR.

A further object of the invention is the human naïve single domain VH or scFv SPLINT (single pot library of intracellular antibodies) library obtainable by the above defined methods.

In a preferred embodiment of the methods for selecting an immunoglobulin able to bind in an intracellular environment to a post-translationally modified target or for determining the ability of an immunoglobulin to bind in an intracellular environment to a post-translationally modified target according to the invention, the naïve SPLINT human library, is the library obtainable by above defined the methods.

It is also an object of the invention a method of treating and/or preventing a cancer or metastasis or AIDS comprising administering a therapeutically effective amount of the immunoglobulin or fragment or derivative or conjugate thereof or cellular composition or viral particle or host cells or nucleic acids as above defined.

The method for treating or preventing a cancer or metastasis or AIDS, comprises administering to a patient in need thereof an effective amount of at least one immunoglobulin, fragments or derivatives or conjugates thereof or cellular composition or viral particle or host cells or nucleic acids as described above. In some aspects, the invention comprises a method for treating or preventing cancer or metastasis in a subject, the method comprising administering to a subject in need thereof an effective amount of at least one immunoglobulin, fragments or derivatives or conjugates thereof or cellular composition or viral particle or host cells or nucleic acids of the invention simultaneously or sequentially with an anti-cancer agent.

The method according to the present invention is defined by the present inventors as "PISA (Post-translational Intracellular Silencing Antibody) platform" or "PISA" or "PISA technology".

In the method according to the present invention, those immunoglobulins that give rise to a signal are preferably isolated.

The method as above disclose may comprise the further step of:

g) subjecting the isolated immunoglobulins to a functional intracellular assay.

For example, where the assay is intended to select immunoglobulins which bind to post translationally modified targets which are associated with tumorigenesis, the immunoglobulins may be tested in a cell transformation assay to determine any modulating activity on the production of transformed cells. As another example, when the assay is intended to select immunoglobulins which bind to post translationally modified targets which are associated with viral infection, the immunoglobulins may be tested in a viral infection assay to determine any modulating activity on the production of infected cells.

Preferably, the isolated immunoglobulin is an "intracellular antibody" or "intrabody" (said terms being interchangeable).

"Intracellular" means inside a cell, and the present invention is directed to the selection of immunoglobulins which will bind to post-translationally modified targets selectively within a cell. The cell may be any cell, prokaryotic or eukaryotic, and is preferably selected from the group consisting of a bacterial cell, a yeast cell and a higher eukaryote cell. Most preferred are yeast cells and mammalian cells. In general, the assay of the invention is carried out in the cytoplasm of the cell, and determines the ability of the immunoglobulin to fold effectively within the cytoplasm and bind to its PTM target.

In a further embodiment, the method of the invention may be conducted under conditions which resemble or mimic an intracellular environment. Thus, "intracellular" may refer to an environment which is not within the cell, but is in vitro. For example, the method of the invention may be performed in an in vitro transcription and/or translation system, which may be obtained commercially, or derived from natural systems.

The first and second molecules may be any molecules, consistent with the requirement to generate a signal. They need not necessarily be polypeptides. For example, they may be fluorophores or other chemical groups capable of emitting or absorbing radiation. In a preferred aspect, however, the first and second molecules of the invention are polypeptides.

Polypeptides according to the invention associate to form a reporter molecule which is itself capable of giving a signal. Preferably, therefore, the polypeptides are domains of such a reporter molecule. For example, the polypeptides may be domains of a fluorescent polypeptide, such as GFP, or domains of a transcription factor which, when active, up regulates transcription from a reporter gene. The reporter gene may itself encode GFP, or another detectable molecule such as luciferase, 3-galactosidase, chloramphenicol acetyl transferase (CAT), an enzyme capable of catalysing an enzymatic reaction with a detectable end-point, or a molecule capable of regulating cell growth, such as by providing a required nutrient.

Association of the immunoglobulin and the target in accordance with the invention provides a stable link between the first and second molecules, which brings the molecules into stable interaction. "Stable interaction" may be defined as an interaction which permits functional cooperation of the first and second molecules in order to give rise to a detectable result, according to the signaling methods selected for use. Advantageously, a stable interaction between the first and second molecules does not occur unless the molecules are brought together through binding of the immunoglobulin and the target.

In a preferred embodiment, the immunoglobulin and target are provided by expressing nucleic acids within the cell in which the intracellular assay is to take place. The immunoglobulin and target constructs, which comprise the signal-generating molecules, are transcribed and/or translated from nucleic acid and localized to, for instance, the cytoplasm of the cell, where the intracellular assay may take place. In other advantageous embodiments, the intracellular immunoglobulins may be localized to any desired subcellular compartment, such as the nucleus (for example by fusion to a nuclear localization signal), to the ER, using an ER retention signal, or other locations.

Nucleic acids encoding immunoglobulins may be obtained from libraries encoding a multiplicity of such molecules. For example, phage display libraries of immunoglobulin molecules are known and may be used in this process. Advantageously, the library encodes a repertoire of immunoglobulin molecules. A "repertoire" refers to a set of molecules generated by random, semi-random or directed variation of one or more template molecules, at the nucleic acid level, in order to provide a multiplicity of binding specificities. Methods for generating repertoires are well characterized in the art.

Libraries may moreover be constructed from nucleic acids isolated from organisms which have been challenged with a target, for example an antigen made of a PTM target. Antigen challenge will normally result in the generation of a polyclonal population of immunoglobulins, each of which is capable of binding to the antigen but which may differ from the others in terms of epitope specificity or other features. By cloning immunoglobulin genes from an organism a polyclonal population of immunoglobulins may be subjected to selection using the method of the invention in order to isolate immunoglobulins which are suitable for use in intracellular environments.

The method of the invention permits the isolation of immunoglobulins which are capable of intracellular binding activity, and/or nucleic acids encoding such immunoglobulins, on the basis of the signal generated by the method set forth above. Accordingly, one or both of the immunoglobulin and the target used in the method of the invention, together with the first or second molecules, are provided in the form of nucleic acid constructs which are transcribed to produce said immunoglobulin and/or target together with said first or second molecules. Nucleic acid constructs may be expression vectors capable of directing expression of the nucleic acid encoding the immunoglobulin in the cell in which the method of the invention is to be performed.

As used above, "operative association" refers to the fusion or juxtaposition of coding sequences such that a fusion protein is produced, comprising the immunoglobulin and the signal-generating molecule. Normally, performing a selection against a target will generate a smaller repertoire of antibodies which share target specificity. The transcription units encoding such immunoglobulins, fused to the signal generating molecules, are employed in an assay according to the invention in order to select those immunoglobulins which are capable of functioning intracellularly.

It is another object of the invention a pharmaceutical composition comprising at least one immunoglobulin, antibody, recombinant or synthetic antigen-binding fragments thereof as described above and pharmaceutically acceptable excipients. The composition comprises an effective amount of the immunoglobulin, antibody, recombinant or synthetic antigen-binding fragments thereof. Pharmaceutical compositions are conventional in this field and can be made by the person skilled in the art just based on the common general knowledge.

For sake of brevity, the preferred antibody according to the present invention shall be identified with the name ScFv-58F (comprising SEQ ID NO: 3), VH-112A (comprising SEQ ID NO:2) and VH-12A (also herein referred as VH-12X and comprising SEQ ID NO: 1).

Still preferably, the antibody is a scFv, Fv fragment, a Fab fragment, a F(ab)2 fragment, a multimeric antibody, a peptide or a proteolytic fragment containing the epitope binding region. Preferably the scFv fragment comprises SEQ ID NO:3.

It is a further object of the present invention a nucleic acid encoding the immunoglobulin, the antibody or functional derivatives thereof of the invention (e.g. effector domains for protein degradation, imaging, catalysis and also genetic tags, binding switches, localization peptides) or hybridizing with the above nucleic acid, or consisting of a degenerated sequence thereof.

The process for the preparation of the antibody is within the skills of the man skilled in the art and comprises cultivating host cell and isolating the antibody according to standard procedures.

The antibodies of the present invention may comprise at least one of the sequence as defined above that contains one or more amino acid substitutions, deletions or insertions, preferably of no more than 16 amino acids, more preferably of no more than 8 amino acids. Said antibodies must retain the ability to bind to their epitope.

Antibodies selected with PISA platform, in a first round of selection, can undergo a further, optional step of selection called "affinity maturation screening". After generation of a sub-library, which is obtained by randomization of the target binding region of the "antibody", such as, for instance and not limited to, randomization of CDR2 and/or CDR1 of its variable domains, it is possible to increase affinity of a single domain antibody or ScFv retaining its specificity for the target (e.g. procedure described in Tanaka & Rabbitts, Nat Prot (2009)). Adaptation of the method to PISA platform is straightforward and done by adopting the same protocol described in the reference with minor modifications, but using PTM tethered catalysis baits instead, as described in the present invention.

The antibody or immunoglobulin of the invention thereof may be antagonist of the PTM-target.

The antibodies of the invention preferably compete for binding to acetyl-HIV-1 integrase or acetyl histone 3.

The antibodies, recombinant or synthetic antigen-binding fragments thereof of the invention selectively bind to acetyl-integrase or acetyl histone 3, preferably with a Kd that is less or equal than micromolar (e.g., nanomolar or still less).

The antibodies of the invention may be for medical use. Preferably, VH-12A and VH-112A are for use in the treatment of AIDS or any pathology in which the antibody is able to bind a key molecule implicated in the pathological process. Preferably, ScFv-58F is for use, as a chromatin modulator, in the treatment of cancer, in particular in cancer in which oncogene activation/tumor suppressor gene deactivation is due to epigenetic change of chromatin, or in the treatment of any pathology in which the antibody is able to bind a key molecule implicated in the pathological process. In general, PISA antibodies could be used as therapeutic agents on a case-by-case, ad hoc basis. PISA antibodies can also be used for diagnostic and target validation uses.

The terms "antibody" and "immunoglobulin" can be used interchangeably and are herein used in the broadest sense and encompass various antibodies and antibody mimetics structures, including but not limited to monoclonal antibodies, polyclonal antibodies, multispecific antibodies (e.g., bispecific antibodies), chimeric antibodies, nanobodies, antibody derivatives, antibody fragments, anticalins, DARPins, affibodies, affilins, affimers, affitins, alphabodies, avimers, fynomers, monobodies and other binding domains, so long as they exhibit the desired antigen-binding activity.

The term immunoglobulin also includes "conjugate" thereof. In the context of the present invention "conjugate" in relation to the antibody of the invention includes antibodies (or fragments thereof) conjugated with a substance (a compound, etc.) having a therapeutic activity, e.g. anti-tumor activity and/or cell-killing activity or a cytotoxic agents such as various A chain toxins, ribosomes inactivating proteins, and ribonucleases; bispecific antibodies designed to induce cellular mechanisms for killing tumors (see, for example, U.S. Pat. Nos. 4,676,980 and 4,954,617).

The conjugate may be formed by previously preparing each of the aforementioned antibody molecule and the aforementioned substance having anti-tumor activity and/or cell-killing activity, separately, and then combining them (immunoconjugate) or by ligating a protein toxin used as such a substance having anti-tumor activity and/or cell-killing activity to an antibody gene on a gene according to a genetic recombination technique, so as to allow it to express as a single protein (a fusion protein) (immunotoxin).

An "antibody fragment" refers to a molecule other than an intact antibody that comprises a portion of an intact antibody that binds the antigen to which the intact antibody binds.

Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments. VH or VL Fvs are also called "Nanobodies".

The term "antibody mimetics" refers to those organic compounds or binding domains that are not antibody derivatives but that can bind specifically an antigen like antibodies do. They include anticalins, DARPins, affibodies, affilins, affimers, affitins, alphabodies, avimers, fynomers, monobodies and others.

The term "chimeric" antibody refers to an antibody in which a portion of the heavy and/or light chain is derived from a particular source or species, while the remainder of the heavy and/or light chain is derived from a different source or species.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Percent (%) of amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

The term "pharmaceutical composition" refers to a preparation which is in such form as to permit the biological activity of an active ingredient contained therein to be effective, and which contains no additional components which are unacceptably toxic to a subject to which the formulation would be administered.

The pharmaceutical composition of the present invention can be administered in the form of a dosage unit, for example tablets or capsules, or a solution.

In the present invention the term "effective amount" shall mean an amount which achieves a desired effect or therapeutic effect as such effect is understood by those of ordinary skill in the art. In the present invention, the antibody may be administered simultaneously or sequentially with another therapeutic treatment, that may be a chemotherapy or radiotherapy.

The invention provides formulations comprising a therapeutically effective amount of an antibody as disclosed herein, a buffer maintaining the pH in the range from about 4.5 to about 8.5, and, optionally, a surfactant.

The formulations are typically for an antibody as disclosed herein, recombinant or synthetic antigen-binding fragments thereof of the invention as active principle concentration from about 0.1 mg/ml to about 100 mg/ml. In certain embodiments, the antibody, recombinant or synthetic antigen-binding fragments thereof concentration is from about 0.1 mg/ml to 1 mg/ml; preferably from 1 mg/ml to 10 mg/ml, preferably from 10 to 100 mg/ml.

Therapeutic formulations of the antibody/antibodies can be prepared by mixing the antibody having the desired degree of purity with optional physiologically acceptable carriers, excipients or stabilizers (Remington's Pharmaceutical Sciences 16th edition, Osol, A. Ed., 1980), in the form of lyophilized formulations or aqueous solutions.

Pharmaceutical compositions containing the antibody of the present invention may be manufactured by processes well known in the art, e.g., using a variety of well-known mixing, dissolving, granulating, levigating, emulsifying, encapsulating, entrapping or lyophilizing processes. The compositions may be formulated in conjunction with one or more physiologically acceptable carriers comprising excipients and auxiliaries which facilitate processing of the active compounds into preparations which can be used pharmaceutically. Proper formulation is dependent upon the route of administration chosen. Parenteral routes are preferred in many aspects of the invention.

For injection, including, without limitation, intravenous, intramusclular and subcutaneous injection, the compounds of the invention may be formulated in aqueous solutions, preferably in physiologically compatible buffers such as physiological saline buffer or polar solvents including, without limitation, a pyrrolidone or dimethylsulfoxide.

Formulations for injection may be presented in unit dosage form, e.g. in ampoules or in multi-dose containers. Useful compositions include, without limitation, suspensions, solutions or emulsions in oily or aqueous vehicles, and may contain adjuncts such as suspending, stabilizing and/or dispersing agents. Pharmaceutical compositions for parenteral administration include aqueous solutions of a water soluble form, such as, without limitation, a salt of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxyl methyl cellulose, sorbitol, or dextran. Optionally, the suspension may also contain suitable stabilizers and/or agents that increase the solubility of the compounds to allow for the preparation of highly concentrated solutions. Alternatively, the active ingredient may be in powder form for constitution with a suitable vehicle, e.g., sterile, pyrogen-free water, before use.

For oral administration, the compounds can be formulated by combining the active compounds with pharmaceutically acceptable carriers well-known in the art. Such carriers enable the compounds of the invention to be formulated as tablets, pills, lozenges, dragees, capsules, liquids, gels, syrups, pastes, slurries, solutions, suspensions, concentrated solutions and suspensions for diluting in the drinking water of a patient, premixes for dilution in the feed of a patient, and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropyl-methylcellulose, sodium carboxy-methylcellulose, and/or polyvinylpyrrolidone (PVP). If desired, disintegrating agents may be added, such as cross-linked polyvinyl pyrrolidone, agar, or alginic acid. A salt such as sodium alginate may also be used.

For administration by inhalation, the antibody of the present invention can conveniently be delivered in the form of an aerosol spray using a pressurized pack or a nebulizer and a suitable propellant. The antibody may also be formulated in rectal compositions such as suppositories or retention enemas, using, e.g., conventional suppository bases such as cocoa butter or other glycerides.

In addition to the formulations described previously, the antibody may also be formulated as depot preparations. Such long acting formulations may be administered by implantation (for example, subcutaneously or intramuscularly) or by intramuscular injection. The compounds of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

Additionally, the antibody may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the particular compound, additional stabilization strategies may be employed. Other delivery systems such as liposomes and emulsions can also be used.

A therapeutically effective amount refers to an amount of compound effective to prevent, alleviate or ameliorate cancer or cancer recurrence symptoms or AIDS. Determination of a therapeutically effective amount is well within the capability of those skilled in the art, especially in light of the disclosure herein.

For any antibody used in the methods of the invention, the therapeutically effective amount can be estimated initially from in vitro assays. Then, the dosage can be formulated for use in animal models so as to achieve a circulating concentration range that includes the effective dosage. Such information can then be used to more accurately determine dosages useful in patients.

The amount of the composition that is administered will depend upon the parent molecule included therein. Generally, the amount used in the treatment methods is that amount which effectively achieves the desired therapeutic result in mammals. Naturally, the dosages of the various compounds can vary somewhat depending upon the compound, rate of in vivo hydrolysis, etc. In addition, the dosage, of course, can vary depending upon the dosage form and route of administration.

The range set forth above is illustrative and those skilled in the art will determine the optimal dosing of the compound selected based on clinical experience and the treatment indication. Moreover, the exact formulation, route of administration and dosage can be selected by the individual physician in view of the patient's condition and of the most effective route of administration (e.g., intravenous, subcutaneous, intradermal). Additionally, toxicity and therapeutic efficacy of the antibody and other therapeutic agent described herein can be determined by standard pharmaceutical procedures in cell cultures or experimental animals using methods well-known in the art.

It is contemplated that the treatment will be given for one or more cycles until the desired clinical and biological result is obtained. The exact amount, frequency and period of administration of the compound of the present invention will vary, of course, depending upon the sex, age and medical condition of the patient as well as the severity and type of the disease as determined by the attending clinician.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs, See, e.g., Kindt et al. Kuby Immunology, 6th ed., W.H. Freeman and Co., page 91, 2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (See, e.g., Portolano et al., J. Immunol. 150:880-887, 1993; Clarkson et al., Nature 352:624-628, 1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The vector for use according to the invention is preferably a nanoparticle, a liposome, an exosome, or a viral vector, preferably an adenoviral vector, a herpetoviral vector, a lentiviral vector, a gammaretroviral vector, an adenoassociated vector (AAV), or a vector with a naked DNA plasmid. Preferably said vector is for use in the gene therapy.

The invention also provides a host cell as described above transformed with a vector as described above. The invention further provides to a cellular composition comprising at least 50% of the cells as defined above, a viral particle for medical use, preferably for use in the treatment and/or prevention of a cancer and/or AIDS, comprising the vector as described above. The invention further provides the immunoglobulin, the nucleic acid, the vector, the host cell, the cellular composition or the viral particle for use as defined above in combination with at least one therapeutic treatment.

Preferably the therapeutic treatment is selected from the group consisting of radiotherapy or chemotherapy. The immunoglobulin, the nucleic acid, the vector, the host cell, the cellular composition or the viral particle for use as defined above may also be used in combination with the anti-angiogenic agent or anti-viral agent. The invention further provides a pharmaceutical composition comprising the vector as described above or the host cell as described above or the viral particle as described above or the cellular composition as described above and at least one pharmaceutically acceptable excipient, preferably for medical use, more preferably in the treatment and/or prevention of a cancer or AIDS. Preferably the pharmaceutical composition further comprises at least one therapeutic agent, as e.g. drugs employed in AIDS treatment (such as Abacavir (Ziagen, ABC), Didanosine (Videx, dideoxyinosine, ddI), Emtricitabine (Emtriva, FTC), Lamivudine (Epivir, 3TC), Stavudine (Zerit, d4T), Tenofovir (Viread, TDF), Zalcitabine (Hivid, ddC), Zidovudine (Retrovir, ZDV or AZT), Amprenavir (Agenerase, APV), Atazanavir (Reyataz, ATV), Fosamprenavir (Lexiva, FOS), Indinavir (Crixivan, IDV), Lopinavir (Kaletra, LPV/r), Ritonavir (Norvir, RIT), Saquinavir (Fortovase, Invirase, SQV)) or cancer drugs (such as 5-fluorouracil (5-FU), 6-mercaptopurine (6-MP), Capecitabine (Xeloda®), Cytarabine (Ara-C®), Floxuridine, Fludarabine, Gemcitabine (Gemzar®), Hydroxyurea, Methotrexate, Pemetrexed (Alimta®), Taxanes: paclitaxel (Taxol®) and docetaxel (Taxotere®), Epothilones: ixabepilone (Ixempra®), Vinca alkaloids: vinblastine (Velban®), vincristine (Oncovin®), and vinorelbine (Navelbine®), Estramustine (Emcyt®), Prednisone, Methylprednisolone (Solumedrol®), Dexamethasone (Decadron®), Monoclonal antibody therapy, such as rituximab (Rituxan®) and alemtuzumab (Campath®), Non-specific immunotherapies and adjuvants (other substances or cells that boost the immune system), such as BCG, interleukin-2 (IL-2), and interferon-alfa, Immunomodulating drugs, such as thalidomide and lenalidomide (Revlimid®)). Preferably, in the vector as described above, the polynucleotide is under the control of a promoter capable of efficiently expressing said polynucleotide or polypeptide.

The vector according to the invention can comprise, in the 3'UTR of the transgene, miRNA-responsive modules which destabilise the resulting mRNA in undesirable cell types, for example in order to obtain a selective expression in the tumour stem cell compartment.

In the vector, the polynucleotide sequence, preferably a DNA sequence, is operatively tied to an appropriate sequence of control of the expression (promoter) for directing the synthesis of mRNA. As examples of promoters we can mention the immediate promoter of the early genes of cytomegalovirus (CMV), HSV thymidine kinase, early and late SV40 and retroviral LTRs. The vectors can also contain one or more selectable gene markers.

The cells of the invention also comprise "genetically engineered host cells" which are host cells that have been transduced, transformed or transfected with the polynucleotide or with the vector as described above. As examples of appropriate host cells, it can be mentioned bacterial cells, fungal and yeast cells, insect cells, plant cells and animal cells, preferably cancer cells, or cells derived from biopsies. The introduction of the previously described nucleotide molecules or vector into the host cell can be achieved using methods known to the person skilled in the art, such as, for example, calcium phosphate transfection, DEAE-dextran mediated transfection, electroporation, lipofection, microinjection, viral infection, thermal shock, cell fusion . . . the previously described polynucleotide or vector can be introduced into the cancer cells of the patient using exosomes from engineered autologous cells or artificial nanoparticles or self-complementary adenoassociated viruses.

Suitable routes of administration of the pharmaceutical composition of the invention include, for example, oral, intranasal and parenteral administration . . . . Other methods of administration include injection, viral transfer, the use of liposomes, artificial nanoparticles, exosomes from engineered autologous cells and oral intake. The exosomes from engineered autologous cells or artificial nanoparticles or self-complementary adenoassociated viruses can be functionalised if necessary in order to pass through the blood-brain barrier following intravenous administration.

In another aspect, the antibody or derivatives thereof comprises a heavy chain variable domain (VH) sequence (or a VL sequence) having at least 80%, 85%, 90%, 91%, 92%, 93%, 94%, 95%, 96%, 97%, 98%, 99%, or 100% sequence identity to an amino acid sequence selected from the group of: SEQ ID NO:1 or SEQ ID NO:2 or SEQ ID NO: 92 (or SEQ ID NO: 93).

In certain embodiments, the VH sequence (or the VL sequence) having at least 80%, 85%, 90%, 91%, 92%, 93%, 94%, 95%, 96%, 97%, 98%, or 99% identity to said: SEQ ID NO:1 or SEQ ID NO:2 or SEQ ID NO: 92 (or SEQ ID NO: 93) contains substitutions (e.g., conservative substitutions), insertions, or deletions relative to the reference sequence, but the anti-acetylated-HIV-1 integrase or the anti-acetylated histone H3 antibody comprising that sequence retains the ability to bind to the acetylated integrase or the acetylated histone.

In the present invention, "at least 80% sequence identity" means that the identity may be at least 80% or at least 85% or 90% or 95% or 100% sequence identity to referred sequences.

a) Immunoglobulins

The term "immunoglobulin" refers to any moiety capable of binding a target, in particular a member of the immunoglobulin superfamily, including T-cell receptors and antibodies. It includes any fragment of a natural immunoglobulin which is capable of binding to a target molecule, for example antibody fragments such as Fv (also called "Nanobodies") and scFv. The term "target" includes antigens, which may be targets for antibodies, T-cell receptors, or other immunoglobulin.

The term "immunoglobulin" or "antibody", in this document, also refers to antibody mimetic molecules, which even if structurally unrelated to immunoglobulins, are able to exert binding of a desired target upon artificial generation of antibody mimetic libraries. They include anticalins, DARPins, affibodies, affilins, affimers, affitins, alphabodies, avimers, fynomers, monobodies and others.

Preferably, the immunoglobulin is an antibody and the target is an antigen. "Antibody" explicitly includes antibody fragments.

Antibodies, as used herein, refer to complete antibodies or antibody fragments capable of binding to a selected target, and including Fv, ScFv, Fab' and F (ab') 2, monoclonal and polyclonal antibodies, engineered antibodies including chimeric, CDR-grafted and humanized antibodies, and artificially selected antibodies produced using phage display or alternative techniques. Small fragments, such as Fv and ScFv, possess advantageous properties for diagnostic and therapeutic applications on account of their small size and consequent superior tissue distribution. Preferably, the antibody is a single chain antibody or scFv.

The antibodies according to the invention are especially indicated for diagnostic and therapeutic applications, target validation studies and selective interference of a PTM-protein for studying of intracellular pathways. Accordingly, they may be altered antibodies comprising an effector protein such as a toxin or a label, or an enzyme. Especially preferred are labels which allow the imaging of the distribution of the antibody in vivo. Effector groups may be added prior to the selection of the antibodies by the method of the present invention, or afterwards. Also, the isolated antibodies are very useful as "macrodrugs", i.e. as protein templates with a specificity for a given PTM, that can be used as a lead to isolate chemical small molecules with similar anti PTM specificity.

Antibodies may be obtained from animal serum, or, in the case of monoclonal antibodies or fragments thereof, produced in cell culture. Recombinant DNA technology may be used to produce the antibodies according to established procedure, in bacterial or preferably mammalian cell culture. The selected cell culture system preferably secretes the antibody product.

Recombinant DNA technology may be used to improve the antibodies of the invention.

Thus, chimeric antibodies may be constructed in order to decrease the immunogenicity thereof in diagnostic or therapeutic applications. Moreover, immunogenicity may be minimized by humanising the antibodies by CDR grafting [as reviewed in European Patent Application 0 239 400 (Winter)] and, optionally, framework modification [as reviewed in international patent application WO 90/07861 (Protein Design Labs)].

More preferably, the invention employs CDR-grafted antibodies, which are preferable CDR-grafted light chain and heavy chain variable domains only. Advantageously, the heavy chain variable domain and the light chain variable domain are linked by way of a spacer group, optionally comprising a signal sequence facilitating the processing of the antibody in the host cell and/or a DNA coding for a peptide facilitating the purification of the antibody and/or a cleavage site and/or a peptide spacer and/or an effector molecule. Such antibodies are known as scFvs. Antibodies may moreover be generated by mutagenesis of antibody genes to produce artificial repertoires of antibodies. This technique allows the preparation of antibody libraries, as discussed further below; antibody libraries are also available commercially. Hence, the present invention advantageously employs artificial repertoires of immunoglobulins, preferably artificial ScFv repertoires, as an immunoglobulin source.

b) Targets

Targets are chosen according to the use to which it is intended to put the intracellular immunoglobulin selected by the method of the present invention. Thus, where it is desired to select an immunoglobulin capable of binding to a defined cellular component, such as a polypeptide, a subcellular structure or an intracellular pathogen, the whole of said component or an epitope derived therefrom may be used as a target.

Potential targets include polypeptides, which are present in the cell and, for the purpose of this invention, carry a post translational modification (PTM). Advantageously, the target is a mutant polypeptide, such as a polypeptide generated through genetic or somatic mutation, including point mutations, deletions and chromosomal translocations and is relevant for a human pathology. Such polypeptides are frequently involved in tumourigenesis or in neurodegeneration. Examples include the gene product produced by the spliced BCR-ABL genes and point mutants of the Ras oncogene or the microtubule associated protein tau. The invention is moreover applicable to all mutated oncogene products, all chromosomal translocated oncogene products (especially fusion proteins), aberrant proteins in expressed in disease, and viral or bacterial specific proteins expressed as a result of infection. The target presents a PTM. The target may be inserted into the cell, for example as described below, or may be endogenous to the cell. Where the target is endogenous, generation of the signal is dependent on the attachment of a signaling molecule to the target within the cell, or on the target itself being capable of functioning as one half of the signal-generating agent.

c) Libraries and Preselection Systems

Immunoglobulins for use in the invention may be isolated from libraries comprising artificial repertoires of immunoglobulin polypeptides. Preferably, the library used in the selection system is a SPLINT (Single Pot Library of INTrabodies) naïve library, immunized library (e.g. library from immunized animal or people affected from a particular disease) or artificial (intrabody-consensus scaffold randomized in CDRs) library of ScFvs, Nanobodies (VH or VL), antibody mimetics. SPLINT libraries are produced preferably by PCR of immunoglobulin genes (specifically cDNA from RNA) as described in Visintin et al.—"Intracellular antibodies for proteomics"—JIM (2004), or by ligation of contiguous DNA oligonucleotides. SPLINT libraries are selected directly in yeast, without need of phage display preselection or any preselection in vitro step. In an optional embodiment, the immunoglobulin may be preselected by screening against the desired PTM target, such that the method of the invention is performed with immunoglobulins which substantially are all specific for the intended PTM target. Any library preselection system may be used (possible, but not strictly necessary) in conjunction with the invention. Selection protocols for isolating desired members of large libraries are known in the art, as typified by phage display techniques. Furthermore, since the nucleotide sequence that encode the polypeptide library member is contained on a phage or phagemid vector, sequencing, expression and subsequent genetic manipulation is relatively straightforward. One particularly advantageous approach has been the use of scFv phage-libraries (Huston et al., 1988, Proc. Natl. Acad. Sci U.S.A, 85: 5879-5883; Chaudhary et al. (1990) Proc. Natl. Acad. Sci U.S.A, 87: 1066-1070; McCafferty et al. (1990) supra; Clackson et al. (1991) supra; Marks et al. (1991) supra; Chiswell et al. (1992) Trends Biotech., 10: 80; Marks et al. (1992) supra). Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys, supra), which are incorporated herein by reference. Alternative library selection technologies include bacteriophage lambda expression systems, which may be screened directly as bacteriophage plaques or as colonies of lysogens, both as previously described (Huse et al. (1989) Science, 246: 1275; Caton and Koprowski (1990) Proc. Natl. Acad. Sci. U.S.A, 87; Mullinax et al. (1990) Proc. Natl. Acad. Sci. U.S.A, 87: 8095; Persson et al. (1991) Proc. Natl. Acad. Sci. U.S.A, 88: 2432) and are of use in the invention. Other screening systems rely, for example, on direct chemical synthesis of library members. Other systems for generating libraries of polypeptides or nucleotides involve the use of cell-free enzymatic machinery for the in vitro synthesis of the library members.

Alternative display systems which are not phage-based, such as those disclosed in WO95/22625 and WO95/11922 (Affymax) use the polysomes to display polypeptides for selection. An alternative to the use of phage or other cloned libraries is to use nucleic acid, preferably RNA, derived from the spleen of an animal which has been immunised with the selected target. RNA thus obtained represents a natural library of immunoglobulins.

d) Delivery of Immunoglobulins and Targets to Cells

The present invention provides an assay for intracellular antibodies which is conducted essentially intracellularly, or in conditions which mimic the intracellular environment, preferably the cytoplasmic environment. In order to introduce immunoglobulins and target molecules into an intracellular environment, cells are advantageously transfected with nucleic acids which encode the immunoglobulins and/or their targets. Nucleic acids encoding immunoglobulins and/or targets can be incorporated into vectors for expression. As used herein, vector (or plasmid) refers to discrete elements that are used to introduce heterologous DNA into cells for expression thereof. Selection and use of such vehicles are well within the skill of the artisan. Many vectors are available, and selection of appropriate vector will depend on the intended use of the vector, the size of the nucleic acid to be inserted into the vector, and the host cell to be transformed with the vector. Each vector contains various components depending on its function and the host cell for which it is compatible. The vector components generally include, but are not limited to, one or more of the following: an origin of replication, one or more marker genes, an enhancer element, a promoter, a transcription termination sequence and a signal sequence.

Moreover, nucleic acids encoding the immunoglobulins and/or targets according to the invention may be incorporated into cloning vectors, for general manipulation and nucleic acid amplification purposes.

Both expression and cloning vectors generally contain nucleic acid sequence that enable the vector to replicate in one or more selected host cells. Typically in cloning vectors, this sequence is one that enables the vector to replicate independently of the host chromosomal DNA, and includes origins of replication or autonomously replicating sequences. Such sequences are well known for a variety of bacteria, yeast and viruses.

Advantageously, an expression and cloning vector may contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e. g. ampicillin, neomycin, methotrexate or tetracycline, complement auxotrophic deficiencies, or supply critical nutrients not available from complex media. As to a selective gene marker appropriate for yeast, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, ADE2 or HIS3 gene. Since the replication of vectors is conveniently done in *E. coli*, an *E. coli* genetic marker and an *E. coli* origin of replication are advantageously included. These can be obtained from *E. coli* plasmids, such as pBR322, BluescriptC) vector or a pUC plasmid, e. g. pUC18 or pUC19, which contain both an *E. coli* replication origin and an *E. coli* genetic marker conferring resistance to antibiotics, such as ampicillin. Suitable selectable markers for mammalian cells are those that enable the identification of cells expressing the desired nucleic acid, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked nucleic acid. Amplification is the process by which genes in greater demand for the production of a protein critical for growth, together with closely associated genes which may encode a desired protein, are reiterated in tandem within the chromosomes of recombinant cells. Increased quantities of desired protein are usually synthesised from thus amplified DNA. Expression and cloning vectors usually contain a promoter that is recognised by the host organism and is operably linked to the desired nucleic acid. Such a promoter may be inducible or constitutive. The promoters are operably linked to the nucleic acid by removing the promoter from the source DNA and inserting the isolated promoter sequence into the vector. Both the native promoter sequence and many heterologous promoters may be used to direct amplification and/or expression of nucleic acid encoding the immunoglobulin or target molecule. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Promoters suitable for use with prokaryotic hosts-include, for example, the p-lactamase and. lactose promoter systems, alkaline phosphatase, the tryptophan (trp) promoter system and hybrid promoters such as the tac promoter. Preferred expression vectors are bacterial expression vectors which comprise a promoter of a bacteriophage such as phage Φx or T7 which is capable of functioning in the bacteria. Suitable promoting sequences for use with yeast hosts may be regulated or constitutive and are preferably derived from a highly expressed yeast gene, especially a *Saccharomyces cerevisiae* gene. Thus, the promoter of the TRP1 gene, the ADHI or ADHII gene, the acid phosphatase (PH05) gene, a promoter of the yeast mating pheromone genes coding for the a- or a-factor or a promoter derived from a gene encoding a glycolytic enzyme such as the promoter of the enolase, glyceraldehyde-3phosphate dehydrogenase (GAP), 3-phospho glycerate kinase (PGK), hexokinase, pyruvate decarboxylase, phosphofructokinase, glucose-6-phosphate isomerase, 3phosphoglycerate mutase, pyruvate kinase, triose phosphate isomerase, phosphoglucose isomerase or glucokinase genes, the *S. cerevisiae* GAL 4 gene, the *S. pombe* nmt 1 gene or a promoter from the TATA binding protein (TBP) gene can be used. Furthermore, it is possible to use hybrid promoters comprising upstream activation sequences (UAS) of one yeast gene and downstream promoter elements including a functional TATA box of another yeast gene, for example a hybrid promoter including the UAS (s) of the yeast. PH05 gene and downstream promoter elements including a functional TATA box of the yeast GAP gene (PH05-GAP hybrid promoter). A suitable constitutive PH05 promoter is e. g. a shortened acid phosphatase PH05 promoter devoid of the upstream regulatory elements (UAS) such as the PH05 (−173) promoter element starting at nucleotide-173 and ending at nucleotide-9 of the PH05 gene. Gene transcription from vectors in mammalian hosts may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the actin promoter or a very strong promoter, e. g. a ribosomal protein promoter, and from promoters normally associated with immunoglobulin sequences. Transcription of a nucleic acid by higher eukaryotes may be increased by inserting an enhancer sequence into the vector. Eukaryotic expression vectors will also contain sequences necessary for the termination of transcription and for stabilising the mRNA. Such sequences are commonly available from the 5' and 3'untranslated regions of eukaryotic or viral DNAs or cDNAs. These regions contain nucleotide segments transcribed as polyadenylated fragments in the untranslated portion of the mRNA encoding the immunoglobulin or the target.

Particularly useful for practising the present invention are expression vectors that provide for the transient expression of nucleic acids in mammalian cells. Transient expression usually involves the use of an expression vector that is able to replicate efficiently in a host cell, such that the host cell accumulates many copies of the expression vector, and, in turn, syntheses high levels of the desired gene product. Construction of vectors according to the invention may employ conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing gene product expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe which may be based on a sequence provided herein. Those skilled in the art will readily envisage how these methods may be modified, if desired. Immunoglobulins and/or targets may be directly introduced to the cell by microinjection, or delivery using vesicles such as liposomes which are capable of fusing with the cell membrane. Viral fusogenic peptides are advantageously used to promote membrane fusion and delivery to the cytoplasm of the cell.

e) Generation of a Signal

In the method of the present invention, a signal is advantageously generated by the interaction of two molecules, brought together by the binding of the immunoglobulin to the target. The signal generated will thus be dependent on the nature of the molecules used in the method of the invention. In a first embodiment, the signal-generation molecules may be fluorophores. Particularly preferred are fluorescent molecules which participate in energy transfer (FRET).

In a FRET assay, the fluorescent molecules are chosen such that the excitation spectrum of one of the molecules (the acceptor molecule) overlaps with the emission spectrum of the excited fluorescent molecule (the donor molecule). The donor molecule is excited by light of appropriate intensity within the donor's excitation spectrum. The donor then emits some of the absorbed energy as fluorescent light and dissipates some of the energy by FRET to the acceptor fluorescent molecule. The fluorescent energy it produces is quenched by the acceptor fluorescent molecule. FRET can be manifested as a reduction in the intensity of the fluorescent signal from the donor, reduction in the lifetime of its excited state, and re-emission of fluorescent light at the longer wavelengths (lower energies) characteristic of the acceptor. When the donor and acceptor molecules become spatially separated, FRET is diminished or eliminated. Suitable fluorophores are known in the art, and include chemical fluorophores and fluorescent polypeptides, such as GFP and mutants thereof which fluoresce with different wavelengths or intensities (see WO 97/28261). Chemical fluorophores may be attached to immunoglobulin or target molecules by incorporating binding sites therefor into the immunoglobulin or target molecule during the synthesis thereof.

Preferably, however, the fluorophore is a fluorescent protein, which is advantageously GFP or a mutant thereof. GFP and its mutants may be synthesised together with the immunoglobulin or target molecule by expression therewith as a fusion polypeptide, according to methods well known in the art. For example, a transcription unit may be constructed as an in-frame fusion of the desired GFP and the immunoglobulin or target, and inserted into a vector as described above, using conventional PCR cloning and ligation techniques.

In a second embodiment, the immunoglobulin and target polypeptides are associated with molecules which give rise to a biological signal. Preferred are polypeptide molecules, which advantageously interact to form a transcription factor, or another regulatory molecule, which modulates gene expression within the cell, and in particular, the expression of a selectable gene. Suitable selectable markers for yeast are, for example, those conferring resistance to antibiotics G418, hygromycin or bleomycin, or provide for prototrophy in an auxotrophic yeast mutant, for example the URA3, LEU2, LYS2, TRP1, ADE2 or HIS3 gene. Exemplary transcription factor molecules have been described in the literature, for example by Fields & Song, (1989) Nature 340: 245-246, which is incorporated herein by reference. In a preferred embodiment, the immunoglobulin molecule is expressed as fusion protein with the activation domain of the HSV 1 VP 16 molecule. This transcription factor domain is capable of upregulating gene transcription from a promoter to which it is bound through a DNA binding activity. The latter is provided by the DNA-binding domain of the *E. coli* LexA polypeptide, which is expressed as a fusion protein with the target polypeptide.

The biological signal may be any detectable signal, such as the induction of the expression of a detectable gene product. Examples of detectable gene products include bioluminescent polypeptides, such as luciferase and GFP, polypeptides detectable by specific assays, such as B-galactosidase and CAT, and polypeptides which modulate the growth characteristics of the host cell, such as enzymes required for. metabolism such as HIS3, or antibiotic resistance genes such as G418. In a preferred aspect of the invention, the signal is detectable at the cell surface. For example, the signal may be a luminescent or fluorescent signal, which is detectable from outside the cell and allows cell sorting by FACS or other optical sorting techniques. Alternatively, the signal may comprise the expression of a cell surface marker, such as a CD molecule, for example CD4 or CD8, which may itself be labelled, for example with a fluorescent group, or may be detectable using a labelled antibody.

In this embodiment, the invention permits the screening of entire libraries of intracellular antibodies such as SPLINT, to isolate the antibodies which bind to the desired PTM antigen. Use of selectable markers influencing growth, as well as of enzymatic signals such as those originating by beta-galactosidase expression, enable an entire library to be selected for the isolation of anti PTM antibodies capable of functioning intracellularly. Also, optical sorting, such as FACS, enables an entire library to be panned and selects for antibodies which are capable of functioning intracellularly and bind the desired target.

Adapting Tethered Catalysis baits to IACT represents not only a novel and unprecedented extension of the IACT system, but also the first answer to the problem of having a general platform to select intracellular antibodies against PTMs. Currently, no technology is able to generally select intrabodies against a desired PTM-antigen. At the same way, Tethered Catalysis has never been used for selection of antibodies, let alone of intrabodies. Furthermore, a proof of principle is not obvious, since antibodies have never been proven to be selectable (in vivo and in vitro) by this method, and moreover, their production by these means, was never shown to be functional in cells. Inventors provide the demonstration of a PTM-specific protein silencing in cells, with an intrabody selected, by this invention, in a generic way and not with an ad hoc, occasional, antibody. Moreover, applications coming from this new system are intended not to find the natural partners of a PTM, but to select intracellular antibodies for protein interference, drug development, cell studies, development of new biotechnologies.

P.I.S.A. platform is able to select intrabodies against native, post-translationally modified proteins, that fold as full-length proteins (or structurally folded domains) in their natural intracellular environment, concomitantly to their PT-Modification. Selection occurs without any manipulation of the antigen. On the other hand, other selection platforms (for selection of antibodies in vitro), use either purified antigens or peptides that need to be modified in vitro after their manipulation to incorporate the desired target PTM. However, these methods are not suitable for the selection of anti PTM antibodies, and the only general way that the current state of the art allows for is the chemical synthesis of a peptide antigen incorporating the PTM. Thus, current methods give rise only to anti peptide antibodies, at best, with the well known limitations of anti peptide antibodies that most often react poorly with the native structured protein. Thus, purification of a native protein comprising the target PTM from its unmodified protein counterpart, is practically impossible, or very difficult. In this invention, this difficulty is overcome because the cell carries out the PTM, on the folded protein. Moreover, antibodies selected with existing methods have thus no guarantee to be useful in functional studies as intrabodies, both because they were selected in vitro, both because targeted epitope could not present a native folding. On the contrary, PISA antibodies are ideal for PTM-selective and PTM-specific protein interference and cellular studies, and can be used in in vitro assays as well. One very surprising and unexpected feature of the present invention is the source of the antibody library. It was totally unexpected, and a priori not predictable, that a library of naive antibody genes (i.e. not derived from a specifically PTM-immunized animal or human individual) would allow for the successful isolation and selection of anti PTM antibodies. Indeed, all other methods for PTM antibody isolation rely on an immunization step, or on ad hoc recombinant libraries enriched in anti PTM specificities. Here follows a concise comparison table of different methods for the selection of antibodies against PTMs.

TABLE I

| Selection Method | Type of Selection | Manipulation/ Purification of Antigen? | PTM, catalysis | Antibody folding |
|---|---|---|---|---|
| Phage Display | In vitro | Yes | Post-purification, in vitro | Periplasmic space of bacteria |
| Yeast Display | In vitro | Yes | Post-purification, in vitro | Biosynthetic-Secretory Pathway |
| Immunization of animals | Extra-cellular | Yes | Post-purification, in vitro | Biosynthetic-Secretory Pathway |
| PISA | In vivo | No | Native, in vivo | Cytoplasm |

Table 1 - Comparison between different antibody selection technologies. PISA is the only platform that is able to select intrabodies in vivo without whatsoever manipulation of the PTM antigen, which folds in the cell, in its native form.

PISA technology therefore allows a selection in vivo, without needing to manipulate the antigen or to chemically synthetizing it, of PTM in the native protein context.

The selection provides both the antibody protein and the gene that encodes it, so that all downstream applications are facilitated. Selected antibodies are functionally validated to work in cells. The technology provides streamlining the procedures, so it is a general method that can generate a pipeline of anti PTM antibodies.

PTM-specific intrabodies strongly differ from the new class of inhibitors targeting bromodomains (BET inhibitors (Filippakopoulos, Nature 2010)), which are instead acetyl-lysine binding modules ("epigenetic readers" (Zeng et al. FEBS Letters 2002)). Instead, acetylation-specific intrabodies, such as those described in this invention, do not target the epigenetic readers, but, rather, the epigenetic "word" (i.e. the acetyl-lysine on the target protein). They could be used, for instance, to selectively target the recognized PTM-protein pool for degradation (Melchionna et al—JMB 2007). Substantially, at the moment, there is no possibility of interfering specifically with a single acetylated protein. All existing purported inhibitors of "acetylated proteins", can only affect very upstream molecules, causing a massive reduction in global acetylation patterns. PISA technology, instead, provides a virtually unlimited source of orthogonal molecular tools for direct PTM-specific interference, suitable for functional in vivo studies.

PISA intrabodies also can be employed to solve totally different biological questions with respect to commonly used HDAC (Falkenberg et al.—Nature Reviews Drug Discovery 2014) and HAT inhibitors (Di Martile et al—Oncotarget 2016). The novel and most important achievement is that with PISA it is now possible to target the PTM protein directly, without simultaneously inhibiting the enzyme and all of its target substrates. Moreover, PISA allows to target the precise PTM epitope of a protein, which can be a point of contact for dedicated protein-protein interactions (a link of an intracellular protein network). For instance, the hydroxamic class of HDAC inhibitors, of which Vorinostat (SAHA) (Zhang et al.—The Journal of investigative dermatology 2005) is the first developed and approved by the US FDA for clinical use, generally have common structural characteristics and are composed of chemical groups that interact with three relatively conserved regions of the catalytic pocket of all HDACs (common to all of them). PISA antibodies have thus a much greater specificity and selectivity.

The present invention will be described by means of non-limiting examples referring to the following figures:

FIG. 1: PISA Tethered Catalysis Baits

In tethered catalysis baits used in PISA technology, the target antigen is fused to the enzyme that naturally catalyzes its PTM (e.g. HAT, Histone Acetyl Tranferase) in vivo. This fusion generates a constitutive, stable, in cis post-translational modification on the target protein. The antigen/enzyme construct is moreover fused at the c-term of LexA DNA binding domain, and at the N-term of a tag such as hemagglutinin (HA), forming in this way the "screening bait". To discriminate intrabodies binding the PTM specifically, a panel of mutated baits is used. In particular, a bait that is identical to the screening bait but for a point mutation in the acetylating enzyme is used. This mutation inactivates the enzyme, causing the target protein not to be acetylated anymore. An anti-acetyl intrabody (or anti-PTM intrabody) will thus bind the screening bait but not the mutated bait.

FIG. 2: Western Blot analysis to check expression and acetylation status in yeast. a) Screening Bait LexA-Integrase-p300 wt-HA and LexA-Integrase-p300mut-HA were immunoprecipitated from yeast protein extract after expression of bait plasmids, and blotted for HA tag (hemagglutinin). Membrane was then stripped and re-blotted with an anti-Acetyllysine pan-reactive antibody (CellSignal) to confirm acetylation occurs using WT construct only; b) Anti-HA blot for deletion control construct; c) LexA-Integrase bait was detected with a specific anti-Integrase antibody (left), which is able to recognize the full-length chimeric contructs as well. If stripped and blotted for Acetilated Lysines, no acetylation is shown without the acetyl-transferase (HAT) C-term fusion.

Figure 3:
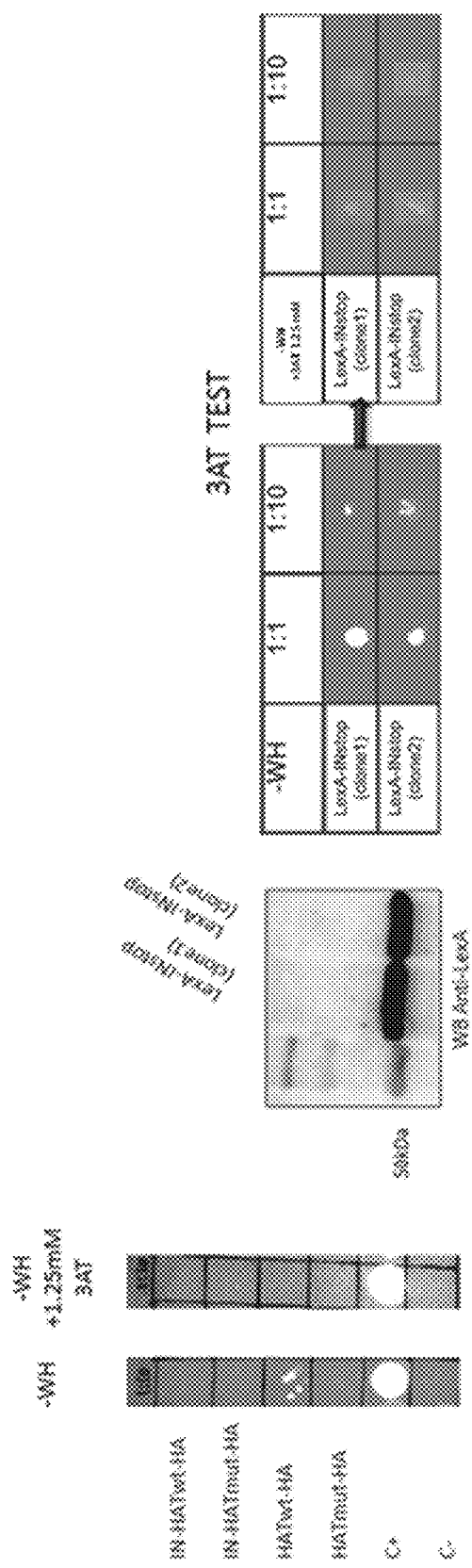

FIG. 3: Auto-Activation Test for Integrase Baits. Most of baits present no auto-activation if plated on a His-free medium (−WH). 1.25 mM of 3-AT was needed to turn off non-specificHis3 expression in LexA-HATwt and LexA-Integrase baits. LacZ marker auto-activation was also checked.

Figure 4:
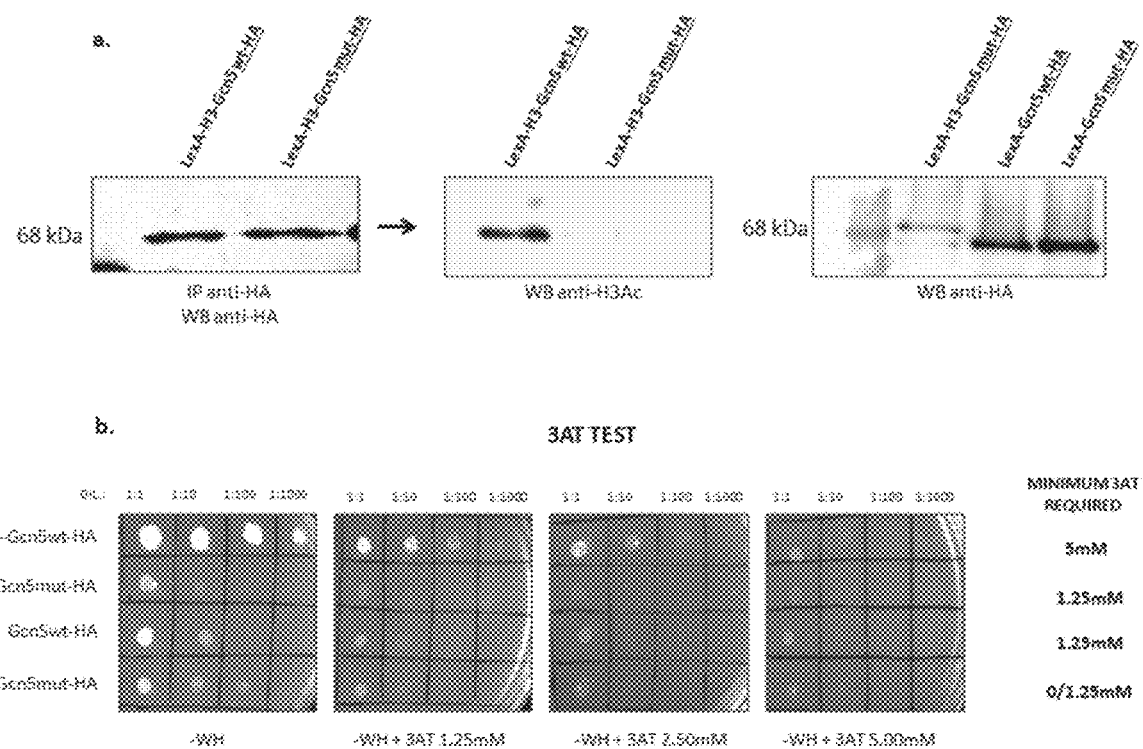

FIG. 4: Western Blot and 3-AT test for H3 baits. a) As done for IN baits, H3 screening bait (left) and controls (right) are analyzed by WB to check expression and specific acetylation. b) 3-AT test reveals that minimum concentration needed for LexA-H3-Gcn5 wt-HA (screening bait) is 5 mM. Other 3-AT concentration used for control baits are shown.

Figure 5:
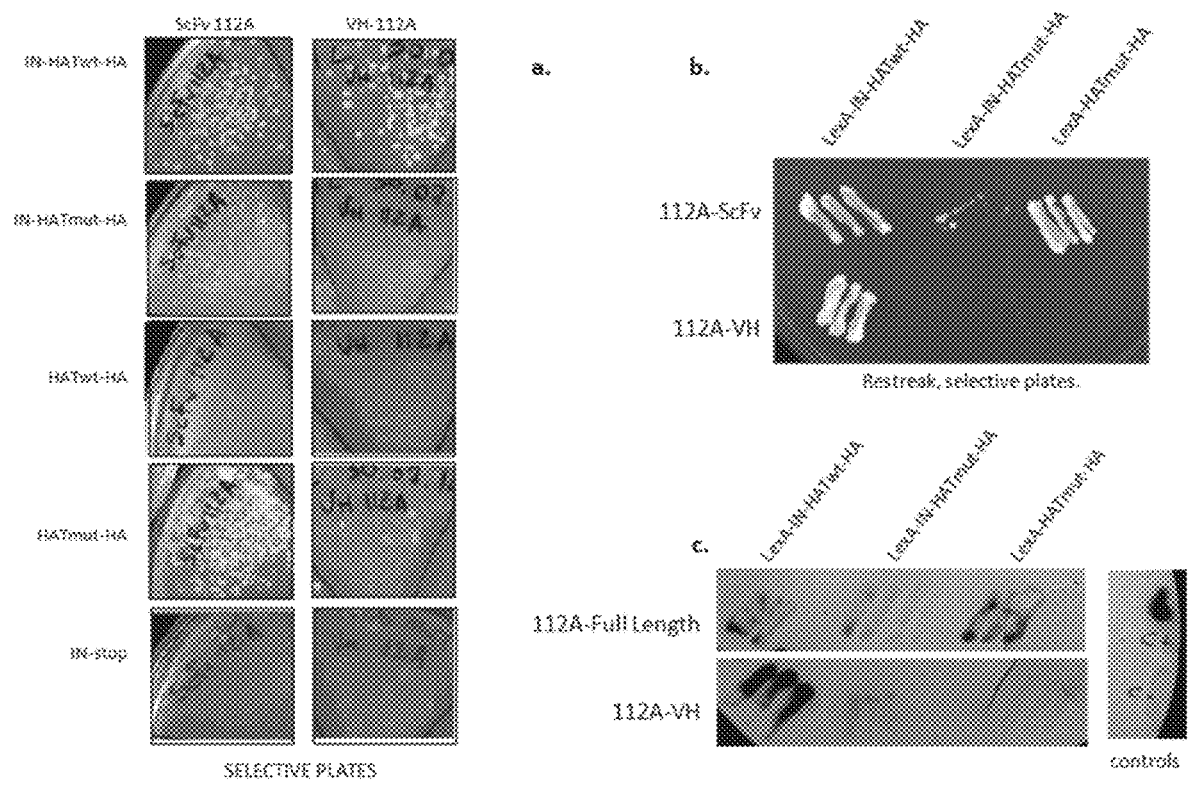

FIG. 5: VH-112A domain intrabody is specific for Acetylated Integrase and it is not able to interact with non-acetylated version of the protein. a) Comparison between ScFv-112A and VH-112A intrabodies. The ScFv version of the selected prey cross-reacts with LexA-p300mut-HA. By using its VH domain instead, undesired activity completely disappears. Notably, 112A in both versions is NOT able to interact with non-acetylated integrase (IN-stop bait is not acetylated, see above). −WL (non-selective) plates are equally populated by cells; b) Single yeast colonies were restreaked from −WL plates to −WHL plates to further confirm specific growth. Remarkable is the absence of growth in all baits but the main one. c) Clones grown on −WL (non-selective) were used for beta-gal filter assay. Very clearly, the same interaction pattern is confirmed also with the second selection marker.

Figure 6:
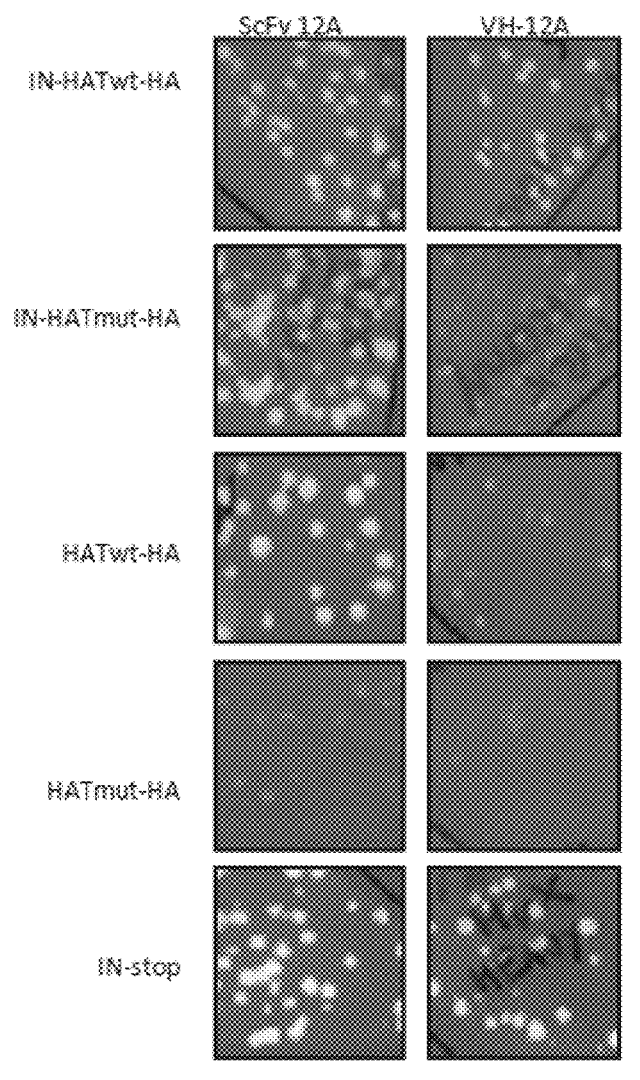

FIG. 6: In Vivo Epitope Mapping comparison between ScFv-12A and VH-12A. Splitting VH from VL improves antibody specificity and does not change its ability to bind Integrase bait. Data suggest VH12A has a preferential binding for Acetylated Integrase if compered to its ScFv version.

Figure 7:
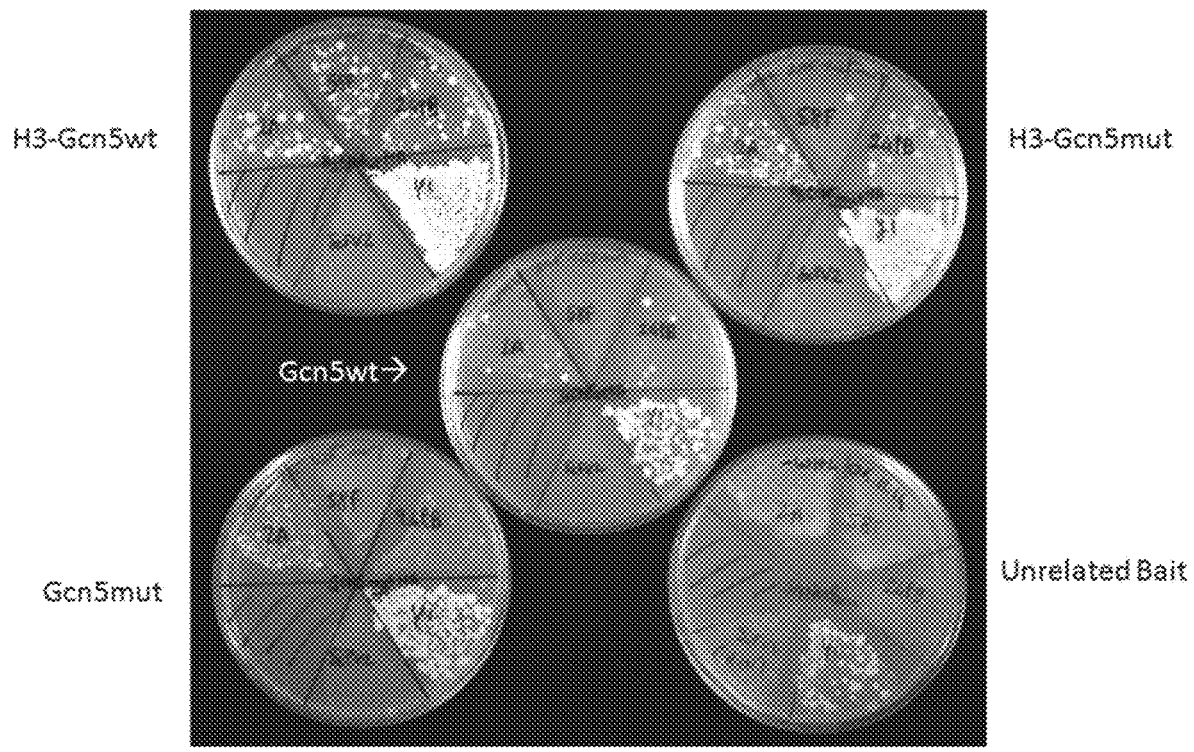

FIG. 7: Secondary screening of LexA-H3-Gcn5 wt-HA. −WHL+3AT plates have been divided in sectors. Each plate represents one different bait, while each sector indicate the prey partner. As showed, ScFv-58F is the only intrabody that is able to grow in presence of the screening bait only.

Figure 8:
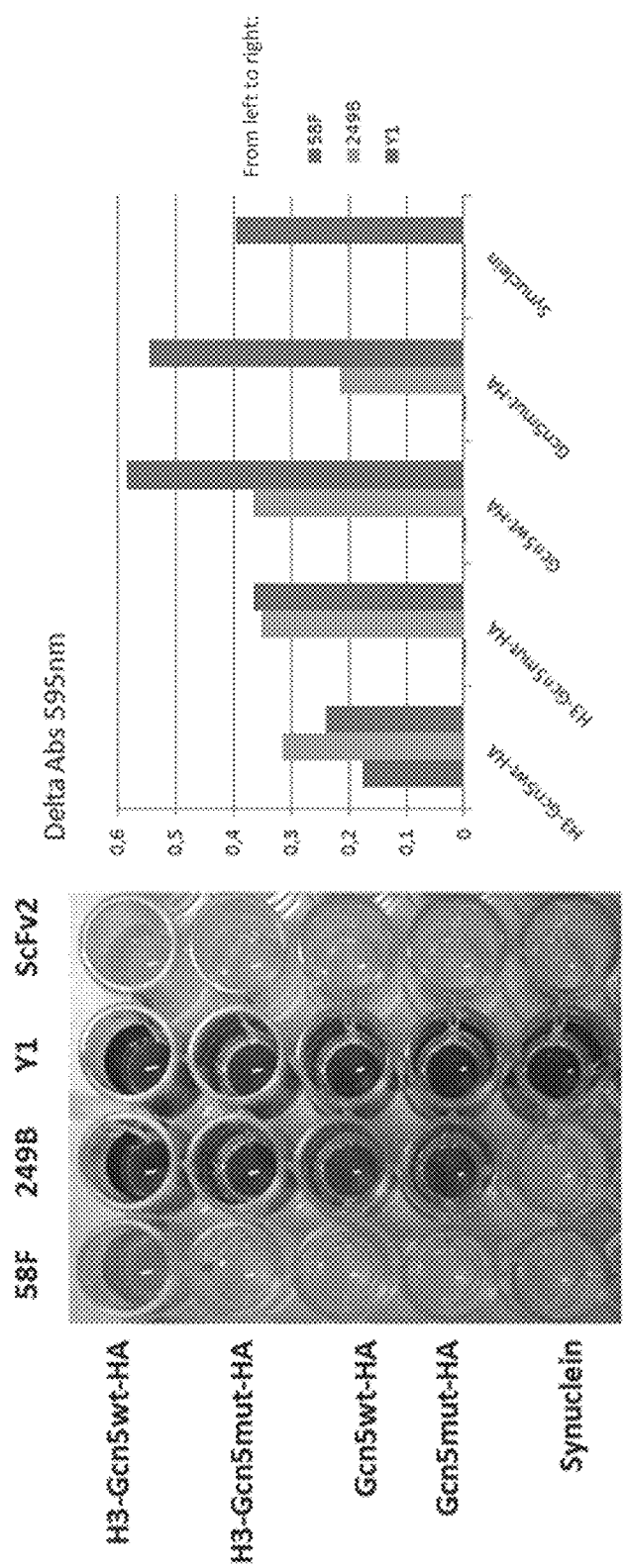

FIG. 8: Beta-galactosidase liquid assay: Same amount of cell from non-selective medium was lysed using zymolase and freeze/thaw cycles. After that, cleared extracts were assessed for Beta-Gal presence using X-gal. As evident, 58F well turns blue only when using the main bait. Y1 represents an anti-LexA intrabody (positive control), whilst ScFv2 is the negative control, on which Absorbance results are normalized.

Figure 9:
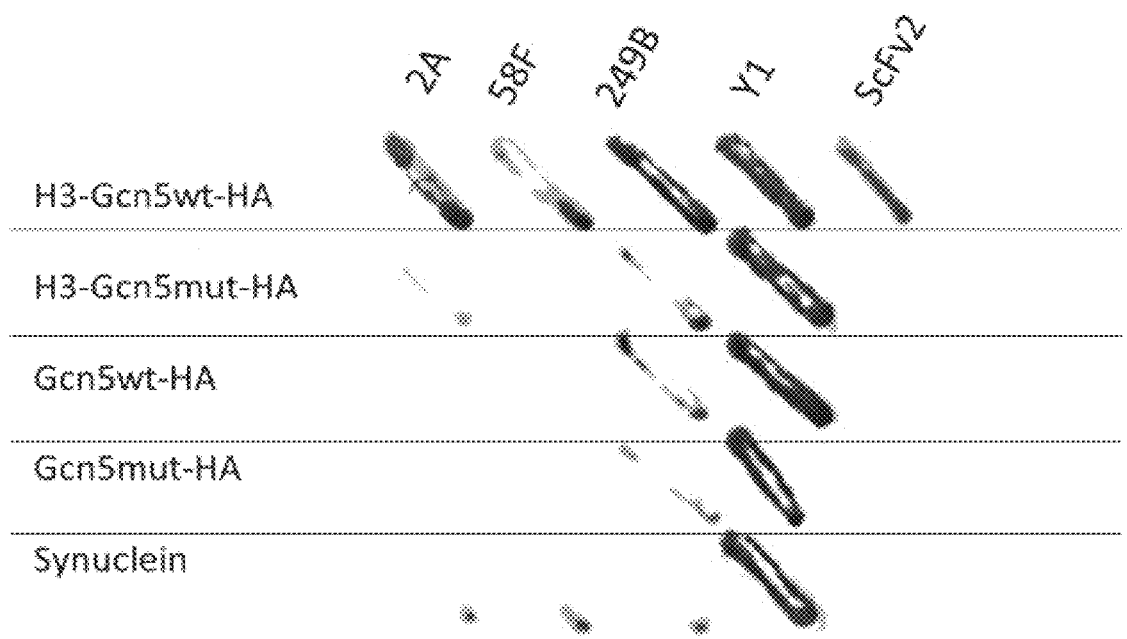

FIG. 9: Beta gal filter assay. Classic filter assay made from −WL yeasts showing same results obtained with the semi-quantitative liquid assay. Blue color of the screening bait/scfv2 couple is due to sensible autoactivation level of the bait (5 mM). Liquid assay was in fact preferred to this, since it minimizes "blue background".

Figure 10:
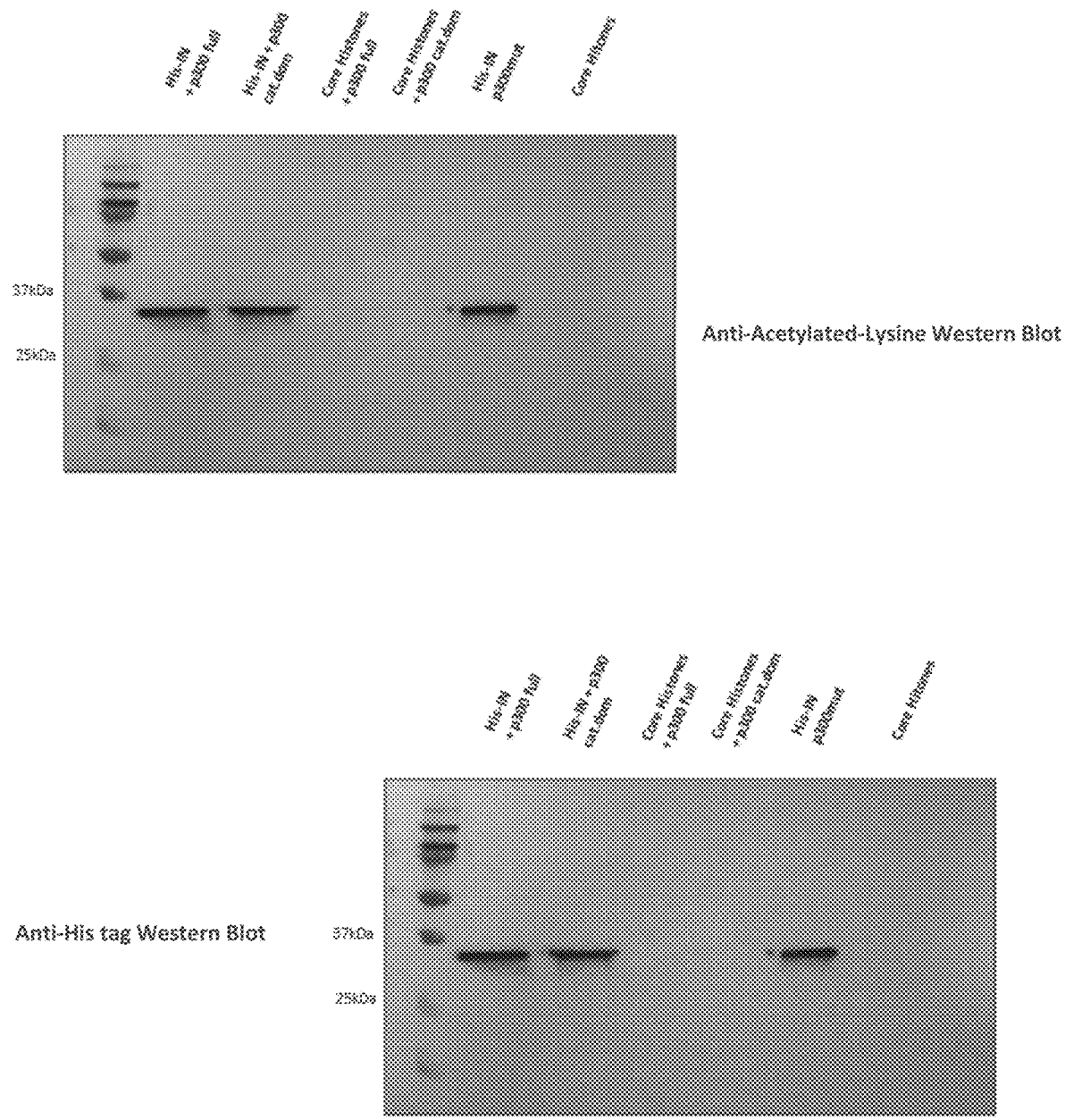

FIG. 10: In vitro acetylation of His-Integrase, WB analysis. Upper blot uses anti-AcLys to confirm acetylation occurred only when WT enzyme was used. Reaction was functional both with full length p300 and p300 catalytic domain. Positive control is represented from purified histon cores. Same samples were targeted with anti-his antibody to show presence of purified integrase (lower image).

Figure 11:
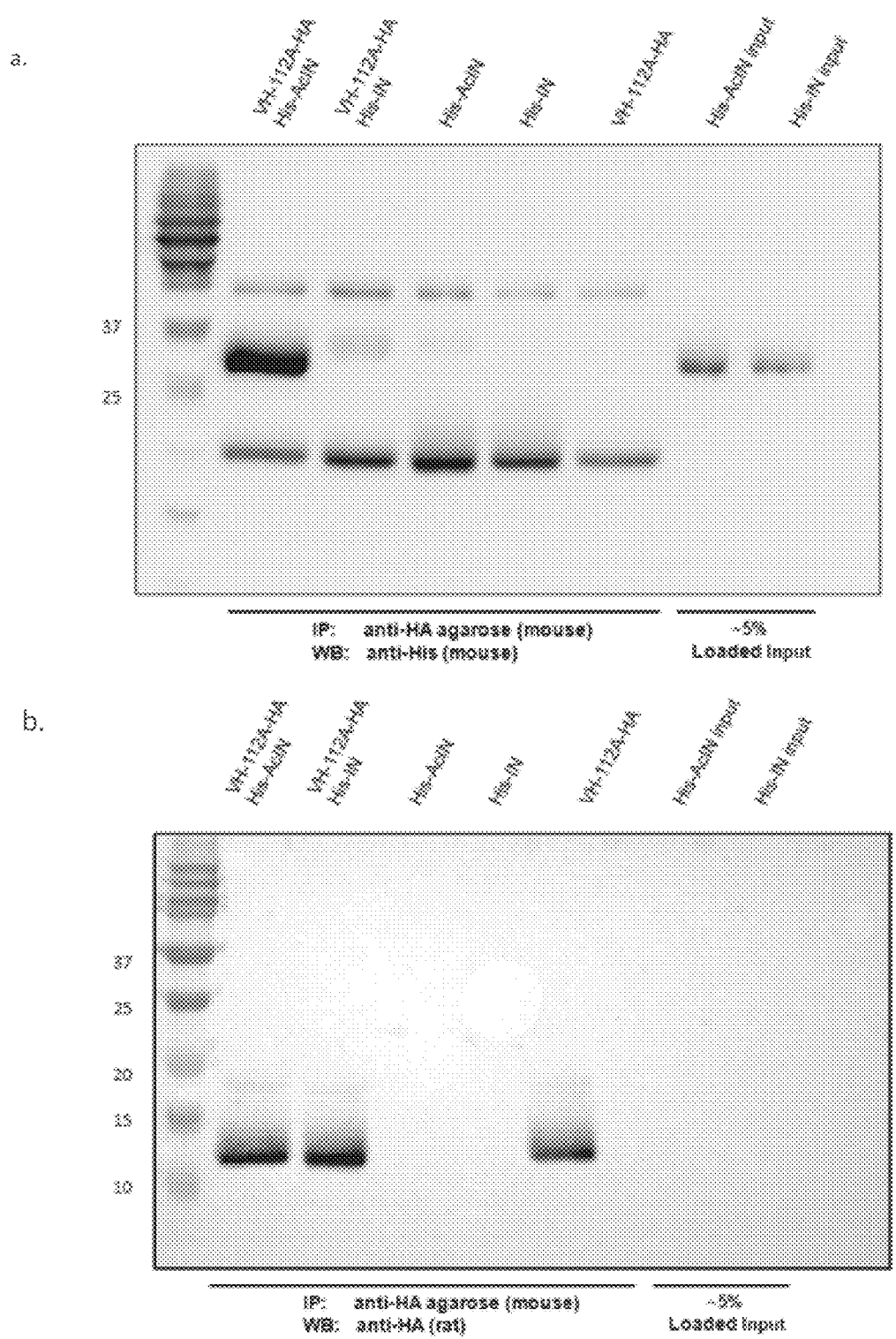

FIG. 11: Co-Immunoprecipitation of Ac-Integrase using VH-112A intrabody. (a) anti-His W.B. of anti-HA Immunoprecipitates. VH-112A can immunoprecipitate Acetyl-Integrase only. Additional 15 kDa and 50 kDa bands are mouse immunoglobulins targeted by anti-mouse-HRP secondary antibody. (b) anti-HA blot of anti-HA immunoprecipitates, to check presence of the intrabody. Same experiments were conducted also by incubating His-IN with purified HATmut with no difference in results.

Figure 12:
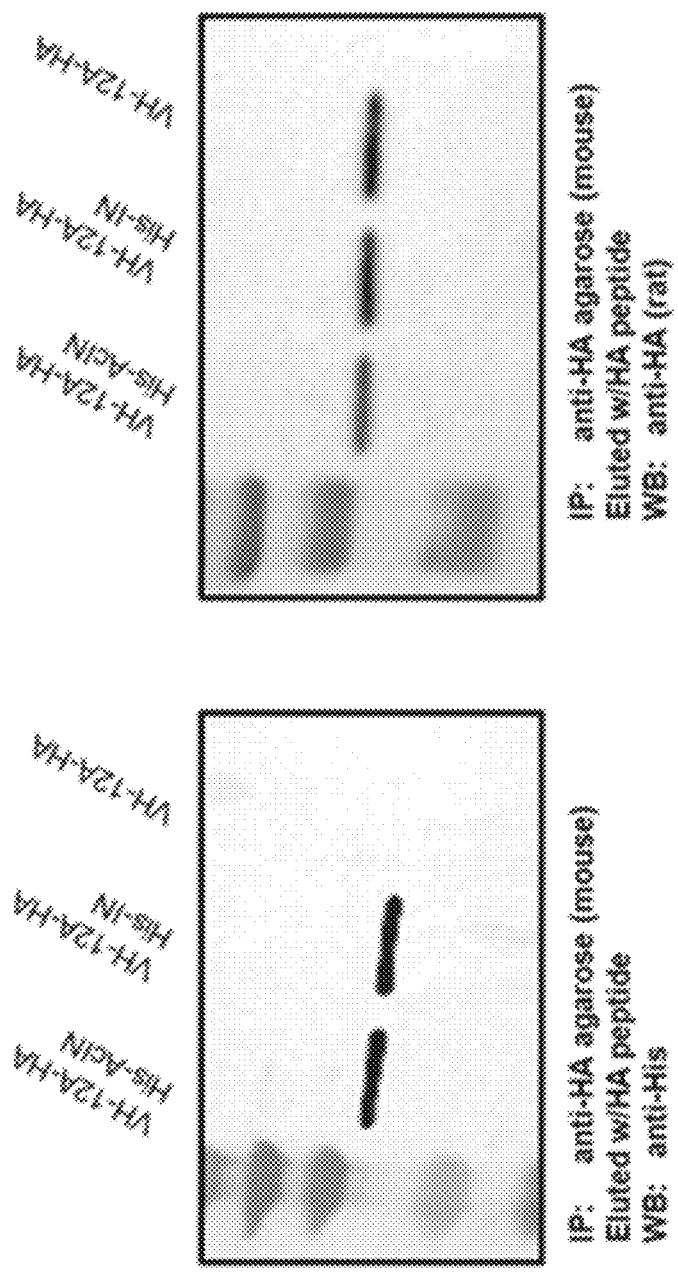

FIG. 12: Co-IP using anti-Integrase VH12A-HA. Experimental protocol is the same used with VH-112A-HA, except that final anti-HA resin was not boiled directly, but 1 mg/mL of HA peptide was used to displace the immunoprecipitated complex. Eluted surnatant thus, did not contain anti-HA antibodies and was analysed both with anti-HA and anti-his WB. His-AcIN and His-IN cannot be precipitated by resin alone, as shown in previous experiment.

FIG. 13: ELISA using VH-12A-HA and VH-112A-HA. In vitro detection of acetylated integrase was possible using VH-112A-HA antibody. VH-112A-HA instead recognizes both Integrase forms, but with more specificity for the non-acetylated one.

Figure 14:
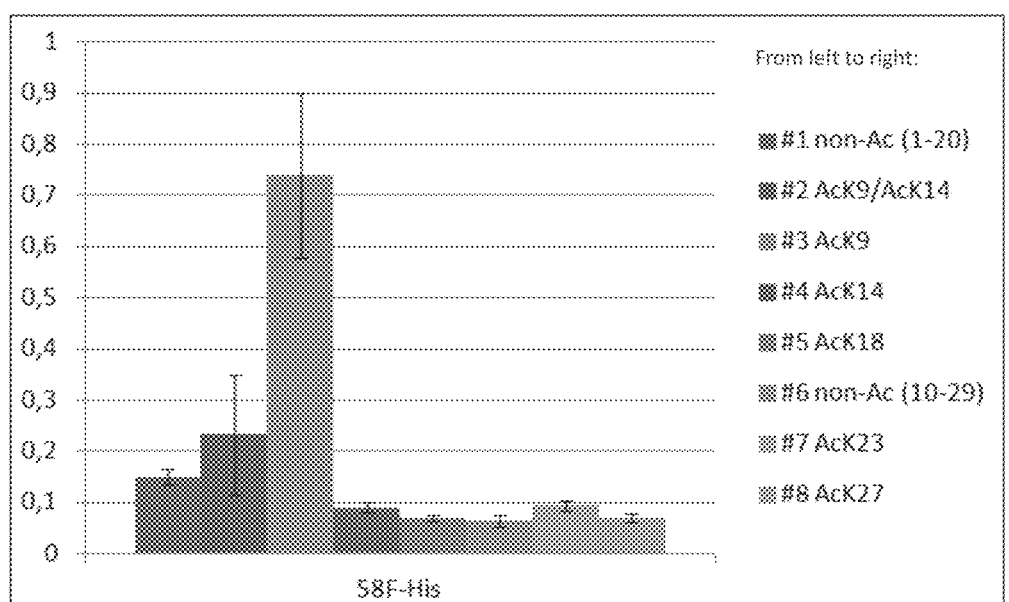

FIG. 14: ELISA with His-ScFv-58F. ScFv58F was expressed in bacteria with a His6x C-term tag and purified with TALON cobalt-based resin in a TBS buffer. Purified intrabody was then used as primary antibody for ELISA assay with eight different acetylated or non-acetylated yeast Histone peptides (coating, listed in the figure) to assess in vitro binding and targeted epitope. 58F-His was detected with a mouse anti-His antibody and subsequently with an anti-mouse HRP antibody. ScFv58F seems to target specifically AcK9 H3 peptide, with less preference for AcK9/AcK14 peptide.

FIG. 15: (a) Dot blot array of modified histone peptides to test ScFv-58F specificity. An annotated array of 384 modified histone peptides was incubated with scFv 58F, showing that scFv58F specifically binds to the Acetyl K9 variant of Histone H3 without cross-reacting with differently modified H3 peptide, nor with other histones. Two experimental replicas are shown in the Figure. The spot in the lower right part of the filter is a positive control (c-myc). (b) MODified Histone annotated array—Specificity Analysis. Data analysis performed with ActiveMotif software for the Histone MODified Annotated Array. ScFv-58F is strongly specificity for the acetylated lysine #9 of Histone H3 over other common modifications.

Figure 16:
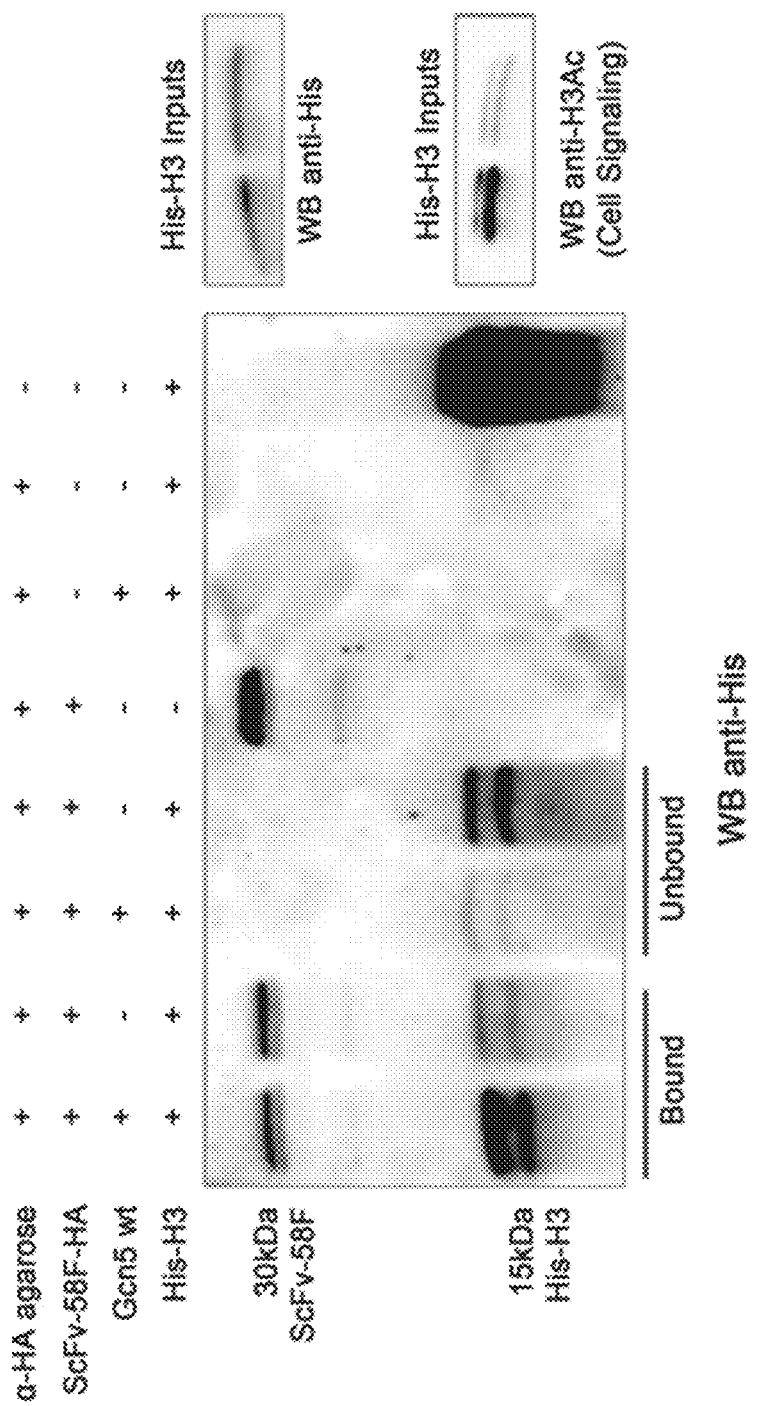

FIG. 16: Biochemical characterization and validation of anti-acetylated H3 histone intrabody ScFv-58F. Co-IP between ScFv-58F-HA and purified His-H3/HisAcH3 proteins (both expressed in E. coli, histone acetylated in vitro) using anti-HA agarose, followed by anti-HIS Western Blot. Lanes 1-2: the intrabody binds acetyl histone H3 with a strong prevalence over non acetylated H3

Figure 17:
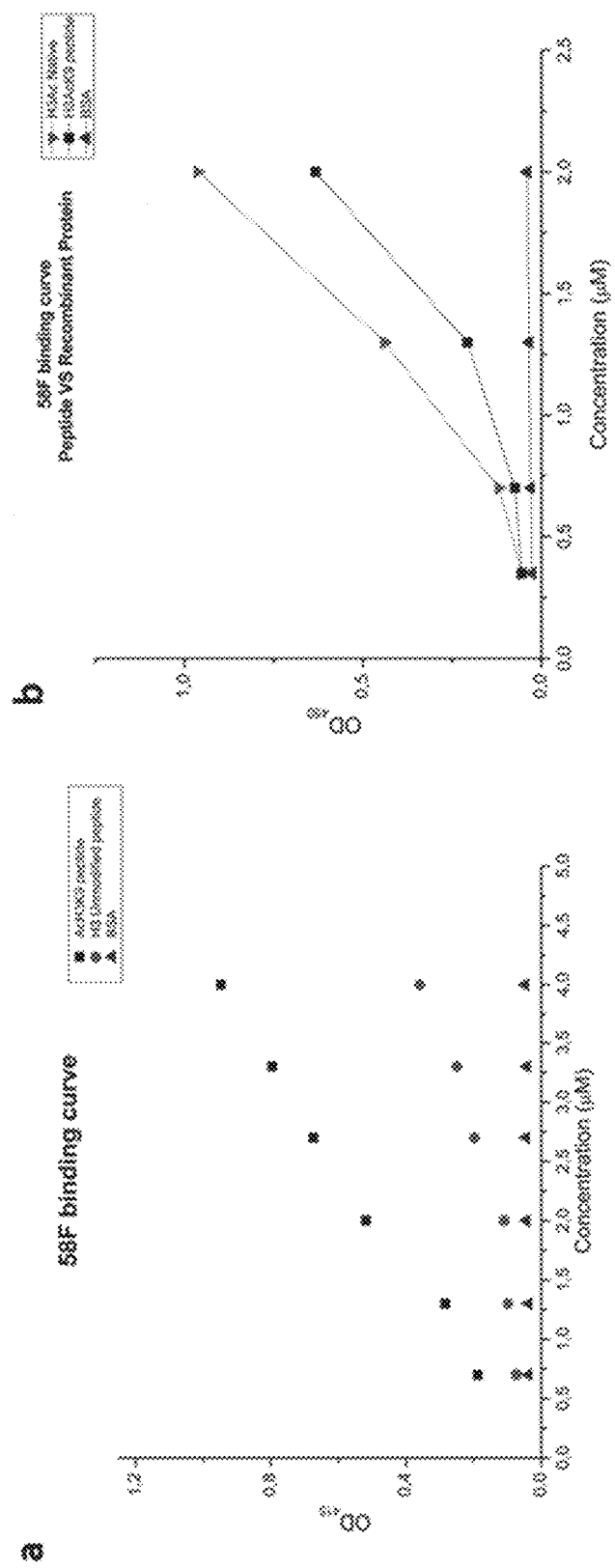

FIG. 17: ScFv-58F Binding data and specificity analysis. (a) ELISA dilution binding curve using 10 uM of acetylated (K9) or non acetylated H3 peptides coated on solid phase and different concentrations of ScFv-58F-HA as probe. (b) ELISA dilution binding curve using native acetylated H3 protein and H3AcK9 peptide, both coated on solid phase. The curves show a concentration range where ScFv-58F binds more effectively to the native acetylated protein than to the acetylated peptide.

Figure 18:
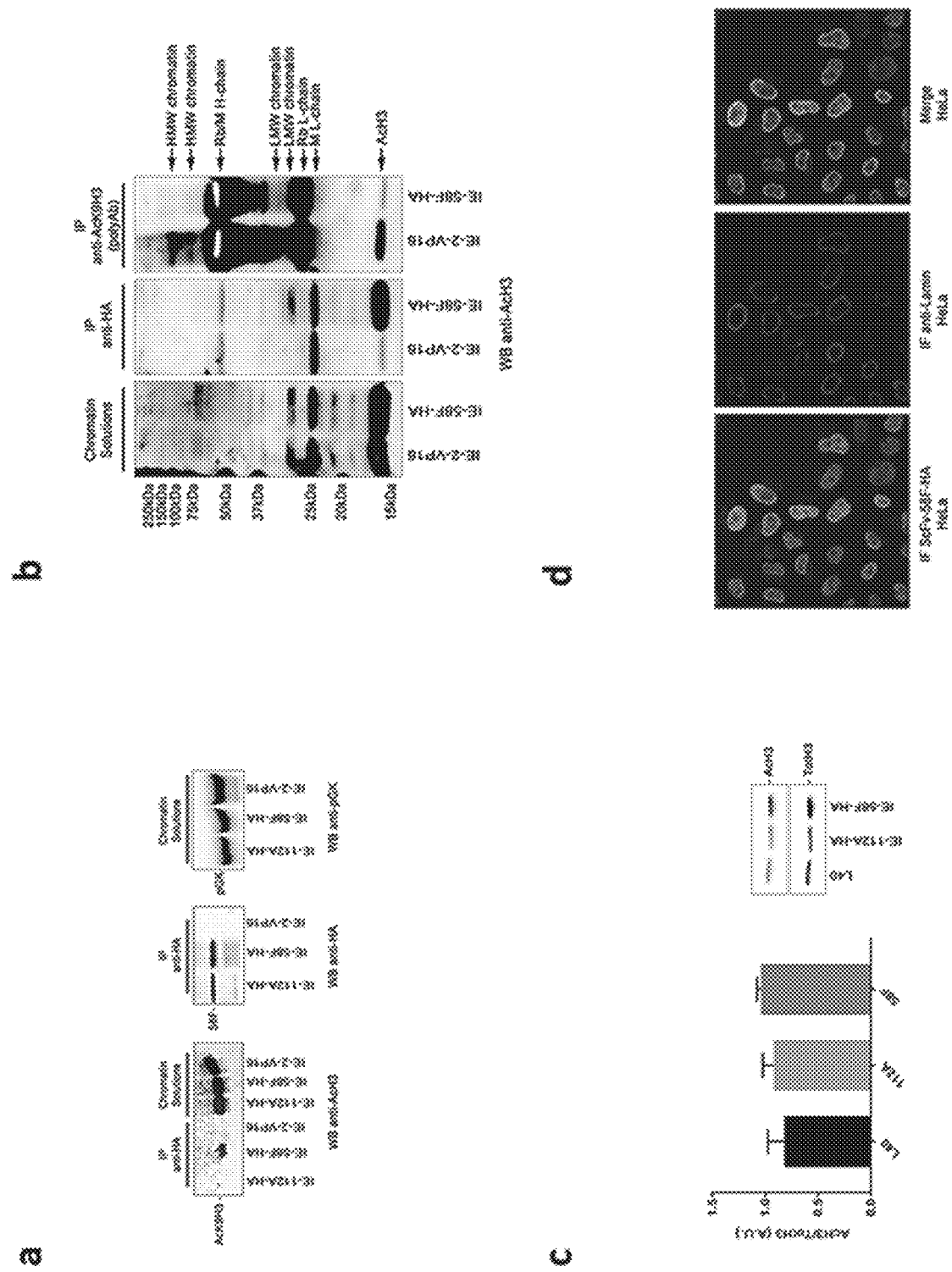

FIG. 18: Intracellular Immunoprecipitation of endogenous acetylated Histone H3 (a) Immunoprecipitation with anti-HA agarose of chromatin solutions (soluble extracts) from yeast cells intracellularly expressing either ScFv-112A-HA, ScFv-58F-HA or ScFv-2-VP16. Membrane blotted for AcK9H3 and HA. Only ScFv-58F-HA is able to pull-down AcH3, while another unrelated anti-acetyl intrabody, such as ScFv-112A-HA, does not. (b) Immunoprecipitation of chromatin solutions from yeast cells intracellularly expressing either ScFv-2-VP16 or ScFv-58F-HA, blotted for AcK9H3. First panel from left shows chromatin ladder from soluble yeast extracts used in the IP experiment. Panel in the middle shows how anti-HA Ab efficiently immunoprecipitates ScFv-58F-HA bound to AcH3 histone and to low molecular weight chromatin (LMW chromatin). Last panel on the right shows an IP of chromatin solutions from both yeast cell samples with a polyclonal anti-AcK9H3 antibody. IPs of low and high molecular weight chromatin and of AcH3 are strongly impaired in yeast cells expressing ScFv-58F-HA. HMW=High Molecular Weight; LMW=Low Molecular Weight; Rb=Rabbit; M=Mouse; H-chain=Heavy chain (IP antibody); L-chain=Light chain (IP antibody); AcH3=Acetyl-K9-H3 Histone. (c) Relative quantification by western blot of Acetylated Histone H3 in yeast expressing ScFv-58F, ScFv-112A or no intrabody (L40). Acetylated H3 band density from two biological replicates was normalized on Total H3. AcH3 was detected with Merck-Millipore #06-599, while total H3 was detected with Abcam #1791. Data are shown as mean+/−S.D. N=2. Student T test analysis demonstrates no significative difference between samples. (d) Immunofluorescence of HeLa cells nuclei using ScFv-58F-HA highlights euchromatin and shows that labelling by scFv-58F-HA does not merge with Lamin staining.

FIG. 19 Functional validation of anti-Integrase intrabodies. HIV infectivity assay. (a) Left panel HeLa cells infected with HIV virus, previously transfected with VH-112A, show a reduced viral integration, when the intrabody is localized in the cytoplasm. A significant difference in viral integration is observed in cells expressing the intrabody, compared to control cells (expressing respectively a non-related intrabody (p<0.05, VH-2), the anti-integrase VH-12X (p<0.05), the backbone vector (p<0.05)) or compared to non-transfected but infected cells (p<0.001, CTRL+). The VH-12X intrabody is instead able to reduce infectivity with respect to CTRL+with p<0.01, but only with p=0.058 and with p=0.078 if compared to VH-2 cyto and backbone respectively (comparison not shown). (b) Co-immunoprecipitation of HA-tagged antibody domains and different FLAG-tagged versions of Integrase proteins in HeLa cells. As previously (Cereseto et al. EMBOJ 2005), Flag-INwt construct is acetylated in mammalian cells, whilst Integrase mutated at Lysines 264, 266, 273 is not. As expected, only VH-112A is able to immunoprecipitate the AcIN selectively.

FIG. 20: Functional validation of anti-acetylated H3 histone intrabody ScFv-58F. Selective interference with acetylated H3 histone by the ScFv-58F intrabody regulates gene expression in yeast cells. (a) Heatmap of the significant differentially expressed genes between scFv112A (anti-acIN) and scFv58F (anti-H3AcK9) samples. Gene expression levels were filtered out to retain those showing a significant over- or under-expression (pAdj<0.05). Data were filtered according to the following conditions: i) pAdj<0.05 in the 58F-112A comparison; ii) L40-112A pAdj>0.05; iii) L40-58F pAdj<0.05. The values were normalized to the L40 sample levels. Four biological replicates for each sample were used. The list was further reduced applying a fold change threshold of 1.5. The statistical analysis was performed with R limma package and Benjamini correction was applied to the pValue (pAdj). In the graph, the marked (*) entries represent genes with a known association to histone acetylation. The heatmap in this Figure shows the most downregulated genes at the top, and the most upregulated genes at the bottom. (b) Principal Component Analysis on the microarray gene expression data. Each sample is composed of four independent biological replicates. Dim1 and Dim2 represent the first two principal components, the proportion of variance (POV) held by these components is reported in brackets as percentage. (c) Gene Ontology enrichment analysis of the dataset shown as heatmap in FIG. 3a. Barplot of the pValue associated to the most relevant Gene Ontology terms. GO enrichment analysis was performed on the significant differentially expressed genes between the ScFv-58F and ScFv-112A samples. The analysis and the most important terms were selected for the plot via David Ontology. (d) Validation by Real-Time PCR of selected differentially expressed genes between ScFv58F and ScFv112A samples. Data are shown as Log 2(FC)+/− SD. SD=standard deviation=sqrt(SDSample2+SDL402). FC=Fold Change=2−ΔΔCt normalized on Actin (ACT1) and L40 samples. Student T test (58F VS 112A, homoscedastic, two-tailed) was performed on ΔCt values. P values: PH089=9.235E-06, PH084=1.911E-03, CTR1=3.116E-03, TRM11=2.248E-03, URH1=3.318E-03. A gene that was not differently expressed between ScFv58F and ScFv-112A was also used as a negative control (APC1, not shown).

Figure 21:
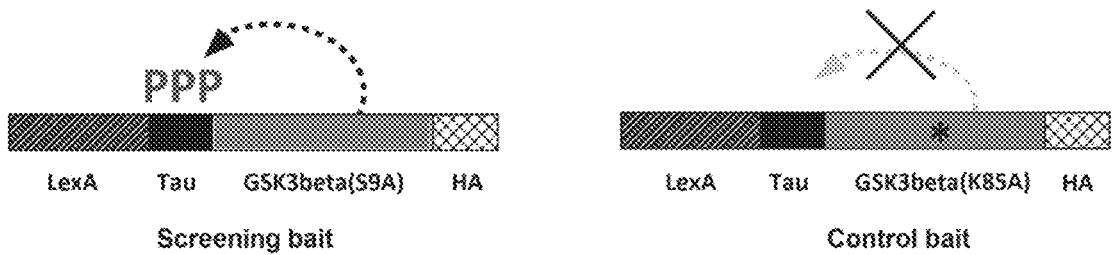

FIG. 21: PISA bait system for phosphorylated protein antigens. Full-length human Tau protein has been fused with modified version of human GSK3β (constitutively active mutant S9A) to produce a screenable version of Phospho-Tau (screening bait). To permit counter-screening for anti-phospho-Tau binders, a control bait is also used, which has the same sequence of the screening bait, except for a different mutation in the GSK3P enzyme (K85A), which completely impedes kinase activity (control bait).

Figure 22:
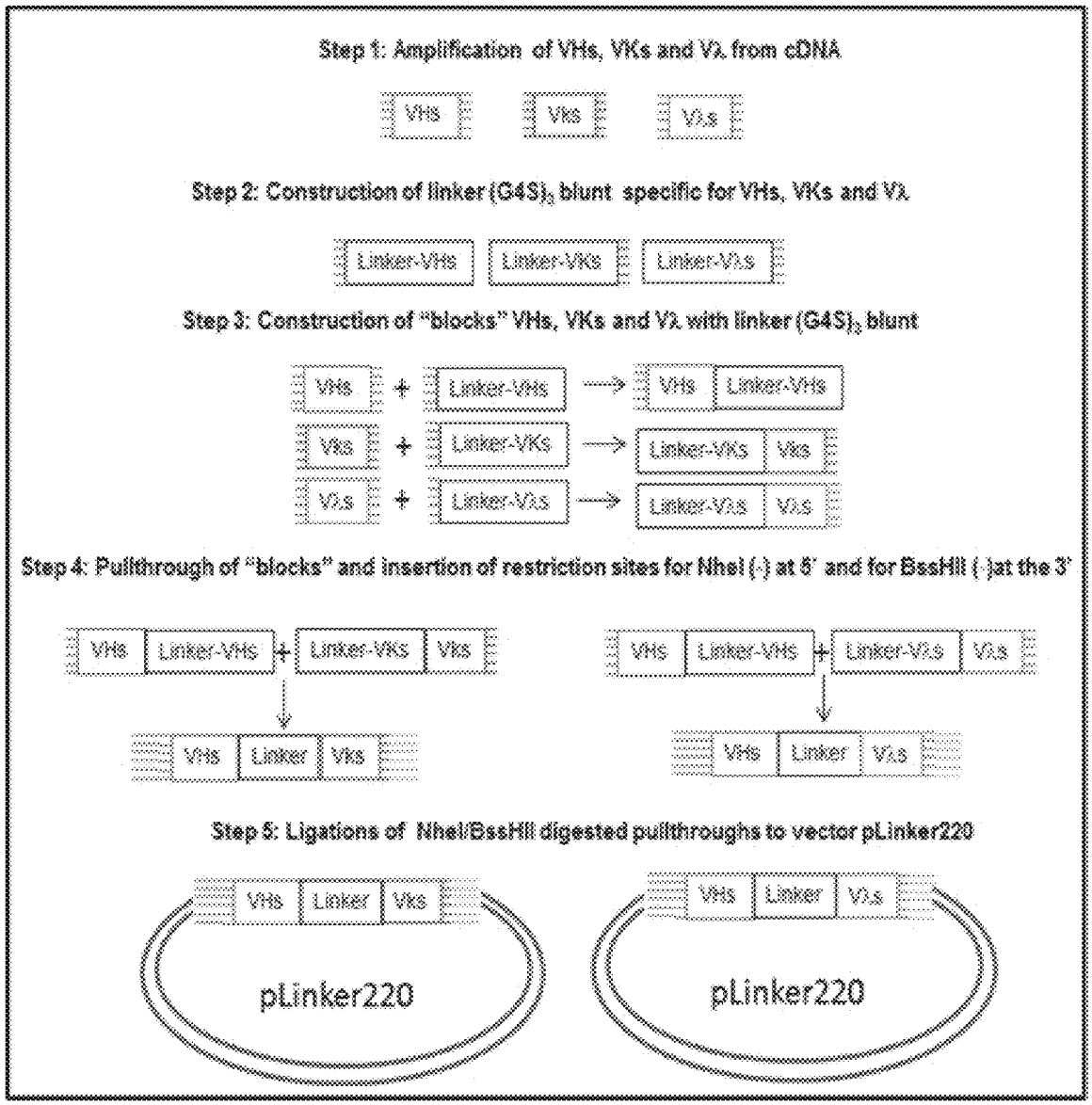
Figure 23:
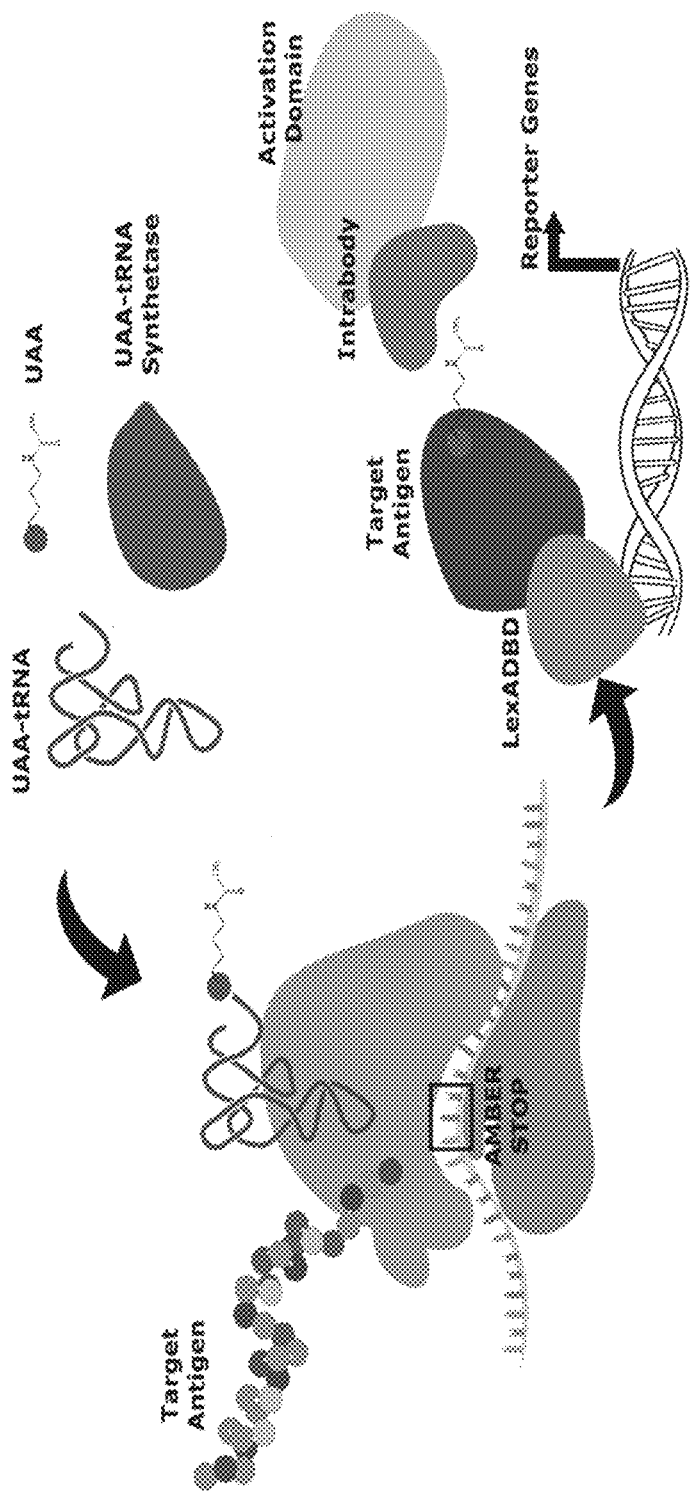

FIG. 22: Scheme illustrating the steps used for the construction of SPLINT human antibody libraries FIG. 23: Implementation of the expanded genetic code in the PISA Technology. A pair of tRNA/AA-tRNA synthetase matching set able to work in yeast, is integrated in the *S. cerevisiae* L40 screening strain by an amber codon (UAG codon) re-allocation. The new strain is adapted to perform PISA screenings to select intrabodies against PTMs genetically encoded in the target antigen through the use of intragenic amber stops. UAA=unnatural amino acid.

Figure 24:
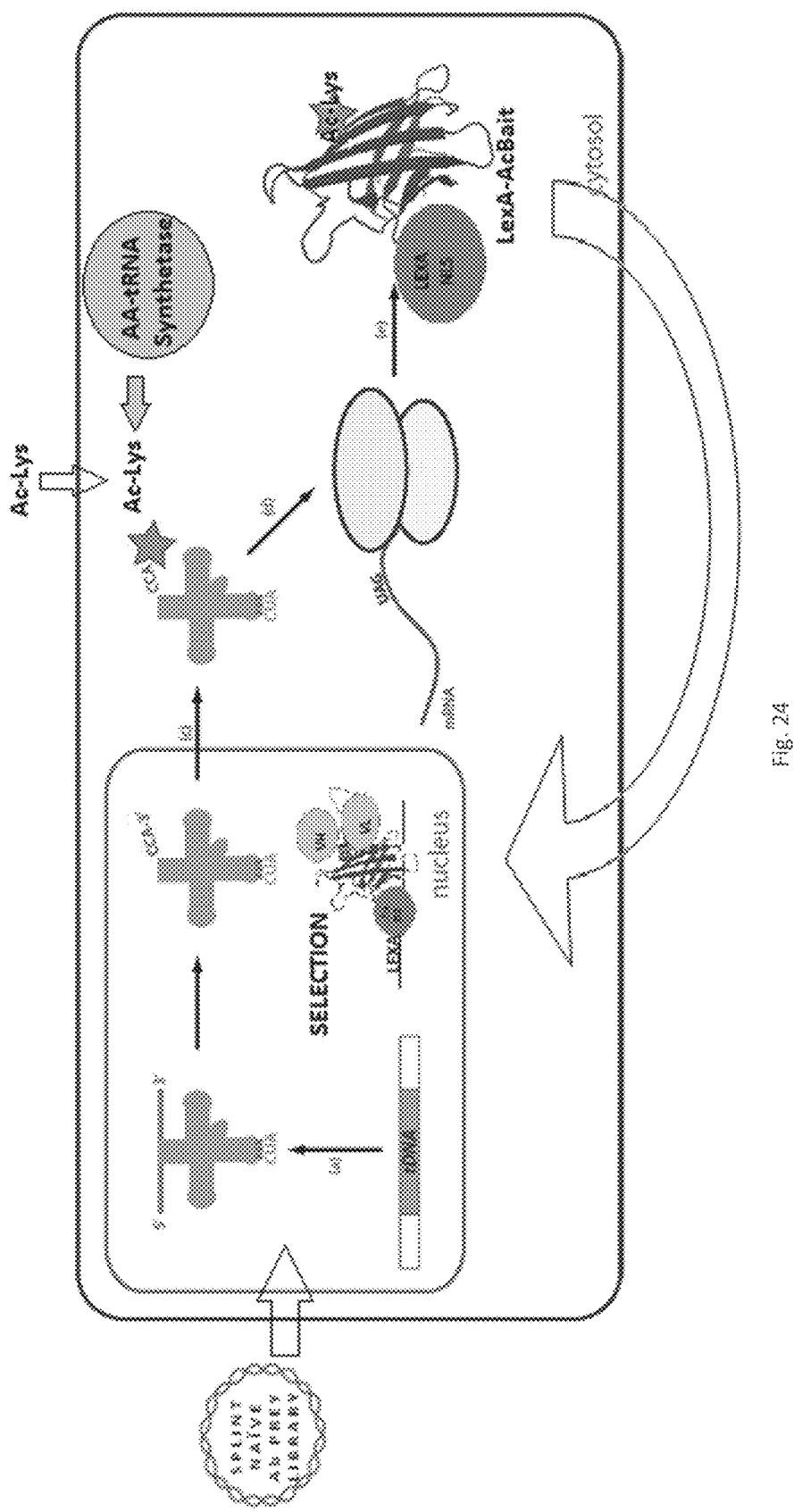

FIG. 24: PISA² 2.0 selection mechanism. The tRNA (CUA) is expressed by yeast and in the cytosol it mediates the incorporation of Acetyllysine, thanks to the corresponding aminoacyl-tRNA synthetase. After translation, the LexA-acetylated protein (which is equipped with a NLS) is transported to the nucleus, where selection can occur. (Adapted from Hancock et al, 2010)

Figure 25:
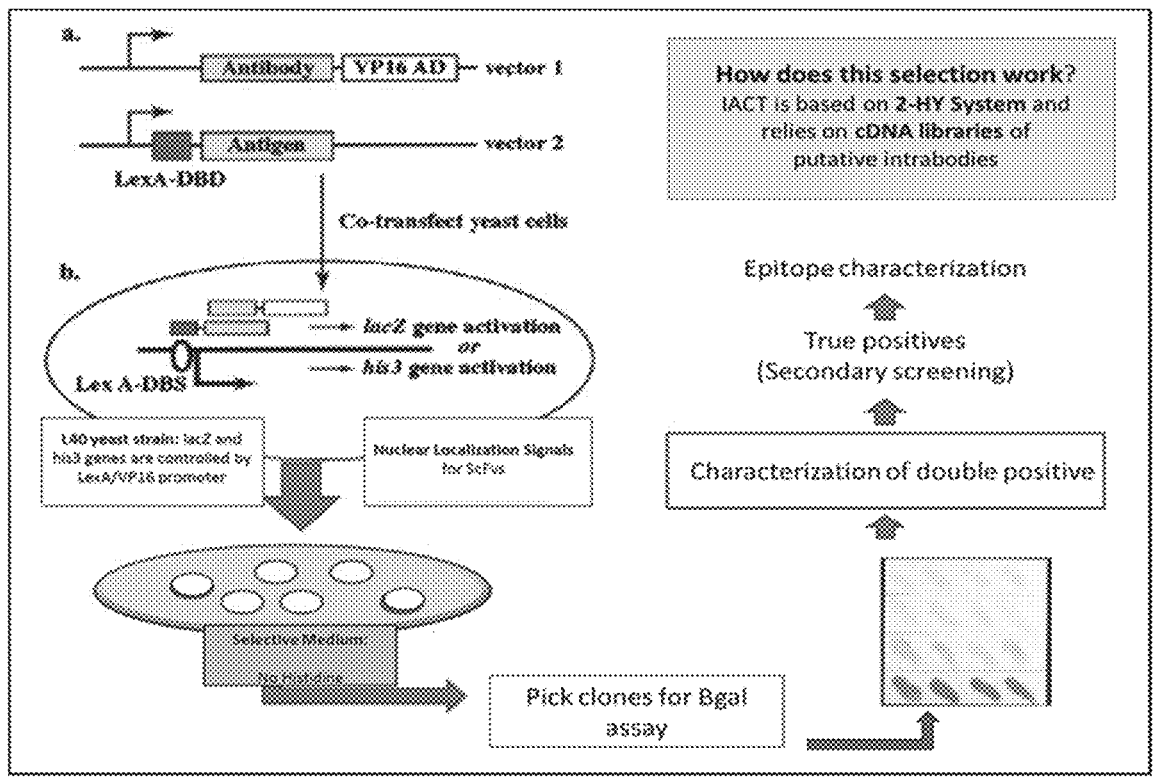

FIG. 25: IACT selection method. Briefly, IACT system is based on Y-2HY system, in which a genetically modified yeast not able to grow in absence of histidine is cotransformed with an antibody cDNA library and the target antigen. In the first construct ("the prey", vector1), the antibody gene is fused to VP16 activation domain, whilst in the second construct, namely "the bait" (vector2), LexA DBD is at the very N-term of the fusion protein. Only in case an antibody is able to recognize the antigen intracellularly, this binding will be responsible of the activation of two reporter genes: HISS and LacZ. Thus, yeast plated on SD-WHL medium will now be able to grow in absence of histidine, and will metabolize X-gal due to beta-galactosidase production. Double positive clones (His+/Lacz+) are further analyzed by extracting prey plasmid DNA and testing it again against the antigen ti validate positivity. Last steps include in vitro characterization of the isolated antibody and mapping of the bound epitope.

Figure 26:
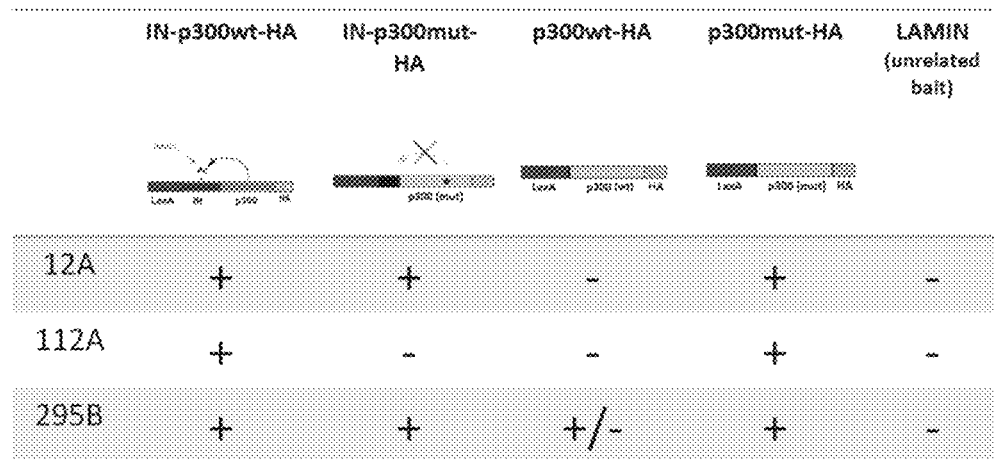

FIG. 26: Interaction specificity for anti-IN ScFvs. Here is summarized the epitope mapping with the IN bait panel at the end of the secondary screening.

EXAMPLES

Materials and Methods

Here inventors show results and methods from two selections, aimed at the selection of antibody domains against two PTMs: acetylated HIV-1 integrase (accession number AF029884.1) and acetylated Histone H3 (gene ID 852295). Inventors engineered the following acetylated baits: a) LexA-Integrase-p300 wt-HA and b) LexA-HistoneH3-Gcn5 wt-HA. ["HAT" (Histone Acetyl Transferase or "p300" (gene id 2033), and "HAT" or "Gcn5" (gene ID 853167) are used herein indifferently].

Baits Construction

DNA template for bait construction was PCR-amplified and adapted from different Gal4 tethered catalysis baits, that were already validated from previous authors for presence of acetylation by western blot and mass spectrometry. Constructs regarding the H3 bait were adapted from Guo et al. (2004), whilst Integrase baits were created from Allouch et al. (2011) baits. All construct listed below represent inventors' final baits, with LexA DBD at the N-term, and they were cloned in both pMICBD1 and pMICBD2 plasmids (Visintin et al., 2004). Cloning was performed by restriction site cut/ligation procedure.

Baits used in the IACT primary screening procedure are named "screening baits" or "main baits", and represent the version of the construct in which the catalytic domain of the acetylating enzyme (p300 or gcn5) is fully functional (Wild Type, "WT"). In this bait, the antigen (Integrase or H3) is constitutively acetylated, so through TACT it is possible to find intrabodies against any epitope of the bait, including acetylated and non-acetylated ones. Thus, to screen for acetylation-specific antibodies, a panel of mutated baits is used. For instance, a pool of selected intrabodies against LexA-Integrase-p300 wt-HA must be successively screened against LexA-Integrase-p300mut-HA, LexA-Integrase, LexA-p300 wt-HA, LexA-p300mut to check that no interaction with these baits occur. In fact, intrabodies that recognize specifically the acetylated version of the integrase (or H3) will be able to interact with the screening bait exclusively, since it is the only construct in which the antigen is acetylated (FIG. 1).

TABLE 2

| INTEGRASE BAITS | H3 HISTONE BAITS |
|---|---|
| pMICBD1-LexA-Integrase-p300wt-HA (screening bait) | pMICBD1-LexA-H3-Gcn5wt-HA (screening bait) |
| pMICBD1-LexA-Integrase-p300mut-HA | pMICBD1-LexA-H3-Gcn5mut-HA |
| pMICBD1-LexA-Integrase | pMICBD1-LexA-H3 |
| pMICBD1-LexA-p300wt-HA | pMICBD1-LexA-Gcn5wt-HA |
| pMICBD1-LexA-p300mut-HA | pMICBD1-LexA-Gcn5mut-HA |
| pMICBD2-LexA-Integrase-p300wt-HA (screening bait) | pMICBD2-LexA-H3-Gcn5wt-HA (screening bait) |
| pMICBD2-LexA-Integrase-p300mut-HA | pMICBD2-LexA-H3-Gcn5mut-HA |
| pMICBD2-LexA-Integrase | pMICBD2-LexA-H3 |
| pMICBD2-LexA-p300wt-HA | pMICBD2-LexA-Gcn5wt-HA |
| pMICBD2-LexA-p300mut-HA | pMICBD2-LexA-Gcn5mut-HA |

Table 2 - List of baits constructed for PISA screening. This table includes plasimds prepared for PISA screening. pMICBD1 plasmids have been used for the screening, while pMICBD2 plasmids, that contain a version of LexA mutated in nuclear localization signal, have been produced, but they are used only in case there is need for a more stringent cytoplasmic selection.

Sequences:

Construct cloned in pMICBD1 or pMICBD2 are identical except for a LexA mutation described in Visintin et al. JIM (2004). The "LexA" part of the sequence refers to WT LexA (pMICBD1 plasmids), which are the only plasmids used to produce data herein shown.

>LexA-Integrase-p300wt-HA (SEQ ID NO: 12)

MKALTARQQEVFDLIRDHISQTGMPPTRAEIAQRLGFRSPNAAEEHLKA

LARKGVIEIVSGASRGIRLLQEEEEGLPLVGRVAAGEPLLAQQHIEGHY

QVDPSLFKPNADFLLRVSGMSMKDIGIMDGDLLAVHKTQDVRNGQVVVA

RIDDEVTVKRLKKQGNKVELLPENSEFKPIVVDLRQQSFTIEGLAVGVI

RNGDWLEFLDGIDKAQEEHEKYHSNWRAMASDFNLPPVVAKEIVASCDK

CQLKGEAMHGQVDCSPGIWQLDCTHLEGKVILVAVHVASGYIEAEVIPA

ETGQETAYFLLKLAGRWPVKTVHTDNGSNFTSTTVKAACWWAGIKQEFG

IPYNPQSQGVIESMNKELKKIIGQVRDQAEHLKTAVQMAVFIHNFKRKG

GIGGYSAGERIVDIIATDIQTKELQKQITKIQNFRVYYRDSRDPVWKGP

AKLLWKGEGAVVIQDNSDIKVVPRRKAKIIRDYGKQMAGDDCVASRQDE

DRRRTSRVYKYCSKLSEVFEQEIDPVMQSLGYCCGRKLEFSPQTLCCYG

KQLCTIPRDATYYSYQNRYHFCEKCFNEIQGESVSLGDDPSQPQTTINK

EQFSKRKNDTLDPELFVECTECGRKMHQICVLHHEIIWPAGFVCDGCLK

KSARTRKENKFSAKRLPSTRLGTFLENRVNDFLRRQNHPESGEVTVRVV

HASDKTVEVKPGMKARFVDSGEMAESFPYRTKALFAFEEIDGVDLCFFG

MHVQEYGSDCPPPNQRRVYISYLDSVHFFRPKCLRTAVYHEILIGYLEY

```
VKKLGYTTGHIWACPPSEGDDYIFHCHPPDQKIPKPKRLQEWYKKMLDK
AVSERIVHDYKDIFKQATEDRLTSAKELPYFEGDFWPNVLEESIKELEQ
EEEERKREENTSNESTDVTKGDSKNAKKKNNKKTSKNKSSLSRGNKKKP
GMPNVSNDLSQKLYATMEKHKEVFFVIRLIAGPAANSLPPIVDPDPLIP
CDLMDGRDAFLTLARDKHLEFSSLRRAQWSTMCMLVELHTQSQDRFVYT
CNECYPYDVPDYA-
```

>LexA-Integrase-p300mut-HA
(SEQ ID NO: 13)
```
MKALTARQQEVFDLIRDHISQTGMPPTRAEIAQRLGFRSPNAAEEHLKA
LARKGVIEIVSGASRGIRLLQEEEEGLPLVGRVAAGEPLLAQQHIEGHY
QVDPSLFKPNADFLLRVSGMSMKDIGIMDGDLLAVHKTQDVRNGQVVVA
RIDDEVTVKRLKKQGNKVELLPENSEFKPIVVDLRQQSFTIEGLAVGVI
RNGDWLEFLDGIDKAQEEHEKYHSNWRAMASDFNLPPVVAKEIVASCDK
CQLKGEAMHGQVDCSPGIWQLDCTHLEGKVILVAVHVASGYIEAEVIPA
ETGQETAYFLLKLAGRWPVKTVHTDNGSNFTSTTVKAACWWAGIKQEFG
IPYNPQSQGVIESMNKELKKIIGQVRDQAEHLKTAVQMAVFIHNFKRKG
GIGGYSAGERIVDIIATDIQTKELQKQITKIQNFRVYYRDSRDPVWKGP
AKLLWKGEGAVVIQDNSDIKVVPRRKAKIIRDYGKQMAGDDCVASRQDE
DRRRTSRVYKYCSKLSEVFEQEIDPVMQSLGYCCGRKLEFSPQTLCCYG
KQLCTIPRDATYYSYQNRYHFCEKCFNEIQGESVSLGDDPSQPQTTINK
EQFSKRKNDTLDPELFVECTECGRKMHQICVLHHEIIWPAGFVCDGCLK
KSARTRKENKFSAKRLPSTRLGTFLENRVNDFLRRQNHPESGEVTVRVV
HASDKTVEVKPGMKARFVDSGEMAESFPYRTKALFAFEEIDGVDLCFFG
MHVQEYGSDCPPPNQRRVYISYLYSVHFFRPKCLRTAVYHEILIGYLEY
VKKLGYTTGHIWACPPSEGDDYIFHCHPPDQKIPKPKRLQEWYKKMLDK
AVSERIVHDYKDIFKQATEDRLTSAKELPYFEGDFWPNVLEESIKELEQ
EEEERKREENTSNESTDVTKGDSKNAKKKNNKKTSKNKSSLSRGNKKKP
GMPNVSNDLSQKLYATMEKHKEVFFVIRLIAGPAANSLPPIVDPDPLIP
CDLMDGRDAFLTLARDKHLEFSSLRRAQWSTMCMLVELHTQSQDRFVYT
CNECYPYDVPDYA-
```

>LexA-p300wt-HA
(SEQ ID NO: 14)
```
MKALTARQQEVFDLIRDHISQTGMPPTRAEIAQRLGFRSPNAAEEHLKA
LARKGVIEIVSGASRGIRLLQEEEEGLPLVGRVAAGEPLLAQQHIEGHY
QVDPSLFKPNADFLLRVSGMSMKDIGIMDGDLLAVHKTQDVRNGQVVVA
RIDDEVTVKRLKKQGNKVELLPENSEFKPIVVDLRQQSFTIEGLAVGVI
RNGDWLEFTSRVYKYCSKLSEVFEQEIDPVMQSLGYCCGRKLEFSPQTL
CCYGKQLCTIPRDATYYSYQNRYHFCEKCFNEIQGESVSLGDDPSQPQT
TINKEQFSKRKNDTLDPELFVECTECGRKMHQICVLHHEIIWPAGFVCD
GCLKKSARTRKENKFSAKRLPSTRLGTFLENRVNDFLRRQNHPESGEVT
VRVVHASDKTVEVKPGMKARFVDSGEMAESFPYRTKALFAFEEIDGVDL
CFFGMHVQEYGSDCPPPNQRRVYISYLDSVHFFRPKCLRTAVYHEILIG
YLEYVKKLGYTTGHIWACPPSEGDDYIFHCHPPDQKIPKPKRLQEWYKK
MLDKAVSERIVHDYKDIFKQATEDRLTSAKELPYFEGDFWPNVLEESIK
ELEQEEEERKREENTSNESTDVTKGDSKNAKKKNNKKTSKNKSSLSRGN
KKKPGMPNVSNDLSQKLYATMEKHKEVFFVIRLIAGPAANSLPPIVDPD
PLIPCDLMDGRDAFLTLARDKHLEFSSLRRAQWSTMCMLVELHTQSQDR
FVYTCNECYPYDVPDYA-
```

>LexA-p300mut-HA
(SEQ ID NO: 15)
```
MKALTARQQEVFDLIRDHISQTGMPPTRAEIAQRLGFRSPNAAEEHLKA
LARKGVIEIVSGASRGIRLLQEEEEGLPLVGRVAAGEPLLAQQHIEGHY
QVDPSLFKPNADFLLRVSGMSMKDIGIMDGDLLAVHKTQDVRNGQVVVA
RIDDEVTVKRLKKQGNKVELLPENSEFKPIVVDLRQQSFTIEGLAVGVI
RNGDWLEFTSRVYKYCSKLSEVFEQEIDPVMQSLGYCCGRKLEFSPQTL
CCYGKQLCTIPRDATYYSYQNRYHFCEKCFNEIQGESVSLGDDPSQPQT
TINKEQFSKRKNDTLDPELFVECTECGRKMHQICVLHHEIIWPAGFVCD
GCLKKSARTRKENKFSAKRLPSTRLGTFLENRVNDFLRRQNHPESGEVT
VRVVHASDKTVEVKPGMKARFVDSGEMAESFPYRTKALFAFEEIDGVDL
CFFGMHVQEYGSDCPPPNQRRVYISYLYSVHFFRPKCLRTAVYHEILIG
YLEYVKKLGYTTGHIWACPPSEGDDYIFHCHPPDQKIPKPKRLQEWYKK
MLDKAVSERIVHDYKDIFKQATEDRLTSAKELPYFEGDFWPNVLEESIK
ELEQEEEERKREENTSNESTDVTKGDSKNAKKKNNKKTSKNKSSLSRGN
KKKPGMPNVSNDLSQKLYATMEKHKEVFFVIRLIAGPAANSLPPIVDPD
PLIPCDLMDGRDAFLTLARDKHLEFSSLRRAQWSTMCMLVELHTQSQDR
FVYTCNECYPYDVPDYA-
```

>LexA-IN
(SEQ ID NO: 16)
```
MKALTARQQEVFDLIRDHISQTGMPPTRAEIAQRLGFRSPNAAEEHLKA
LARKGVIEIVSGASRGIRLLQEEEEGLPLVGRVAAGEPLLAQQHIEGHY
QVDPSLFKPNADFLLRVSGMSMKDIGIMDGDLLAVHKTQDVRNGQVVVA
RIDDEVTVKRLKKQGNKVELLPENSEFKPIVVDLRQQSFTIEGLAVGVI
RNGDWLEFLDGIDKAQEEHEKYHSNWRAMASDFNLPPVVAKEIVASCDK
CQLKGEAMHGQVDCSPGIWQLDCTHLEGKVILVAVHVASGYIEAEVIPA
ETGQETAYFLLKLAGRWPVKTVHTDNGSNFTSTTVKAACWWAGIKQEFG
IPYNPQSQGVIESMNKELKKIIGQVRDQAEHLKTAVQMAVFIHNFKRKG
GIGGYSAGERIVDIIATDIQTKELQKQITKIQNFRVYYRDSRDPVWKGP
AKLLWKGEGAVVIQDNSDIKVVPRRKAKIIRDYGKQMAGDDCVASRQDE
D-
```

>LexA-HistoneH3-Gcn5wt-HA
(SEQ ID NO: 17)
```
MKALTARQQEVFDLIRDHISQTGMPPTRAEIAQRLGFRSPNAAEEHLKA
LARKGVIEIVSGASRGIRLLQEEEEGLPLVGRVAAGEPLLAQQHIEGHY
QVDPSLFKPNADFLLRVSGMSMKDIGIMDGDLLAVHKTQDVRNGQVVVA
RIDDEVTVKRLKKQGNKVELLPENSEFKPIVVDLRQQSFTIEGLAVGVI
RNGDWLEFPGIRRPAANYLFDDEDTPPNPKKEIEFQLTTMFMARTKQTA
```

-continued

RKSTGGKAPRKQLASKAARKSAPSTGGVKKPHRYKPGTVALREIRRFQK

STEPGSPILGYWKGRRDHPPKSDLIEGRGDPEVKRVKLENNVEEIQPEQ

AETNKQEGTDKENKGKFEKETERIGGSEVVTDVEKGIVKFEFDGVEYTF

KERPSVVEENEGKIEFRVVNNDNTKENMMVLTGLKNIFQKQLPKMPKEY

IARLVYDRSHLSMAVIRKPLTVVGGITYRPFDKREFAEIVFCAISSTEQ

VRGYGAHLMNHLKDYVRNTSNIKYFLTYADNYAIGYFKKQGFTKEITLD

KSIWMGYIKDYEGGTLMQCNMAIPGGGRIFYPYDVPDYAGYPYDVPDYA

GSYPYDVPDYA-

>LexA-HistoneH3-Gcn5mut-HA (SEQ ID NO: 18)
MKALTARQQEVFDLIRDHISQTGMPPTRAEIAQRLGFRSPNAAEEHLKA

LARKGVIEIVSGASRGIRLLQEEEEGLPLVGRVAAGEPLLAQQHIEGHY

QVDPSLFKPNADFLLRVSGMSMKDIGIMDGDLLAVHKTQDVRNGQVVVA

RIDDEVTVKRLKKQGNKVELLPENSEFKPIVVDLRQQSFTIEGLAVGVI

RNGDWLEFPGIRRPAANYLFDDEDTPPNPKKEIEFQLTTMFMARTKQTA

RKSTGGKAPRKQLASKAARKSAPSTGGVKKPHRYKPGTVALREIRRFQK

STEPGSPILGYWKGRRDHPPKSDLIEGRGDPEVKRVKLENNVEEIQPEQ

AETNKQEGTDKENKGKFEKETERIGGSEVVTDVEKGIVKFEFDGVEYTF

KERPSVVEENEGKIEFRVVNNDNTKENMMVLTGLKNIFQKQLPKMPKEY

IARLVYDRSHLSMAVIRKPLTVVGGITYRPFDKREFAEIVFCAISSTEQ

VRGYGAHLMNHLKDYVRNTSNIKYFLTYADNYAIGYAKKQGFTKEITLD

KSIWMGYIKDYEGGTLMQCNMAIPGGGRIFYPYDVPDYAGYPYDVPDYA

GSYPYDVPDYA-

>LexA-Gcn5wt-HA (SEQ ID NO: 19)
MKALTARQQEVFDLIRDHISQTGMPPTRAEIAQRLGFRSPNAAEEHLKA

LARKGVIEIVSGASRGIRLLQEEEEGLPLVGRVAAGEPLLAQQHIEGHY

QVDPSLFKPNADFLLRVSGMSMKDIGIMDGDLLAVHKTQDVRNGQVVVA

RIDDEVTVKRLKKQGNKVELLPENSEFKPIVVDLRQQSFTIEGLAVGVI

RNGDWLEFPGIRRPGSPILGYWKGRRDHPPKSDLIEGRGDPEVKRVKLE

NNVEEIQPEQAETNKQEGTDKENKGKFEKETERIGGSEVVTDVEKGIVK

FEFDGVEYTFKERPSVVEENEGKIEFRVVNNDNTKENMMVLTGLKNIFQ

KQLPKMPKEYIARLVYDRSHLSMAVIRKPLTVVGGITYRPFDKREFAEI

VFCAISSTEQVRGYGAHLMNHLKDYVRNTSNIKYFLTYADNYAIGYFKK

QGFTKEITLDKSIWMGYIKDYEGGTLMQCNMAIPGGGRIFYPYDVPDYA

GYPYDVPDYAGSYPYDVPDYA-

>LexA-Gcn5mut-HA (SEQ ID NO: 20)
MKALTARQQEVFDLIRDHISQTGMPPTRAEIAQRLGFRSPNAAEEHLKA

LARKGVIEIVSGASRGIRLLQEEEEGLPLVGRVAAGEPLLAQQHIEGHY

QVDPSLFKPNADFLLRVSGMSMKDIGIMDGDLLAVHKTQDVRNGQVVVA

RIDDEVTVKRLKKQGNKVELLPENSEFKPIVVDLRQQSFTIEGLAVGVI

RNGDWLEFPGIRRPGSPILGYWKGRRDHPPKSDLIEGRGDPEVKRVKLE

-continued

NNVEEIQPEQAETNKQEGTDKENKGKFEKETERIGGSEVVTDVEKGIVK

FEFDGVEYTFKERPSVVEENEGKIEFRVVNNDNTKENMMVLTGLKNIFQ

KQLPKMPKEYIARLVYDRSHLSMAVIRKPLTVVGGITYRPFDKREFAEI

VFCAISSTEQVRGYGAHLMNHLKDYVRNTSNIKYFLTYADNYAIGYAKK

QGFTKEITLDKSIWMGYIKDYEGGTLMQCNMAIPGGGRIFYPYDVPDYA

GYPYDVPDYAGSYPYDVPDYA-

>LexA-H3Histone (SEQ ID NO: 21)
MKALTARQQEVFDLIRDHISQTGMPPTRAEIAQRLGFRSPNAAEEHLKA

LARKGVIEIVSGASRGIRLLQEEEEGLPLVGRVAAGEPLLAQQHIEGHY

QVDPSLFKPNADFLLRVSGMSMKDIGIMDGDLLAVHKTQDVRNGQVVVA

RIDDEVTVKRLKKQGNKVELLPENSEFKPIVVDLRQQSFTIEGLAVGVI

RNGDWLEFPGIRRPAANYLFDDEDTPPNPKKEIEFQLTTMFMARTKQTA

RKSTGGKAPRKQLASKAARKSAPSTGGVKKPHRYKPGTVALREIRRFQK

STE-

Baits Validation

After plasmid DNA production, new baits were tested in yeast to check good intracellular expression, acetylation status and auto-activation phenomena. Auto-activation occurs when the bait alone, without any prey, is able to activate the transcriptional markers in L40 yeast strain, being able to grow in absence of histidine. This would affect the screening, since yeast has to grow only upon specific bait/prey co-expression. Indeed, His3 production of L40 strain genetically depends from LexA promoter, so that this enzyme is produced when a specific antibody interacts with a bait only. To avoid non-specific yeast growth, we used 3-AT chemical (3-amino-1,2,4-triazole), a specific inhibitor of His3 enzyme (responsible for Histidine production), to adjust his3 basal levels to zero. Required minimum 3-AT concentration is determined through a growth assay. All tests are made on stabilized yeast bait lines. (FIGS. 2, 3, 4)

P.I.S.A. Screenings

Screening is based on adaptation of IACT. In the method of the invention, LexA baits are totally different from classic IACT baits, since they are Post-translationally modified in cis by genetic fusion of an enzyme. As for the primary screening protocol, no substantial modifications have been made with respect to original paper (Visintin et al., 1999). (FIG. 16)

During secondary screening, positive clones from primary screening are tested again with the main bait, and also with control constructs to map the targeted epitope intracellularly, in addition to LexA-Lamin (unrelated, LexA-fusion bait) and/or LexA-HA bait.

For both baits, a mouse naïve ScFv library (a SPLINT library) has been screened [Visintin et al.—"Intracellular antibodies for proteomics"—JIM (2004)] finding in each case a specific intrabody that is able to recognize the acetylated version of the antigen but not the non-acetylated one (FIG. 25).

LexA-Integrase-p300 wt-HA Screening

This screening produced 2.25 million transformants (evaluated by counting serial cell dilutions on—SD-WL (minimum non-selective medium) (a minumin medium without tryptophan and leucine) plates). After O/N doubling in SD-WL medium, culture produced 4.5 doublings. Selected clones on SD-WHL ["minimum selective medium"

(without tryptophan, leucine and histidine)] plates (screening plates, lacking histidine) were 500. Between day 4 to 6 after plating, biggest colonies were restreaked on fresh SD-WHL plates and a Beta-Galactosidase filter assay was performed to confirm double positives. Number of yeasts positives to both markers was 219. From these clones, a DNA fingerprint was performed, then prey plasmids were extracted, transformed in bacteria, mini-prepped as single clones, fingerprinted again to check for different preys, and co-transformed into control/main baits for secondary screening.

After secondary screening, we selected 3 true/different positives. Their interactions are summarized in FIG. 26.

112A ScfV seemed to be a good candidate for Acetyl-Integrase specific binding, but a slight cross-reaction against the p300 bait was observed. Inventors thought that this effect could be moderated by splitting the ScFv into two separate Variable Domains (VH and VL), since antibody binding activity is often possessed and retained by one of the two variable regions. Prey plasmids were then sequenced and analyzed though Abysis.org database, which permits easy recognition of domain antibodies ORFs. VH and VL have been thus subcloned in pLinker220 plasmid and used for a new secondary screening.

Astonishingly, use of VH domain of 112A intrabody resulted in highly specific in vivo interaction for the acetylated version of the bait (FIG. 5). No activity was observed using VL domain. VH12A was also characterized and proven to be a general integrase binder, with preferential binding for Acetyl-Integrase. (Table 3)

TABLE 3

Table 3 Interaction specificity of anti-IN VH domains compared to anti-IN ScFvs.
Table shows that VH domains of original selected ScFvs intrabodies not only retain binding activity, but also eliminate undesired cross-reaction effects.

| | IN-HATwt-HA | IN-HATmut-HA | HATwt-HA | HATmut-HA | LAMIN (unrelated bait) | IN-stop (non-acetylated) |
|---|---|---|---|---|---|---|
| ScFV 12A | + | + | − | + | − | + |
| VH 12A | + | − | − | − | − | + |
| ScFv 112A | + | − | − | + | − | − |
| VH 112A | + | − | − | − | − | − |

LexA-H3-Gcn5 wt-HA Screening

Transformants=8.8*10^7; cell doublings after O/N in SD-WL=5; Selected clones on SD-WHL+10 mM 3AT plates=700. True positive clones (different sequences binding the screening bait)=3; True positive intrabodies that bind Acetyl-HistoneH3=1 (Table 4, FIG. 7).

TABLE 4

| | 2A | 58F | 249B | y1 | scfv2 |
|---|---|---|---|---|---|
| LexA-H3-Gcn5wt-HA | + | + | + | + | − |
| LexA-H3-Gcn5mut-HA | + | − | + | + | − |
| LexA-Gcn5wt-HA | +/−? | − | + | + | − |

TABLE 4-continued

| | 2A | 58F | 249B | y1 | scfv2 |
|---|---|---|---|---|---|
| LexA-Gcn5mut-HA | +/−? | − | + | + | − |
| LexA-Synuclein | − | − | − | + | − |

Table 4: Epitope mapping for ScFv-58F. Table summarizes interaction of ScFv-58 intrabody against a panel of H3/H3 depleted baits, showing that LexA-H3-Gcn5wt-HA bait is the only bound bait.

Sequence of described intrabodies
>VH-12A
(SEQ ID NO: 1)
```
         10         20         30         40
QVQLQQSGAE LVKPGASVKL SCTASGFNIK DTYMHWVKQR 50         60         70         80
PEQGLEWIGR IDPANGNTKY DPKFQGKATI TADTSSNTAY 90        100        110
LQLSSLTSED TAVYYCASLL WWGQGTLVTV SAASVSS
```

Nucleotide sequence of VH-12A (VH-12X)
(SEQ ID NO: 97)
```
CAGGTTCAGCTTCAGCAGTCTGGGGCAGAGCTTGTGAAGCCAGGGGCC

TCAGTCAAGTTGTCCTGCACAGCTTCTGGCTTCAACATTAAAGACACC

TATATGCACTGGGTGAAGCAGAGGCCTGAACAGGGCCTGGAGTGGATT

GGAAGGATTGATCCTGCGAATGGTAATACTAAATATGACCCGAAGTTC

CAGGGCAAGGCCACTATAACAGCAGACACATCCTCCAACACAGCCTAC

CTGCAGCTCAGCAGCCTGACATCTGAGGACACTGCCGTCTATTACTGT

GCTAGTCTACTATGGTGGGGCCAAGGGACTCTGGTCACTGTCTCTGCA

GCTAGCGTTTCGAGC
```

>VH-112A
(SEQ ID NO: 2)
```
         10         20         30         40
QVHVKQSGAE LVRPGASVKI SCKAFGYTFT NHHINWVKQR 50         60         70         80
PGQGLEWIGY INPSTGYTEY NQKFKDKATL TADKSSSTAY 90        100        110        120
MQLSSLTSED SAVYYCASYY GSSYAMDYWG QGTSVTVSS
```

Nucleotide sequence of VH-112A:
(SEQ ID NO: 98)
```
CAGGTCCACGTGAAGCAGTCTGGGGCTGAGCTGGTGAGGCCTGGGGCC

TCAGTGAAGATTTCCTGCAAGGCTTTTGGCTACACCTTCACAAACCAT

CATATAAACTGGGTGAAGCAGAGGCCTGGACAGGGTCTGGAATGGATT

GGATACATTAATCCTAGCACTGGTTATACTGAGTACAATCAGAAGTTC

AAGGACAAGGCCACATTGACTGCAGACAAATCCTCCAGCACAGCCTAC

ATGCAACTGAGCAGCCTGACATCTGAGGACTCTGCAGTCTATTACTGT

GCAAGTTACTACGGTAGTAGCTATGCTATGGACTACTGGGGTCAAGGA

ACCTCAGTCACCGTCTCCTCAGCTAGCGTTTCGAGC
```

>ScFv-58F
(SEQ ID NO: 3)
```
         10         20         30         40
DILMTQSPAI MSASPGEKVT MTCRASSSVS SSYLHWYQQK 50         60         70         80
SGASPKLWIY STSNLASGVP ARFSGSGSGT SYSLTISSVE
```

```
                90         100        110        120
     AEDAATYYCQ QYSGYPWTSG GGTKLEIKRS GGSTSGSGKP 130        140        150        160
     GSGEGSSSTE VKVEESGGGL VQPGGSMKLS CVASGFTFSN 170        180        190        200
     YWMNWVRQSP EKGLEWVAEI RLKSNNYATH YAESVKGRFT 210        220        230        240
     ISRDDSESSV YLQMNNLRAE DTGIYYCTRR NGPSSRAMDY

250
     WGQGTTVTVS S
```

ScFv-58F heavy chain:
(SEQ ID NO: 92)
EVKVEESGGGLVQPGGSMKLSCVASGFTFSNYWMNWVRQSPEKGLEWV

AEIRLKSNNYATHYAESVKGRFTISRDDSESSVYLQMNNLRAEDTGIY

YCTRRNGPSSRAMDYWGQGTTVTVSS

ScFv-58F light chain:
(SEQ ID NO: 93)
DILMTQSPAIMSASPGEKVTMTCRASSSVSSSYLHWYQQKSGASPKLW

IYSTSNLASGVPARFSGSGSGTSYSLTISSVEAEDAATYYCQQYSGYP

WTSGGGTKLEIKRSG

Nucleotide sequence of ScFv-58F:
(SEQ ID NO: 99)
GATATTTTGATGACTCAGTCTCCAGCAATCATGTCTGCATCTCCAGGG

GAAAAGGTCACCATGACCTGCAGGGCCAGCTCAAGTGTAAGTTCCAGT

TACTTGCACTGGTACCAGCAGAAGTCAGGTGCCTCCCCCAAACTCTGG

ATTTATAGCACATCCAACTTGGCTTCTGGAGTCCCTGCTCGCTTCAGT

GGCAGTGGGTCTGGGACCTCTTACTCTCTCACAATCAGCAGTGTGGAG

GCTGAAGATGCTGCCACTTATTACTGCCAGCAGTACAGTGGTTACCCG

TGGACGTCCGGTGGAGGCACCAAGCTGGAAATAAAACGTTCCGGAGGG

TCGACCAGCGGTTCTGGGAAACCAGGTTCCGGTGAAGGCTCGAGCAGT

ACCGAAGTGAAAGTTGAGGAGTCTGGAGGAGGCTTGGTGCAACCTGGA

GGATCCATGAAACTCTCCTGTGTCGCCTCTGGATTCACTTTCAGTAAC

TACTGGATGAACTGGGTCCGCCAGTCTCCAGAGAAGGGGCTTGAGTGG

GTTGCTGAAATTAGATTGAAATCTAATAATTATGCAACACATTATGCG

GAGTCTGTGAAAGGGAGGTTCACCATCTCAAGAGATGATTCCGAAAGT

AGTGTCTACCTGCAAATGAACAACTTAAGAGCTGAAGACACTGGCATT

TATTACTGTACCAGGAGGAATGGACCCTCCTCCCGGGCTATGGACTAC

TGGGGTCAAGGAACCACGGTCACCGTCTCCTCAGCTAGCGTTTCGAGC

Sequences of the CDRs of the obtained antibodies, with the CDRs defined according to Abysis.org predictions and Chothia numbering, are:

ScFv-58F CDRH1:
(SEQ ID NO: 80)
G F T F S N Y

ScFv-58F CDRH2:
(SEQ ID NO: 81)
R L K S N N Y A

ScFv-58F CDRH3:
(SEQ ID NO: 82)
R N G P S S R A M D Y

ScFv-58F CDRL1:
(SEQ ID NO: 83)
R A S S S V S S S Y L H

ScFv-58F CDRL2:
(SEQ ID NO: 84)
S T S N L A S

ScFv-58F CDRL3:
(SEQ ID NO: 85)
Q Q Y S G Y P W T

VH-112A CDR1:
(SEQ ID NO: 86)
G Y T F T N H

VH-112A CDR2:
(SEQ ID NO: 87)
N P S T G Y

VH-112A CDR3:
(SEQ ID NO: 88)
Y Y G S S Y A M D Y

VH-12A CDR1:
(SEQ ID NO: 89)
G F N I K D T

VH-12A CDR2:
(SEQ ID NO: 90)
D P A N G N

VH-12A CDR3:
(SEQ ID NO: 91)
L L W

In Vitro Characterization of Selected Intrabodies

Anti-PTM intrabodies were then assayed in vitro to further confirm their binding and their specificity. In this phase, new constructs were created, both for antigens and antibodies.

Anti-Acetyl-Integrase Intrabody VH-112A & Anti-Integrase Intrabody VH-12A-Co-Immunoprecipitation Assay with Purified Ac-Integrase Preparation of the Cell Extracts Expressing VH-112A and VH-12A Intrabodies.

After true positive clones have been confirmed and mapped for the bound epitope, they were subcloned in bacterial expression plasmid pGIO1 (described in Meli et al.). Cloning was performed by previous cut of pLinker220 2HY clones with BssHII and NheI enzymes. After gel purification (ca. 750 bp for ScFv and 400 bp for VH), inserts were ligated to pGIO1 backbone opened with same enzymes. Plasmid was then modified with insertion of NheI-HA-NheI tag at the C-term of the intrabody. Resulting clones were checked by sequencing. Plasmids were transformed in BL21(DE3) bacterial strain. A single colony was used for O/N growth at 37° C. in LB+Kanamycin in a shaker (240 rpm). The day after, culture was diluted to OD600=0.2 and grown at 37° C. to OD600=0.55-0.70. Cultures are then induced with 0.5 mM IPTG at 25° C. for 5h. Cell [E. coli BL21 (DE3)] pellets were lysed in TBS (20 mM TRIS, 150 mM NaCl—pH 8.0 was adopted for VH-112A-HA and pH 7.5 was used for VH-12A-HA)+Roche protein inhibitor Complete Mini with EDTA 1 mM, PMSF 1 mM+lysozime 1 mg/mL for 20 min RT, on a wheel. Samples were then sonicated on ice for 3 times, 10 sec each, with 1 minute rest between sonications. At this point lysated are incubated with DNase for 15 min RT and spun 2× 15 min at 4° C. at 16,100 rcf. Surnatant is preferably used fresh for Co-IP experiments, or can be stored in small aliquots at −80° C.

Preparation of the Acetylated Integrase

Integrase has been subcloned in pASK-IBA37 plus plasmid, a bacterial expression vector with 6×His tag at the N-terminus. After BL21 transformation, His-Integrase protein is purified with TALON resin (Invitrogen) as described in Allouch et al. (2011). 15 ug of Acetylated Integrase is then obtained by using either p300 catalytic domain from ActiveMotif or p300 full from BsPBioscience in the following 50 min reaction at RT: 15 ug of purified His-Integrase (or histones), 5 uL of p300 enzyme, 1×HAT buffer (BSPBioscience), 200 uM Ac-CoA. Final volume 500 uL. In control reaction, recombinant p300mut was used. Acetylation was then checked with WB (see FIG. 10).

Procedure

Co-Immunoprecipitation experiments were performed between either purified His-tagged Acetyl-integrase (acetylated with p300 in vitro) or His-Integrase and bacterial cell [*E. coli* BL21 (DE3)] extract expressing VH-112A-HA (with appropriate controls, see FIG. 11). 250 uL (ca. 1900 ug) of VH-112A-HA cell extract was incubated with 50 uL of Pierce Anti-HA Agarose resin for 1.5h at 4° C. on a rotating wheel. Then, samples were centrifuged at 700 rcf and washed twice with 400 uL of HAT Buffer 1× (by BPSBioscience, TBS-based buffer). Successively, 4.8 ug of appropriate antigen (Acetylated, non-acetylated or control) was added to the tube and incubated on the wheel at 4° C. for additional 2h in a final volume of HAT buffer of 400 uL. At this point, samples are washed twice with 500 uL HAT buffer and twice with TBS-T 0.1% tween-20 (4 times total). All centrifugations were performed at 700rcf, 2 min, 4° C. Resins were then boiled for 5 min in 2× Laemmli buffer. Before loading samples on Acrylamide gel, samples were spun at 14,000 rcf for 2 min to pellet resin. SDS-PAGE was followed by W.B. using anti-His mouse monoclonal "Penta" antibody (Qiagen) to see co-precipitation and anti-HA rat monoclonal antibody (Roche, clone 3F10) to confirm intrabody presence.

In Vitro Detection of Integrase Through VH-HA Intrabodies

Purified His-Ac-Integrase or His-Integrase were used to coat wells from a 96-w plate at the concentration of 10 ng/uL, O/N 4° C., in carbonate buffer pH 9.6. After coating, 1 h blocking at 37° C. occurred (BSA 10 mg/mL) in PBST 0.05%. fresh cell extract containing VH-HA intrabodies was used to "capture" the HA-tagged prey. Cell extract was diluted in PBST/BSA 3% 2h at 37 C. Detection of retained intrabody domain was performed with anti-HA-HRP antibody (Roche), after 1 h incubation at 37° C. IN PBST/BSA 3%, with TMB. On the same plate the secondary HRP antibody alone was not able to recognize coated antigens. Wavelength read was 450 nm. In vitro, VH 12A seems to recognize sensibly better non-acetylated integrase. Washes between steps were 4× in PBST. (FIG. 13)

Anti Acetyl Histone H3

In Vitro Detection of H3 Acetylated Peptides with Cobalt Resin-Purified his-ScFv58F 58F scfv was subcloned in pGIO1 (C-term V5 and His tag) and expressed in BL21cells [BL21(DE3)]. Proteins from cell pellet were extracted as before for VH intrabodies using binding buffer (Tris 50 mM, NaCl 150 mM, Complete Mini Roche EDTA-free, PMSF 1 mM) pH8.5. Cell extract was incubated with TALON resin for 2h at 4° C. on rotating wheel. Resin was previously equilibrated with the same buffer (2 500 uL washes). Follow 2 washes of ten minutes on wheel at 4° C. with binding buffer+5 mM Imidazole. Elution is performed with 200 mM Imidazole in binding buffer. Purified intrabody concentration was evaluated with Bradford assay and colorimetric comparison of run bands after SDS-PAGE/Coomassie staining.

E.L.I.S.A. was then performed in 96-well plate. Several acetylated and non-acetylated H3 yeast peptides have been used to coat plate (10 uM). Sequences were chosen from the yeast bait we have used for selections representing aa 1-21 or 10-29, and AcLys are the literature-illustrated PTM catalysed by Gcn5 on H3 N-term. Coating was verified with commercial anti-H3 and anti-AcH3 antibodies. List of the antigens:

```
H3#1:
                                  (SEQ ID NO: 4)
ARTKQTARKSTGGKAPRKQLA

H3#2:
                                  (SEQ ID NO: 5)
ARTKQTAR(AcK)STGG(AcK)APRKQLA

H3#3:
                                  (SEQ ID NO: 6)
ARTKQTAR(AcK)STGGKAPRKQLA

H3#4:
                                  (SEQ ID NO: 7)
ARTKQTARKSTGG(AcK)APRKQLA

H3#5:
                                  (SEQ ID NO: 8)
ARTKQTARKSTGGKAPR(AcK)QLA

H3#6:
                                  (SEQ ID NO: 9)
STGGKAPRKQLASKAARKSA

H3#7:
                                  (SEQ ID NO: 10)
STGGKAPRKQLAS(AcK)AARKSA

H3#8:
                                  (SEQ ID NO: 11)
STGGKAPRKQLASKAAR(AcK)SA
```

After O/N coating at 4° C. in carbonate buffer, listed antigens were blocked in BSA 10 mg/mL for 1 h 37° C. Then, they were incubated with 58F-His (about 10 ng/uL) in TBST/BSA 3% for 2.5h at 37° C.; follows 1 h incubation with anti-His Penta (mouse) and 1 h incubation with anti-mouse-HRP antibody. All dilution buffers were TBST 0.05% pH8.5. Antibody dilutions were made in TBST/BSA 3% buffer pH 8.5. Washes between steps 3×, final 5× in TBST pH 8.5. Anti-His Penta and anti-Mouse-HRP are not able to recognize coated antigens. Anti-Mouse-HRP antibody is not able to detect 58F-His.

The only form the intrabody could recognize specifically was peptide #3, that has AcK9 only. Acetylation of lysine 9 is an important modification for histone code, related to gene expression. Interestingly, very slight cross reaction is observed with AcK9/AcK14 form. (FIG. 14)

MODified Histone Peptide Array (Dot Blot)

To evaluate cross-reactivity of ScFv-58F against other PTM forms of histone H3 and against other histones, a dot blot array with more than 300 differently modifies histone peptides was probed with ScFv-58F-HA (FIG. 15). Results show that ScFv-58F is specific for acetylated lysine 9 of histone H3 and does not cross-react with any other acetylated, phosphorylated or methylated residue of histone H3, nor with any other histone protein. The HA-tagged antibody domain was purified by FPLC using an ionic exchange column. MODified Histone assay (Active Motif cat. No. 13001) was performed with FPLC-purified ScFv-58F-HA using standard western blot technique according to manufacturer's instructions. Briefly, ScFv-58F-HA was incubated o/n at 2 uM concentration in TBS, then detected with anti-HA antibody (Roche, 1:1000) and anti-Rat-HRP antibody (SCBT, 1:1000). Washes were made with TBS-T 0.05%.

ScFv-58F Specifically Binds and Immunoprecipitates Recombinant Native Acetylated Histone H3 In Vitro ScFv-58F-HA was used to immunoprecipitate recombinant version of Histone H3 that was acetylated in vitro by Gcn5 enzyme (Active Motif cat. no 31204). FIG. 16 shows how 58F intrabody strongly immunoprecipitates the acetylated version of the native protein and has only a neglectable interaction with the unmodified histone, which is comparable to background observed with an anti-H3Ac commercial antibody (right-bottom panel) in western blots. Also, by controlling the concentration of ScFv-58F under 2 uM, as shown in next paragraph, it is possible to obtain a net recognition of acetylated histone H3 over the non-acetylated form. Co-immunoprecipitation assay was performed as follows: ScFv-58F-HA was expressed in bacteria using appropriate pGIO1 plasmid by induction of OD600=0.6 LB+Kanamycin E. coli BL21(DE3) culture with 0.5 mM IPTG, for 4.5h at 25° C., 225 rpm. Bacterial pellet is then lysed in lysis buffer (Tris 20 mM pH 8.0, NaCl 150 mM, EDTA 1 mM, lysozyme 1 mg/mL, PMSF 1 mM, complete Mini EDTA-free 1×). 250 µL ScFv-HA cell extract were added to 40 µL of anti-HA agarose (Thermo Scientific), and incubated on a rotating platform for 1.5h at 4° C. This will purify the intrabody. Resin is washed once with ice-cold lysis buffer minus lysozyme and 2 times with 400 µL of ice-cold HAT buffer 1× (BPS bioscience). Antigen is then added to the resin (ca. 15 µg for Integrase and 2 µg for Histone H3) and 250 µL of HAT buffer 1× are also added. Control samples are also prepared to verify specific binding of antigen to the intrabody. Samples are incubated with rotation for 2h at 4° C. Immunoprecipitates are washed twice with 500 µL of HAT buffer 1× and twice with 500 µL with TBS-T 0.1%. Resins are boiled in loading buffer for SDS-PAGE/western blot analysis.

ScFv-58F Binding Curves to Evaluate Affinity to Native Acetylated H3 Histone and Acetylated H3 Peptides ScFv-58F-HA was employed in ELISA assay to quantitatively evaluate binding affinity and binding preferentiality against recombinant native H3 and H3 peptides (either acetylated or unmodified). Firstly, a direct-ELISA binding curve showed that the antibody domain loses its weak cross-reaction against the unmodified peptide if the concentration is lower than 2 micromolar (FIG. 17a). Then, the same assay was conducted using the recombinant, in vitro-acetylated H3 and the acetylated K9 peptide, demonstrating that 58F preferentially binds the native form of the antigen (FIG. 17b). 96-well plate was coated overnight with appropriate antigen at the concentration of 10 uM. Antibody dilutions are indicated in the figure legend.

ScFv-58F Binds Acetylated H3 In Vivo, Detects Chromatin of Yeast and Mammalian Cells, and Reduces Availability of Acetylated H3 in Yeast Cells.

To evaluate binding of ScFv-58F to endogenous protein, stable yeast lines intracellularly expressing the anti-AcK9H3 intrabody (IE-ScFv-58F-HA) or an unrelated control intrabody (IE-ScFv-112A-HA and/or IE-2-VP16 (IE-2-VP16 is identified with the ScFv-2 anti-Tau intrabody isolated in Visintin et al—"The Intracellular Antibody Capture Technology (IACT): Towards a Consensus Sequence for Intracellular Antibodies"—Journal of Molecular Biology—2002) or no intrabody (L40) in the nucleus, were used to prepare chromatin solutions for a chromatin immunoprecipitation experiment. In keeping with previous results, ScFv-58F binds yeast acetylated H3 also in vivo, since it is able to immunoprecipitate it after cell lysis and chromatin sonication (FIG. 18a). Moreover, IE-ScFv-58F is able to reduce acetylated histone availability in chromatin. Indeed, recognition of AcK9H3, as well as of associated chromatin, by exogenously-added anti-AcK9H3 polyclonal antibody, is almost totally impaired in extracts from cells expressing the ScFv-58F intrabody, further indicating that IE-ScFv-58F binds AcH3 in vivo and subtracts it from the chromatin pool that can be subsequently immunoprecipitated (FIG. 18b). Furthermore, the minor availability of acetylated chromatin in ScFv-58F-expressing samples is not dependent on an intrinsic feature of the used yeast, as the level of acetylated histones is the same for all the samples (FIG. 18c). These results were particularly important to define the possibility to assess the role of intrabody functionality on cellular protein network. To assess reactivity with human cell chromatin, FPLC-purified ScFv-58F-HA was used to perform an immunofluorescence on HeLa cells (FIG. 18d). Notably, the anti-AcK9H3 antibody domain is able to give a net euchromatic staining of the nuclei, which does not overlap with perinuclear lamin staining.

Immunofluorescence protocol: Fixation: HeLa cells were fixed in 2% PFA for 12' RT. Antigen retrieval: 3N HCl for 45' RT. 1× wash with 0.1M tetraborate buffer pH 8.5 for 10' RT. 2× wash with PBS 10' RT. Blocking: PBS+BSA 1%+Triton-x-100 0.3% for 1 h at RT. Antibody I: ScFv-58F-HA 450 ng/uL in PBS/BSA o/n 4° C.; Lamin A Antibody (C-20): sc-6214 1:200 o/n 4° C. 3× washes PBS/BSA 10' each RT. Antibody II: anti-HA Roche 1:500 or donkey anti-goat Alexa Fluor 633, 1 h RT. 3× washes PBS/BSA 10' each RT. Antibody III: anti-Rat Alexa Fluor 488, 1:500. 3× washes. 3× washes PBS/BSA 10' each RT. Imaging by Leica confocal microscopes.

Chromatin immunoprecipitation was performed as follows: yeast carrying pLinker220-ScFv-58F-HA or control plasmids were grown for 2 overnights in SD-L (lacking leucine) medium, then from OD600=0.3 to 0.65 in YPD (50 mL culture). Cells were spun at 2,000×g and washed 3 times with 30 mL of TBS, then resuspended in 1 mL TBS, spun again and pellet was frozen to −80° C. Day after cells were lysed in TBS-EDTA (IP buffer) using acid-washed glass beads (Sigma, cat. No G8772) and protease inhibitors (Roche cOmplete mini)+PMSF 1×. Lysates were transferred in new tubes and sonicated with Bioruptor™ (Diagenode) for 15 min cycle, high frequency at 4° C. and chromatin checked on 1.5% agarose gel (smear peak around 1000 bp). IP was conducted with anti-HA agarose (Thermo Scientific) o/n at 4° C. or with primary antibody+proteinG. Day after samples are washed 4 times with IP buffer+tween 0.05% for protein samples and 2 times for DNA samples followed by LiCl buffer and TE 1×. DNA IP samples were eluted in NaHCO3 0.1M/SDS 1% RT for 30 min. Proteinase K was added and DNA was extracted by Phenol/Chloroform/Isoamyl alcohol (25/24/1). Precipitation is done o/n at −20° C. with absolute ethanol, pellets were washed with 70% ethanol and resuspended in 1×TE. Quantification was done with Invitrogen Q bit. Protein samples were instead boiled with resins after washing.

Functional Assays

Reduction of Viral Infectivity Upon VH-112A and VH-12A Administration

Acetylation of HIV-1 Integrase is known to enhance viral integration and infectivity (Cereseto et al.—EMBO Journal 2005). Since VH-112A specifically targets acetyl-Integrase while VH-12X (herein also referred as VH-12A) is an acetylation-independent Integrase binder, we compared their efficacy in an HIV-1 infectivity assay, to investigate possible effects of a specific anti-AcIN interference. HeLa cells transfected with either anti-Integrase intrabody, were infected, 48 hours later, with an HIV virus carrying a GFP reporter gene. Controls included cells transfected with an unrelated VH domain or with the plasmid backbone. The acetylation-specific cytoplasmic VH-112A intrabody significantly inhibits infectivity with respect to a non-related intrabody ($p<0.05$, VH-2), to the backbone ($p<0.05$), to non-transfected cells ($p<0.001$, CTRL+) or, also with respect to VH-12X ($p<0.05$) (FIG. 19a). The greater effectiveness of VH-112A, with respect to VH-12X in reducing the infectivity, highlights the importance of specifically targeting acetylated Integrase. Indeed, although VH-12X also showed a reduced infectivity when compared to the same controls, this reduction is significant with a lower confidence interval (FIG. 19a). To further confirm that inhibition of integration is due to interaction provided by VH-112A-HA and VH-12X-HA with (acetylated) Integrase, we set a co-immunoprecipitation experiment in the same cellular system where the Infectivity Assay was performed. Stable HeLa cell lines expressing HA-tagged anti-Ac-Integrase, anti-Integrase and anti-Tau (VH2) intrabodies were created. Then, these lines were transfected with Flagged constructs bearing either a wild type version of the Integrase, which is acetylated in mammalian cells by P30086, or a mutated, non-acetylated version of the protein. Western Blot in FIG. 19b clearly shows how the interaction profile of both the intrabodies is in keeping with results obtained in vitro, and confirms a significant intracellular interaction between the viral enzyme and the two single domains.

Altogether, the data demonstrate that targeting single PTM with PISA intrabodies leads to a significant and biologically relevant functional effect.

Procedure: HeLa cells were maintained in DMEM (GIBCO) supplemented with 10% FCS. The day before the experiment cells were seeded at $2\times10^5$ cells per well in six-well plates. The lipofection was carried out with Effectene (QIAGEN) according to manufacturer's instructions. Cells have been transfected with 400 ng of pScFvExHA-VH-112A-HA, VH-12X-HA or VH-2-HA plasmids. After 48h, cells have been transduced with the pWPXLD vector containing a GFP reporter. 48h post-transduction, cells have been analyzed by FACS to measure infection efficiency by GFP fluorescence intensity. Intrabody expression was checked by WB on Bradford-quantified cell lysates. Immunoprecipitation was conducted on fresh cell extract overnight, using anti-HA agarose from Pierce.

Functional Validation of ScFv-58F: A Transcriptomic Study

Histone acetylation on lysine 9 is known to strongly regulate chromatin and transcription (Jenuwein et al—Science 2001). Therefore, we investigated which were the functional consequences of the expression of an anti-AcK9H3 binder in vivo. Indeed, masking AcK9H3 binding site in cells might avoid many bromodomain-containing proteins, which regulate chromatin, to bind their target and hence promote or regulate gene expression. We therefore sought to determine, by microarray analysis, the effects of ScFv-58F expression on the cell transcriptome, compared to the unrelated ScFv-112A and to untransfected L40 yeast. ScFv-112A represents a very strict control as it binds an acetylated antigen. PCA analysis showed that biological replicates of each of the three samples clusterize in well separated groups (FIG. 20a). We set analysis filters to understand if there was a set of genes that is specifically regulated by ScFv-58F. First of all, a threshold of minimum 1.5 in fold change was set. Secondly, genes were selected by their statistical significance (Padj<0.05, where Padj is the P value adjusted for the Benjamini correction) between ScFv-58F and ScFv-112A. These genes are also non-significant (PAdj>=0.05) between ScFv-112A and non transfected L40 strain, which allows to discriminate the general effect of any antibody domain expressed intracellularly. A heatmap was then constructed with resulting hits to show comparisons of the interesting genes between ScFv-58F and ScFv-112A. Data were normalised on L40 samples. Approximately one hundred mRNAs were selectively regulated in a statistically significant way by ScFv-58F, with a greater number of downregulated genes (FIG. 20b). The higher number of downregulated genes demonstrate the effect of silencing by the anti-acetyl-H3 intrabody. Gene onthology (GO) enrichment analysis of these mRNAs was performed with online software David Ontology, and showed that the most affected GO terms include ion transport, phosphorus metabolism, oxidative phosphorylation, mitochondrial membrane, and ribosomal processing (FIG. 20c). A subset of the most significant hits was validated by Real-Time qPCR performed on the original RNA extracted from each sample, replicating with high grade of statistical significance the results obtained in the microarray (FIG. 20d). According to what found in Gene Ontology terms, among our most significant hits illustrated in the heatmap of FIG. 20b, we found PHO84 and PHO89, which are genes involved in the phospate transport and metabolism. PHO genes are known to be strongly regulated by histone acetylation levels in yeast (Wongwisansri wt al.—Eukaryotic cell 2005). Indeed, PHOS and related PH084 and PH089 transcripts increase both by low levels of intracellular phospate and both by depletion of RPD3 histone deacetylase. An augmented acetylation level allows chromatin remodelers like Snf2 to expose these genes to increased transcription. Thus, conditions in which histone acetylation is lower should correlate with a decreased expression of these genes. In our case, ScFv-58F intrabody is binding to Histone AcK9H3, silencing the action of acetylated chromatin. Notably, other genes we identified like the most strongly silenced can be correlated to histone acetylation, as found by previous authors for CTR1 (Wan et al.—FEBS Letter 2011). Finally, many genes and Gene Ontology categories found as the most significant hits are strictly related with each other, such as Phosphate metabolism genes and NAD+, ATP metabolism and mithocondria, indicating a possible indirect effect caused by the modulation of PHO genes. Thus, the intracellular interference with AcK9H3 by ScFv-58F did have significant functional consequences on the transcriptome and the effect observed is mainly classified as a silencing effect. This is the first evidence of a biological functional effect at a global transcriptomic level mediated by single-PTM inhibition in a living cellular system, which can only be provided by the described method.

Microarray yeast samples were processed as follows: Yeast glycerol stocks are restreaked on fresh plates (YPD for L40 wild type and SD-Leu for 112A and 58F) and incubated at 30° C. for 3d. A single CFU is inoculated in 10 mL liquid culture with appropriate medium and shaked at 240 rpm at 30° C. overnight. Next day 1 mL of culture is used to inoculate a larger culture of 50 mL (using L40 or SD-Leu accordingly) and shaked at 240 rpm O/N at 30° C. Next day cultures are diluted in 50 mL to OD600=0.2 in YPD and incubated O/N at 30° C. with shaking 240 rpm. Next day yeast is centrifuged (5 min 3,000×g) and total RNA is extracted using Yeast RiboPure® kit by ThermoFisher, which allows purification of total RNA without overload of ribosomal RNA. RNA quality is initially evaluated on DEPC/MOPS/formamide 1% agarose gel and with nano-drop measurement. Moreover, RNA was also checked using the Agilent BioAnalyzer 2100 (Agilent RNA 6000 nano kit): samples with a RNA Integrity Number (RIN) index lower than 8.0 were discarded. All the experimental steps involving the labelling, hybridization and washing of the samples were done following the one-color Agilent protocol.

PISA Selections Against Phospho-Tau Bait

Tau protein stabilizes microtubules, and it is abundant in neurons of the central nervous system and are less common elsewhere, but are also expressed at very low levels in CNS astrocytes and oligodendrocytes. Pathologies and dementias of the nervous system such as Alzheimer's disease and Parkinson's disease (Lei et al—Int Journ Biochem Cell Biol 2010) are associated with tau proteins that have become defective and no longer stabilize microtubules properly.

Hyperphosphorylation of the tau protein by GSKβ and other kinases can result in the self-assembly of tangles of paired helical filaments and straight filaments, which are involved in the pathogenesis of Alzheimer's disease, frontotemporal dementia, and other tauopathies (Alonso et al.— PNAS 2001). However, no current available chemical that inhibit Tau is able to distinguish between the differently phosphorylated versions of the protein. This task is exclusively achievable with PISA intrabodies and will help to study the biology of phospho-Tau and its clinical significance, besides being a potential new and powerful inhibitor for therapeutic usage.

PISA tethered catalysis bait panel encoding phosphorylated Tau protein has been created, and stable yeast bait lines have been established. (FIG. 21). Tau full-length protein coding sequence (NCBI accession number: KR711804) has been fused at the N-terminus of either GSK3P kinase (NCBI accession number: BC012760), which is a constitutively activated mutant version bearing the S9A mutation, or at N terminus of the GSK3β K85A mutant, which instead is not able to catalyse the phosphorylation of Tau. Protein target/ kinase fusion is also fused with LexA DNA binding domain at the N-terminus and with HA tag at the very C-terminus, as illustrated in FIG. 21.

Bait was constructed using classic cloning techniques (PCR amplifications, overlap PCR and restriction enzyme cut/ligations). PISA selections were performed as described above for acetylated baits, and yielded about one hundred of positive intrabody clones (primary screening selection), prior to the secondary selection, which led to the finally selected anti phosphoTau intrabodies.

Construction of the First Human Single Domain VH and Scfv SPLINT Library

In addition to the scFv antibody domains, which have been described above, single domain antibodies (e.g. either Variable Heavy or Variable Light domain only of an Immunoglobulin) are a popular recombinant antibody format widely used in in vitro display technologies [e.g. camelid single domains, also called "nanobodies" (Helma et al—The Journal of Cell Biology 2015)].

Despite the fact that single antibody domains would be very useful as intrabodies, due to their small size, their derivation from a naïve human library has never been reported, since it would be anticipated that human single domain antibodies (VH or VL) would not have an affinity sufficiently high for practical uses. For this reason, the possibility of exploiting the natural human IgM repertoire has never been explored for naïve SPLINT libraries of VH domains, since it is expected that good binders would not be isolated successfully. Indeed, Human single domain antibodies have been sofar isolated by IACT selection only from synthetic libraries, (Tanaka et al—Journal of Molecular Biology 2003), made from a fixed scaffold with random variability on the third Complementarity Determining Region (CDR3). Two SPLINT human libraries, one in the ScFv format and one in the single VH domain format, were constructed and screened against PISA baits described in this document as well as against a number of other different antigens in IACT selections. Surprisingly, we obtained the unexpected result that true positive intrabodies could be de novo selected not only from the human SPLINT scFv library but also, unexpectedly and against the predictions, from the naïve SPLINT library of human single VH domains. Thus, VH domains were successfully selected from naïve SPLINT VH library against various antigens, including the extracellular fragment of Neuroligin 3 and Cytochrome C and against PTM proteins. Deep sequencing analysis of the libraries showed that the naïve scFv and VH human SPLINT libraries have high quality and diversity ($>10^7$ for the scFvs and $>6\times10^6$ for VHs respectively).

A scheme of the construction procedure is described in FIG. 22.

Construction of Human SPLINT ScFv Libraries

Antibody domain libraries have been generated from human lymphocytes extracted from peripheral blood (PBLs). PBLs were isolated from blood buffy coat of four voluntary donors with Ficoll-Paque. More than $10^8$ PBLs have been subjected to RNA extraction with trizol reagent, then antibody IgM (heavy and light chains) were retro-transcribed with specific oligos annealing in the constant region. After cDNA was obtained, VH and VL (both kappa and λ) regions were amplified by PCR with a specific set of primers extensively modified and optimised from Marks and Bradbury (Methods in Molecular Biology 2004). These oligos are able to anneal at the beginning of the external framework regions of the V genes, producing a "blunt" product, with virtually no possibilities of overlap. To amplified VHs were used 6 oligos for the 5', and 4 oligos for the 3'. Every possible combination of these primers was used generating 24 different classes of VHs. To amplify Vks were used 6 oligos for the 5', and 5 oligos for the 3'. Every possible combination of these primers was used generating 30 different classes of VKs. To amplify Vλs were used 7 oligos for the 5', and 3 oligos for the 3'. Every possible combination of these primers was used, generating twenty-one different classes of Vλs.

At this point, VH regions were joined to Vk and Vλ, through a process called "pullthrough". To this aim, a (G4S)3 linker of 45 bp was amplified from a pre-existing plasmid using a new set of primers, with the same 3' region annealing on the linker, and different protruding 5', overlapping perfectly either with VH framework4 or VL framework1. This amplification generates a "semi-blunt" product mix, that is able to overlap to VH or VL only. Third step consists in overlap PCR between the Variable region amplicons and the semi-blunt linkers, resulting in VH and VL protruding with the same linker sequence at 3' and 5' respectively.

The fourth step is made by joining VH-linker and linker-VL products in a final overlapping PCR. After a few cycles, primers for the 5' of VHs bearing restriction site for NheI and primers for the 3' of Vks or Vλs bearing restriction site for BssHII were added to the mix, generating the final 750 bp scFv product. Finally the pullthrough products were digested with NheI/BssHII enzymes and ligated to the NheI/BssHII digested vector pLinker220.

Construction of Human SPLINT VH Library

The starting RNA was the same used for hscFV1 library. Amplification of VH subclasses was performed using in a single reaction a mix of the 6 primers for the 5' (bearing BssHII restriction site) and of the 4 primers for the 3' (bearing NheI restriction site) specific for VH. VH products were digested with BssHII/NheI enzymes and ligated to the BssHII/NheI digested vector pLinker220. Transformation efficiency was assessed as described before and resulted to be 6×10$^6$. Transformed bacteria were inoculated in LB-SeaPrep Agarose (Lonza Rockland, Inc.) as described in Elsaesser 72. Plasmids were extracted with Qiagen Plasmid Giga Kit.

Primers Used for cDNA Amplification

```
HuCkFOR:
                                         (SEQ ID NO: 22)
5' AGACTCTCCCCTGTTGAAGCTCTT 3'

HuCLFOR:
                                         (SEQ ID NO: 23)
5' TGAAGATTCTGTAGGGGCCACTGTCTT 3'
```

Primers Used for Library Construction
Primers for VH

```
BssHII-HuVH1aBACK:
                                         (SEQ ID NO: 24)
5' gCCgcgcgcatgccCAGGTGCAGCTGGTGCAGTCTGG 3'

BssHII-HuVH2aBACK:
                                         (SEQ ID NO: 25)
5' gCCgcgcgcatgccCAGGTCAACTTAAGGGAGTCTGG 3'

BssHII-HuVH3aBACK:
                                         (SEQ ID NO: 26)
5' gCCgcgcgcatgccGAGGTGCAGCTGGTGGAGTCTGG 3'

BssHII-HuVH4aBACK:
                                         (SEQ ID NO: 27)
5' gCCgcgcgcatgccCAGGTGCAGCTGCAGGAGTCGGG 3'

BssHII-HuVH5aBACK:
                                         (SEQ ID NO: 28)
5' gCCgcgcgcatgccGAGGTGCAGCTGTTGCAGTCTGC 3'

BssHII-HuVH6aBACK:
                                         (SEQ ID NO: 29)
5' gCCgcgcgcatgccCAGGTACAGCTGCAGCAGTCAGG 3'

HuJH1-2FOR:
                                         (SEQ ID NO: 30)
5' TGAGGAGACGGTGACCAGGGTGCC 3'

HuJH3FOR:
                                         (SEQ ID NO: 31)
5' TGAAGAGACGGTGACCATTGTCCC 3'

HuJH4-5FOR:
                                         (SEQ ID NO: 32)
5' TGAGGAGACGGTGACCAGGGTTCC 3'

HuJH6FOR:
                                         (SEQ ID NO: 33)
5' TGAGGAGACGGTGACCGTGGTCCC 3'
```

Primers for hVH Single Domain Library

```
NheI-HuJH 1-2 FOR:
                                         (SEQ ID NO: 34)
5' CGGCCGCGCTAGCTGAGGAGACGGTGACCAGGGTGCC 3'

NheI-HuJH 3 FOR:
                                         (SEQ ID NO: 35)
5' CGGCCGCGCTAGCTGAAGAGACGGTGACCATTGTCCC 3'

NheI-HuJH 4-5 FOR:
                                         (SEQ ID NO: 36)
5' CGGCCGCGCTAGCTGAGGAGACGGTGACCAGGGTTCC 3'

NheI-HuJH 6 FOR:
                                         (SEQ ID NO: 37)
5' CGGCCGCGCTAGCTGAGGAGACGGTGACCGTGGTCCC 3'
```

Primers for Vk

```
HuVκ1aBACK:
                                         (SEQ ID NO: 38)
5' GACATCCAGATGACCCAGTCTCC 3'

HuVκ2aBACK:
                                         (SEQ ID NO: 39)
5' GATGTTGTGATGACTCAGTCTCC 3'

HuVκ3aBACK:
                                         (SEQ ID NO: 40)
5' GAAATTGTGTTGACGCAGTCTCC 3'

HuVκ4aBACK:
                                         (SEQ ID NO: 41)
5' GACATCGTGATGACCCAGTCTCC 3'

HuVκ5aBACK:
                                         (SEQ ID NO: 42)
5' GAAACGACACTCACGCAGTCTCC 3'

HuVκ6aBACK:
                                         (SEQ ID NO: 43)
5' GAAATTGTGCTGACTCAGTCTCC 3'

NheI-HuJκ1FOR:
                                         (SEQ ID NO: 44)
5' CGGCCGCgctagcACGTTTGATTTCCACCTTGGTCCC 3'

NheI-HuJκ2FOR:
                                         (SEQ ID NO: 45)
5' CGGCCGCgctagcACGTTTGATCTCCAGCTTGGTCCC 3'

NheI-HuJκ3FOR:
                                         (SEQ ID NO: 46)
5' CGGCCGCgctagcACGTTTGATATCCACTTTGGTCCC 3'

NheI-HuJκ4FOR:
                                         (SEQ ID NO: 47)
5' CGGCCGCgctagcACGTTTGATCTCCACCTTGGTCCC 3'

NheI-HuJκ5FOR:
                                         (SEQ ID NO: 48)
5' CGGCCGCgctagcACGTTTAATCTCCAGTCGTGTCCC 3'
```

Primers for Vλ

```
HuVλ1BACK:
                                         (SEQ ID NO: 49)
5' CAGTCTGTGTTGACGCAGCCGCC 3'

HuVλ2BACK:
                                         (SEQ ID NO: 50)
5' CAGTCTGCCCTGACTCAGCCTGC 3'

HuVλ3BACK:
                                         (SEQ ID NO: 51)
5' TCCTATGTGCTGACTCAGCCACC 3'

HuVλ3bBACK:
                                         (SEQ ID NO: 52)
5' TCTTCTGAGCTGACTCAGGACCC 3'
```

```
HuVλ4bBACK:
                                            (SEQ ID NO: 53)
5' CACGTTATACTGACTCAACCGCC 3'

HuVλ5BACK:
                                            (SEQ ID NO: 54)
5' CAGGCTGTGCTCACTCAGCCGTC 3'

HuVλ6BACK:
                                            (SEQ ID NO: 55)
5' AATTTTATGCTGACTCAGCCCCA 3'

NheI-HuJλ1FOR:
                                            (SEQ ID NO: 56)
5' CGGCCGCgctagcACCTAGGACGGTGACCTTGGTCCC 3'

NheI-HuJλ2-3FOR:
                                            (SEQ ID NO: 57)
5' CGGCCGCgctagcACCTAGGACGGTCAGCTTGGTCCC 3'

NheI-HuJλ4-5FOR:
                                            (SEQ ID NO: 58)
5' CGGCCGCgctagcACCTAAAACGGTGAGCTGGGTCCC 3'
```

Primers for Linkers

```
PlusLinker(G4S)3:
                                            (SEQ ID NO: 59)
5' GGTGGAGGCGGTTCAGGCGGAG 3'

MinusLinker(G4S)3:
                                            (SEQ ID NO: 60)
5' CGATCCGCCACCGCCAGAGCCAC 3'

RHuJH1-2:
                                            (SEQ ID NO: 61)
5' GCACCCTGGTCACCGTCTCCTCAGGTGG 3'

RHuJH3:
                                            (SEQ ID NO: 62)
5' GGACAATGGTCACCGTCTCTTCAGGTGG 3'

RHuJH4-5:
                                            (SEQ ID NO: 63)
5' GAACCCTGGTCACCGTCTCCTCAGGTGG 3'

RHuJH6mod:
                                            (SEQ ID NO: 64)
5' GGACCACGGTCACCGTCTCCTCAGGTGG 3'

RHuVκ1aBACKFv:
                                            (SEQ ID NO: 65)
5' GGAGACTGGGTCATCTGGATGTCCGATCCGCC 3'

RHuVκ2aBACKFv:
                                            (SEQ ID NO: 66)
5' GGAGACTGAGTCATCACAACATCCGATCCGCC 3'

RHuVκ3aBACKFv:
                                            (SEQ ID NO: 67)
5' GGAGACTGCGTCAACACAATTTCCGATCCGCC 3'

RHuVκ4aBACKFv:
                                            (SEQ ID NO: 68)
5' GGAGACTGGGTCATCACGATGTCCGATCCGCC 3'

RHuVκ5aBACKFv:
                                            (SEQ ID NO: 69)
5' GGAGACTGCGTGAGTGTCGTTTCCGATCCGCC 3'

RHuVκ6aBACKFv:
                                            (SEQ ID NO: 70)
5' GGAGACTGAGTCAGCACAATTTCCGATCCGCC 3'

RHuVλBACK1Fv:
                                            (SEQ ID NO: 71)
5' GGCGGCTGCGTCAACACAGACTGCGATCCGCCACCGCCAGAG 3'

RHuVλBACK2Fv:
                                            (SEQ ID NO: 72)
5' GCAGGCTGAGTCAGAGCAGACTGCGATCCGCCACCGCCAGAG 3'

RHuVλBACK3aFv:
                                            (SEQ ID NO: 73)
5' GGTGGCTGAGTCAGCACATAGGACGATCCGCCACCGCCAGAG 3'

RHuVλBACK3bFv:
                                            (SEQ ID NO: 74)
5' GGGTCCTGAGTCAGCTCAGAAGACGATCCGCCACCGCCAGAG 3'

RHuVλBACK4Fv:
                                            (SEQ ID NO: 75)
5' GGCGGTTGAGTCAGTATAACGTGCGATCCGCCACCGCCAGAG 3'

RHuVλBACK5Fv:
                                            (SEQ ID NO: 76)
5' GACGGCTGAGTCAGCACAGACTGCGATCCGCCACCGCCAGAG 3'

RHuVλBACK6Fv:
                                            (SEQ ID NO: 77)
5' TGGGGCTGAGTCAGCATAAAATTCGATCCGCCACCGCCAGAG 3'
```

Applications

IntraChIP and Anti-Histones Intrabodies

Currently, first step towards functional validation and first application using 58F intrabody (anti-H3Ac) have been made. An HA tag has been added to c-term of pLinker-58F plasmid, the yeast expression vector used for selection. This will avail easy tracking and manipulation of the intrabody in yeast L40 cells and other strains.

One of the most important applications envisaged for an anti-Histone antibody is surely Chromatin Immunoprecipitation (ChIP). Normally, ChIP is performed by firstly cross-linking chromatin with paraformaldehyde. Then, cells are lysed, DNA is sonicated, and finally chromatin is immunoprecipitated with antibodies to Histones or a particular transcription factor. However, formaldehyde used before antibody probe could alter Histone Lysines creating an analysis bias; crosslinking is empirical, poorly understood mechanism (Gavrilov, 2014). Manipulating chromatin before immunoprecipitation, could thus lead to loss of information and/or biases in obtained information.

By using our 58F intrabody, we aim to investigate if a consistent improvement of IP can occur. The idea is that of expressing the anti-AcH3 intrabody as a first thing within yeast and then proceed with IP protocol. We called the application, for this reason, "IntraChIP". Replication of a well-studied yeast IP case will help to compare gene reads from classic IP and our IntraChIP version. Comparison can be done between 58F used as intrabody, 58F purified and used as normal, "external" antibody, and a commercial antibody. Since H3K9 acetylation is associated with DNA transcription, any exclusive IntraChIP gene read can be validated checking for RNA levels associated to that gene.

Moreover, anti-AcH3 intrabodies can be seen as novel tools to study histone code and the "epigenetic fingerprint" of living cells. Perturbation induced by chemicals to alter chromatin are often obtained by targeting modifying enzymes, which easily leads to consequent perturbations of other downstream pathways. By targeting chromatin from inside, the real epigenetic state of a cell in a determined condition can be targeted and, eventually, manipulated directly. First evidences of intrabodies used to localize histones in living cell has already been shown (Sato et al., 2013), but by previously selected antibodies, which functions only in particular cases. For this reason, stunning scientific interest is behind having a general intrabody selection platform against PTM histones and PTM in general.

Target Validation and Therapeutic Applications

PTModifications play an important role in pathological processes too. A peculiar example is that of Integrase of HIV-1 (which may be represented by the sequence of NCBI Accession number AF029884.1 or fragments thereof). Indeed, it is known that acetylation by p300 (which may be represented by the sequence of gene id 2033 or fragments thereof) enzyme is crucial for integration of viral genome in the host genome (Cereseto et al., 2005). Moreover, epigenetic of tumors has shown that important chromatin remodeling can occur instead of simple gene mutation, and tools for chromatin targeting and remodeling are needed (Siddiqi et al, 2010; Beltran et al., 2008).

In both cases, therefore, these and other PISA antibodies could play an important role in target validation studies and therapeutic applications. In general, the ability to perform PTM-selective and PTM-specific protein interference studies in living cells with the isolated anti PTM intrabodies is novel and would be extremely useful as a generic tool for target validation and for therapeutic purposes. Also, the isolated antibodies are very useful as "macrodrugs", i.e. as protein templates with a specificity for a given PTM, that can be used as a lead to isolate chemical small molecules with similar PTM specificity.

Intracellular protein networks are complex webs of protein-protein interactions, in which the proteins are nodes of the network and the protein-protein interactions are the edges. PTMs establish a conditional link (or edge) between two proteins and thus represent molecular switches that make a protein-protein interaction conditional on a signal. No current method for functional interference with proteins in a cell allow for the Edge-specific disruption of intracellular protein networks. Indeed, nucleic-acid based methods, even if very powerful (gene KO, RNA interference, CRISPR Cas9), determine the ablation, silencing or interference of nodes (the global pool of a given protein) regardless of their post-translational modifications or status. The method of this invention allows to achieve, in a generic and streamlined way, exactly this: PTM-selective and PTM-specific protein interference studies in living cells with the isolated anti PTM intrabodies.

Introduction of PISA Selected Antibodies in Target Cells

In target validation and in therapeutic applications, the PISA selected antibodies can be used i) as genes, expressed in the target cells by well known gene transfer and gene therapy approaches (Marshall—Science 2000), or ii) as proteins, introduced into cells by one of several known cell penetrating peptides (CDP) (Cerrato et al—Expert Opin Drug Deliv 2016).

A First Generation of Chemicals that Target PTM Epitopes Directly

As discussed above, current generation chemicals employed in pathology treatment and targeting post-translational mechanisms, are directed against modifying enzymes, rather than against specific modified downstream substrate targets. Among these enzymes there are also activated kinases, which are often themselves phosphorylated in their active state. However, selection of small chemicals relies on inhibition of enzyme activity, therefore it is way more likely to isolate molecules that bind the catalytic pocket of the enzyme, rather than the post-translational modification itself. In cellular protein networks, instead, the PTM itself represents an "interaction edge", and is the binding site of other molecular partners. Being able to distinguish between "targeting a PTM-protein" (regardless of the epitope bound on it) and "targeting the protein PTM" (directly, as PISA allows) would therefore provide the deepest level of control on regulation of protein-protein interactions, permitting at the same time to have a new weapon in the field of pharmaceuticals. In addition to being used as intrabodies, PISA antibodies can be used as scaffolds to derive small chemical mimics (New Chemical Entities, NCE). Thus, PISA technology will help mimicking (and thus synthesizing) new anti-PTM chemicals by furnishing structural and chemical information about the binding site of the intrabody, which can be co-crystallized with the PTM-protein. Indeed, PISA selection and counter-selection scheme is designed to isolate antibody domains binding the modified aminoacid(s) of the protein antigen.

PISA 2.0: Expanded Genetic Code Technology Applied to PISA Screenings

The presented method allows an obvious extension and facilitation, surpassing tethered catalysis to incorporate the PTM into the antigen bait, and substituting tethered catalysis with the expanded genetic code strategies. In this case, the PTM is genetically encoded directly into the target gene. In this advanced method that inventors call "PISA 2.0" (FIGS. 23 and 24), L40 yeast strain (or another 2-hybrid system strain) is genetically modified to stably express two constructs that codify for an orthogonal pair of tRNA$_{CUA}$/aminoacil-tRNAsynthetase. This synthetase is able to couple N$_{epsilon}$-Acetyl-lysine ("acetyllisine" from now on) to the tRNA$_{CUA}$. Also, the yeast must express the LexA-Antigen target construct (without any enzyme fused at the c-term) in which the triplet nucleotides that codifies for the lysine that should be acetylated is replaced with the stop codon "TAG". LexA-target can be either incorporated by genetic modification of yeast or furnished with the pMICBD plasmids. Simultaneous expression in yeast of these proteins and tRNA results in direct incorporation of acetyllysine in the protein target in lieu of the stop signal derived from TAG (or UAG as for RNA), since Acetyllisine-tRNA$_{CUA}$ is able to recognize UAG codon during translation without interfering with synthesis of the rest of the polypeptide. This method and necessary constructs mentioned are well described in several papers (Neumann et al (2008 and 2009) and Hancock et al. (2010)). Thus, another object of the invention is a method for selecting and determining the ability of an immunoglobulin to bind to a post-translationally modified target in an intracellular environment, which folds and it is post-translationally modified as a native protein intracellularly, comprising the steps of:

a) providing a nucleic acid encoding an intracellular immunoglobulin which is associated with a first molecule; and b) providing a nucleic acid encoding an intracellular target which incorporates a post translational modification (acetylation, phosphorylation, methylation and others) that is genetically encoded via expanded genetic code methods and a second molecule, wherein said first and second molecules are separable domains of a reporter molecule; and c) expressing said first nucleotide sequence together with said second nucleotide sequence in an intracellular environment of a cell able to decode such genetically encoded post translational modification, wherein binding of said immunoglobulin with said target leads to stable interaction of the first molecule and second molecule, thus producing a detectable reporter molecule that generates a signal, and d) detecting said signal from said detectable reporter molecule, wherein said detection of a signal is indicative of stable binding activity between said immunoglobulin and said target in the intracellular environment;

e) isolating those immunoglobulins that stably bind to the target and optionally f) selecting those immunoglobulins that do not bind to target that is not post-translationally modified.

Preferably the insertion of constructs above will disrupt two metabolic genes of L40 yeast not needed for its growth, to not impair its 2-HY system functionality or disrupt no gene at all. As for the protein bait, in case of stable genetic modification in yeast, the construct can be replaced with new baits that need to be acetylated in the same generated strain, for example by including at the ends of the baits specific sites for homologous recombination or site-specific recombination.

The target PTM could also be genetically encoded, instead than by a reprogrammed stop TAG codon, by a quadruplet codon. Thus, the incorporated tRNA can also be based on a 4-base codon/anticodon strategy instead of the stop three base codon/anticodon method described above (Sisido et al., 2005).

So-modified yeast strain is then ready for IAC screening with a SPLINT libraries using state-of-the-art protocol.

In this application, L40 yeast strain has been genetically modified to incorporate the modified tRNAArg-tRNAPyl dimeric tRNA construct (from Hancock et al., plasmid SMH108 pRS426), and the modified aminoacyl-tRNA synthetase AcKRS3 (from Hancock et al., plasmid pBKka-nAcKRS3) that are able to confer to the ribosome the ability to introduce an acetyl-lysine in yeast bait protein in correspondence of the UAG mRNA triplet. Yeast L40 genome has been modified by replacing, by homologous recombination, the ADE2 gene (which is mutated and non functional in this L40 strain) with the above mentioned construct, exploiting auxotrophy of L40 for this metabolite (auxotrophy shows up at the second passage of the culture in a minimal adenine-lacking medium) and the peculiar red phenotype of the ade2 mutant cells. Indeed, the tRNA/aatRNA synthetase construct is inserted in the yeast integrating vector pRSII402, which bears a copy of a functional ADE2 gene. Insertion constructs bear distinct promoter elements (ADH1) and ADH terminators. Kozak sequence is reconstructed for Aminoacyl-tRNA Synthetase coding sequence. As initial proof of principle, the *Saccharomyces cerevisiae* Histone H3 bait has been created with acetylated lysine number nine. The complete protein sequence of the LexA-AcK9H3 PISA 2.0 bait is reported below.

```
>LexA-AcK9H3Histone (PISA 2.0) PROTEIN
                                      (SEQ ID NO: 78)
MKALTARQQEVFDLIRDHISQTGMPPTRAEIAQRLGFRSPNAAEEHLK

ALARKGVIEIVSGASRGIRLLQEEEEGLPLVGRVAAGEPLLAQQHIEG

HYQVDPSLFKPNADFLLRVSGMSMKDIGIMDGDLLAVHKTQDVRNGQV

VVARIDDEVTVKRLKKQGNKVELLPENSEFKPIVVDLRQQSFTIEGLA

VGVIRNGDWLEFPGIRRPAANYLFDDEDTPPNPKKEIEFQLTTMFMAR

TKQTAR(AcK)STGGKAPRKQLASKAARKSAPSTGGVKKPHRYKPGTV

ALREIRRFQKSTE-
```

```
>LexA-AcK9H3Histone (PISA 2.0) DNA
                                      (SEQ ID NO: 79)
ATGAAAGCGCTGACCGCGCGCCAGCAGGAAGTGTTTGATCTGATTCGC

GATCATATTAGCCAGACCGGCATGCCGCCGACCCGCGCGGAAATTGCG

CAGCGCCTGGGCTTTCGCAGCCCGAACGCGGCGGAAGAACATCTGAAA

GCGCTGGCGCGCAAAGGCGTGATTGAAATTGTGAGCGGCGCGAGCCGC

GGCATTCGCCTGCTGCAGGAAGAAGAAGAAGGCCTGCCGCTGGTGGGC

CGCGTGGCGGCGGGCGAACCGCTGCTGGCGCAGCAGCATATTGAAGGC

CATTATCAGGTGGATCCGAGCCTGTTTAAACCGAACGCGGATTTTCTG

CTGCGCGTGAGCGGCATGAGCATGAAAGATATTGGCATTATGGATGGC

GATCTGCTGGCGGTGCATAAAACCCAGGATGTGCGCAACGGCCAGGTG

GTGGTGGCGCGCATTGATGATGAAGTGACCGTGAAACGCCTGAAAAAA

CAGGGCAACAAAGTGGAACTGCTGCCGGAAAACAGCGAATTTAAACCG

ATTGTGGTGGATCTGCGCCAGCAGAGCTTTACCATTGAAGGCCTGGCG

GTGGGCGTGATTCGCAACGGCGATTGGCTGGAATTTCCGGGCATTCGC

CGCCCGGCGGCGAACTATCTGTTTGATGATGAAGATACCCCGCCGAAC

CCGAAAAAAGAAATTGAATTTCAGCTGACCACCATGTTTATGGCGCGC

ACCAAACAGACCGCGCGCGCGTGC*TAG*AGCACCGGCGGCAAAGCGCCG

CGCAAACAGCTGGCGAGCAAAGCGGCGCGCAAAAGCGCGCCGAGCACC

GGCGGCGTGAAAAAACCGCATCGCTATAAACCGGGCACCGTGGCGCTG

CGCGAAATTCGCCGCTTTCAGAAAAGCACCGAATAA
```

Bait sequence is cloned in pMICBD1 plasmid and screening is performed with both mouse or human SPLINT libraries cloned in pLinker220-VP16-AD plasmid or other VP16-AD yeast plasmids.

Results

Inventors have shown data to report proof of principle for our invention, the P.I.S.A. technology. In both cases of study (AcH3 Histone and AcIntegrase), inventors have successfully isolated intrabodies targeting the acetylated version of the target, without recognition of the non-acetylated version of the same protein. For both antibodies a proof of principle for their use for a PTM-specific protein silencing in cells has been shown above. Nowadays, it is possible to select antibodies against PTM only from in vitro methods, with previous strong manipulation of the antigen (which is limited to peptide antigens and thus not in a native conformation) and without any warranty of intracellular functionality. For instance, efforts have been made with phage display libraries constructed ad hoc (case by case) studying particular phospho-binding antibody domains (Koeber et al., 2013) or by panning in vitro against PTM-peptides (Hattori et. al., 2013), but these require knowledge of co-crystallization structures and cumbersome protein manipulation respectively. Thus, no general method to select intracellular antibodies against native-folded PTM protein existed previously, paving the way to PISA antibodies as election tools for epigenetic and target validation studies.

Moreover, the antibody ScFv-58F obtained by the present inventor has proven to be a better binder for the native form of Acetylated Histone H3 with respect to the peptide version of AcK9H3, to bind chromatin in both yeast and mammalian cells, and also to induce a very specific PTM-mediated change in gene expression in a living cellular system (yeast). No other existing intrabody has ever been proven to induce this functional effect.

REFERENCES

1) Visintin et al.—"Selection of antibodies for intracellular function using a two-hybrid in vivo system"—*PNAS* (1999);
2) Visintin et al.—"The Intracellular Antibody Capture Technology (IACT): Towards a Consensus Sequence for Intracellular Antibodies"—*JMB* (2002);
3) Visintin et al.—"The intracellular antibody capture technology: towards the high-throughput selection of functional intracellular antibodies for target validation"—*Methods* (2004);
4) Vascotto et al.—"Design and selection of an intrabody library produced de-novo for the non-structural protein NSP5 of rotavirus"—*JIM* (2005);
5) Melchionna and Cattaneo—"A protein silencing switch by ligand-induced proteasome-targeting intrabodies"—*JMB* (2007);
6) Zacchi et al.—"Gephyrin selective intrabodies as a new strategy for studying inhibitory receptor clustering"—*J Molecular Neuroscience* (2008);
7) Meli et al.—"Direct in vivo intracellular selection of conformation-sensitive antibody domains targeting Alzheimer's amyloid-beta oligomers"—*JMB* (2009);
8) Guo et al.—"A tethered catalysis: two-hybrid system to identify protein-protein interactions requiring post-translational modifications"—*Nature Biotechnology* (2004);
9) Allouch and Cereseto—"Identification of cellular factors binding to acetylated HIV-1 integrase"—*Amino acids* (2011);
10) Sato et al.—"Genetically encoded system to track histone modification in vivo"—*Nature scientific Reports* (2013);
11) Koeber et al.—"Nature-inspired design of motif-specific antibody scaffolds"—*Nature Biotechnology* (2013);
12) Hattori et al.—"Recombinant antibodies to histone post-translational modifications"—*Nature Methods* (2013);
13) Cereseto et al.—"Acetylation of HIV-1 integrase by p300 regulates viral integration."—*Embo Journal* (2005);
14) Siddiqi et al.—"Epigenetic remodeling of chromatin architecture: exploring tumor differentiation therapies in mesenchymal stem cells and sarcomas."—*Curr Stem Cell Res Ther* (2010);
15) Beltran et al.—"Reprogramming epigenetic silencing: artificial transcription factors synergize with chromatin remodeling drugs to reactivate the tumor suppressor mammary serine protease inhibitor." *Mol Cancer Ther* (2008).
16) Tanaka & Rabbitts—"Protocol for the selection of single-domain antibody fragments by third generation intracellular antibody capture"—*Nature Protocol* (2009).
17) Visintin et al.—"Intracellular antibodies for proteomics"—*JIM* (2004)
18) Neumann et al.—"Genetically encoding Nepsilon-acetyllysine in recombinant proteins"—*Nat Chem Biol*—(2008);
19) Neumann et al.—"A Method for Genetically Installing Site-Specific Acetylation in Recombinant Histones Defines the Effects of H3 K56 Acetylation"—*Molecular Cell* (2009);
20) Hancock et al.—"Expanding the genetic code of yeast for incorporation of diverse unnatural amino acids via a pyrrolysyl-tRNA synthetase/tRNA pair."—*J Am Chem Soc.* (2010)
21) Sisido et al.—"Four-base codon/anticodon strategy and non-enzymatic aminoacylation for protein engineering with non-natural amino acids."—*Methods* (2005)
22) Filippakopoulos et al.—"Selective inhibition of BET bromodomains"—*Nature* (2010)
23) Zeng et al.—"Bromodomain: An acetyl-lysine binding domain"—*FEBS Letters* (2002)
24) Falkeberg et al.—"Histone deacetylases and their inhibitors in cancer, neurological diseases and immune disorders"—*Nature Reviews Drug Discovery* (2014)
25) Di Martile et al.—"Histone acetyltransferase inhibitor CPTH6 preferentially targets lung cancer stem-like cells"—*Oncotarget* (2016)
26) Zhag et al—"Selective induction of apoptosis by histone deacetylase inhibitor SAHA in cutaneous T-cell lymphoma cells: relevance to mechanism of therapeutic action"—*The Journak of Investigative Dermatology* (2005)
27) Jenuwein et al.—"Translating the histone code"—*Science*—(2001)
28) Wongwisansri et al.—"Disruption of histone deacetylase gene RPD3 accelerates PHOS activation kinetics through inappropriate Pho84p recycling."—*Eukaryotic cell* (2005)
29) Lei et al.—"Tau protein: relevance to Parkinson's disease"—*International Journal of Biochemistry & Cell Biology*—(2010)
30) Alonso et al.—"Hyperphosphorylation induces self-assembly of tau into tangles of paired helical filaments/straight filaments"—*PNAS*—(2001)
31) Helma et al.—"Nanobodies and recombinant binders in cell biology"—*The journal of cell biology*—(2015)
32) Tanaka et al.—"Single domain intracellular antibodies: a minimal fragment for direct in vivo selection of antigen-specific intrabodies"—*Journal of molecular biology*—(2003)
33) Marks and Bradbury—"PCR cloning of human immunoglobulin genes"—*Methods in Molecular Biology*—(2004)
34) Lang and Chin—"Cellular incorporation of unnatural amino acids and bioorthogonal labeling of proteins"—*Chemical reviews*—(2014)
35) Marshall—"Gene Therapy on trial"—*Science*—(2000)
36) Cerrato et al—"Cell-penetrating peptides with intracellular organelle targeting"—*Expert Opin Drug Deliv*—(2016)

The invention claimed is:

1. A method for selecting an immunoglobulin able to bind in an intracellular environment to a post-translationally modified target or for determining the ability of an immunoglobulin to bind in an intracellular environment to a post-translationally modified target, wherein the post-translational modification is acetylation or phosphorylation: said method comprising the steps of:
    a) providing a first nucleotide sequence encoding an intracellular immunoglobulin which is associated with a first molecule; and
    b) providing a second nucleotide sequence encoding a second molecule and an intracellular target which:
        is associated with an enzyme that modifies the target in vivo, or
        is subjected to a direct site-specific genetic encoding of the Post-Translational Modifications (PTM) into the target protein,
    wherein the enzyme is an acetyl transferase or a tau kinase, and
    wherein said first and second molecules are separable domains of a reporter molecule; and c) expressing said first nucleotide sequence together with said second nucleotide sequence in an intracellular environment, wherein binding of said immunoglobulin with said target leads to stable interaction of the first molecule and second molecule, thus producing a detectable reporter molecule that generates a signal, and d) detecting said signal from said detectable reporter molecule, wherein said detection of a signal is indicative of stable binding activity between said immunoglobulin and said target in the intracellular environment;

e) isolating those immunoglobulins that stably bind to the target and optionally f) selecting those immunoglobulins that do not bind to target that is not post-translationally modified;

wherein the first molecule is the activation domain of VP16 and the second molecule is the DNA-binding domain of LexA and wherein the immunoglobulin is selected from the group consisting of: an intact immunoglobulin, a Fv, a scFv (single chain Fv fragment), a Fab, a F(ab')2, an "antibody-like" domain, an "antibody-mimetic" domain, and a single antibody domain (VH domain or VL domains).

2. The method according to claim 1, wherein the first nucleotide sequence encoding the immunoglobulin is obtained from a library encoding a repertoire of immunoglobulin-encoding nucleic acids and/or no prior application of phage display is used to isolate immunoglobulins which bind to a target.

3. The method according to claim 1, wherein the post-translation modified target is acetylated histone H3 or acetylated HIV-integrase or phosphorylated Tau.

4. The method according to claim 1, wherein the detecting step is selected from the group consisting of: a change in an optical property and the activation of a reporter gene, and allows the sorting of cells.

5. The method according to claim 2, wherein the library is:
a) a naïve Single Pot Library of INTracellular antibodies (SPLINT) human or mouse ScFv library, or a naïve SPLINT human VH library or a phage library encoding a repertoire of immunoglobulins and/or
b) is constructed from nucleic acids isolated from an organism which has been challenged with an antigen.

6. A method for selecting an scFv immunoglobulin that binds acetylated histone in an intracellular environment, wherein the method comprises:
a) providing a first nucleotide sequence encoding a fusion protein comprising an scFv or a VH fused to a VP16 activation domain;
b) providing a second nucleotide sequence as bait encoding a fusion protein comprising a LexA binding domain, an antigen of interest, Gcn5 (histone Acetyl transferase) and HA epitope;
c) expressing the first nucleotide sequence and the second nucleotide sequence in a cytoplasm of a yeast cell;
wherein binding of the VH or scFv with the acetylated histone leads to stable interaction of the report molecule that generate a signal; and
d) detecting the signal from the reporter molecule is indicative of stable binding activity between the VH or scFv and the acetylated histone in the intracellular environment; and
e) isolating those immunoglobulins that stably bind to the acetylated histone.

7. The method according to claim 6, wherein the acetylated histone is acetylated histone 3 (H3).

8. The method according to claim 1, wherein the first nucleotide sequence is in a library comprising a repertoire of nucleic acid sequences encoding VH or scFv fused to VP16 activation domain, wherein the second nucleotide sequence is a nucleic acid sequence encoding a fusion protein comprising the amino acid sequence of SEQ ID NO: 17 or SEQ ID NO: 13, and wherein the library is a naive SPLINT human or mouse scFv library or a naive SPLINT human VH library.

9. The method according to claim 1, wherein the enzyme is a histone acetyl transferase.

* * * * *

SEQUENCE LISTING

<160> NUMBER OF SEQ ID NOS: 99

<210> SEQ ID NO 1
<211> LENGTH: 117
<212> TYPE: PRT

<213> ORGANISM: Artificial Sequence
<220> FEATURE:
<223> OTHER INFORMATION: VH-12A

<400> SEQUENCE: 1

```
Gln Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Ser Leu Leu Trp Trp Gly Gly Thr Leu Val Thr Val Ser Ala
            100                 105                 110

Ala Ser Val Ser Ser
        115
```

<210> SEQ ID NO 2
<211> LENGTH: 119
<212> TYPE: PRT
<213> ORGANISM: Artificial Sequence
<220> FEATURE:
<223> OTHER INFORMATION: VH-112A

<400> SEQUENCE: 2

```
Gln Val His Val Lys Gln Ser Gly Ala Glu Leu Val Arg Pro Gly Ala
1               5                   10                  15

Ser Val Lys Ile Ser Cys Lys Ala Phe Gly Tyr Thr Phe Thr Asn His
            20                  25                  30

His Ile Asn Trp Val Lys Gln Arg Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Tyr Tyr Gly Ser Ser Tyr Ala Met Asp Tyr Trp Gly Gln Gly
            100                 105                 110

Thr Ser Val Thr Val Ser Ser
        115
```

<210> SEQ ID NO 3
<211> LENGTH: 251
<212> TYPE: PRT
<213> ORGANISM: Artificial Sequence
<220> FEATURE:
<223> OTHER INFORMATION: ScFv-58F

<400> SEQUENCE: 3

```
Asp Ile Leu Met Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
            20                  25                  30
```

```
Tyr Leu His Trp Tyr Gln Gln Lys Ser Gly Ala Ser Pro Lys Leu Trp
        35                  40                  45
Ile Tyr Ser Thr Ser Asn Leu Ala Ser Gly Val Pro Ala Arg Phe Ser
50                  55                  60
Gly Ser Gly Ser Gly Thr Ser Tyr Ser Leu Thr Ile Ser Ser Val Glu
65                  70                  75                  80
Ala Glu Asp Ala Ala Thr Tyr Tyr Cys Gln Gln Tyr Ser Gly Tyr Pro
                85                  90                  95
Trp Thr Ser Gly Gly Gly Thr Lys Leu Glu Ile Lys Arg Ser Gly Gly
            100                 105                 110
Ser Thr Ser Gly Ser Gly Lys Pro Gly Ser Gly Glu Gly Ser Ser Ser
        115                 120                 125
Thr Glu Val Lys Val Glu Glu Ser Gly Gly Gly Leu Val Gln Pro Gly
    130                 135                 140
Gly Ser Met Lys Leu Ser Cys Val Ala Ser Gly Phe Thr Phe Ser Asn
145                 150                 155                 160
Tyr Trp Met Asn Trp Val Arg Gln Ser Pro Glu Lys Gly Leu Glu Trp
                165                 170                 175
Val Ala Glu Ile Arg Leu Lys Ser Asn Asn Tyr Ala Thr His Tyr Ala
            180                 185                 190
Glu Ser Val Lys Gly Arg Phe Thr Ile Ser Arg Asp Asp Ser Glu Ser
        195                 200                 205
Ser Val Tyr Leu Gln Met Asn Asn Leu Arg Ala Glu Asp Thr Gly Ile
    210                 215                 220
Tyr Tyr Cys Thr Arg Arg Asn Gly Pro Ser Ser Arg Ala Met Asp Tyr
225                 230                 235                 240
Trp Gly Gln Gly Thr Thr Val Thr Val Ser Ser
                245                 250

<210> SEQ ID NO 4
<211> LENGTH: 21
<212> TYPE: PRT
<213> ORGANISM: Artificial Sequence
<220> FEATURE:
<223> OTHER INFORMATION: antigen H3#1

<400> SEQUENCE: 4

Ala Arg Thr Lys Gln Thr Ala Arg Lys Ser Thr Gly Gly Lys Ala Pro
1               5                   10                  15
Arg Lys Gln Leu Ala
            20

<210> SEQ ID NO 5
<211> LENGTH: 21
<212> TYPE: PRT
<213> ORGANISM: Artificial Sequence
<220> FEATURE:
<223> OTHER INFORMATION: antigen H3#2
<220> FEATURE:
<221> NAME/KEY: MOD_RES
<222> LOCATION: (9)..(9)
<223> OTHER INFORMATION: ACETYLATION
<220> FEATURE:
<221> NAME/KEY: MOD_RES
<222> LOCATION: (14)..(14)
<223> OTHER INFORMATION: ACETYLATION

<400> SEQUENCE: 5

Ala Arg Thr Lys Gln Thr Ala Arg Lys Ser Thr Gly Gly Lys Ala Pro
1               5                   10                  15
```

Arg Lys Gln Leu Ala
            20

<210> SEQ ID NO 6
<211> LENGTH: 21
<212> TYPE: PRT
<213> ORGANISM: Artificial Sequence
<220> FEATURE:
<223> OTHER INFORMATION: antigen H3#3
<220> FEATURE:
<221> NAME/KEY: MOD_RES
<222> LOCATION: (9)..(9)
<223> OTHER INFORMATION: ACETYLATION

<400> SEQUENCE: 6

Ala Arg Thr Lys Gln Thr Ala Arg Lys Ser Thr Gly Gly Lys Ala Pro
1               5                   10                  15

Arg Lys Gln Leu Ala
            20

<210> SEQ ID NO 7
<211> LENGTH: 21
<212> TYPE: PRT
<213> ORGANISM: Artificial Sequence
<220> FEATURE:
<223> OTHER INFORMATION: antigen H3#4
<220> FEATURE:
<221> NAME/KEY: MOD_RES
<222> LOCATION: (14)..(14)
<223> OTHER INFORMATION: ACETYLATION

<400> SEQUENCE: 7

Ala Arg Thr Lys Gln Thr Ala Arg Lys Ser Thr Gly Gly Lys Ala Pro
1               5                   10                  15

Arg Lys Gln Leu Ala
            20

<210> SEQ ID NO 8
<211> LENGTH: 21
<212> TYPE: PRT
<213> ORGANISM: Artificial Sequence
<220> FEATURE:
<223> OTHER INFORMATION: antigen H3#5
<220> FEATURE:
<221> NAME/KEY: MOD_RES
<222> LOCATION: (18)..(18)
<223> OTHER INFORMATION: ACETYLATION

<400> SEQUENCE: 8

Ala Arg Thr Lys Gln Thr Ala Arg Lys Ser Thr Gly Gly Lys Ala Pro
1               5                   10                  15

Arg Lys Gln Leu Ala
            20

<210> SEQ ID NO 9
<211> LENGTH: 20
<212> TYPE: PRT
<213> ORGANISM: Artificial Sequence
<220> FEATURE:
<223> OTHER INFORMATION: antigen H3#6

<400> SEQUENCE: 9

Ser Thr Gly Gly Lys Ala Pro Arg Lys Gln Leu Ala Ser Lys Ala Ala
1               5                   10                  15

Arg Lys Ser Ala
            20

```
<210> SEQ ID NO 10
<211> LENGTH: 20
<212> TYPE: PRT
<213> ORGANISM: Artificial Sequence
<220> FEATURE:
<223> OTHER INFORMATION: antigen H3#7
<220> FEATURE:
<221> NAME/KEY: MOD_RES
<222> LOCATION: (14)..(14)
<223> OTHER INFORMATION: ACETYLATION

<400> SEQUENCE: 10

Ser Thr Gly Gly Lys Ala Pro Arg Lys Gln Leu Ala Ser Lys Ala Ala
1               5                   10                  15

Arg Lys Ser Ala
            20

<210> SEQ ID NO 11
<211> LENGTH: 20
<212> TYPE: PRT
<213> ORGANISM: Artificial Sequence
<220> FEATURE:
<223> OTHER INFORMATION: antigen H3#8
<220> FEATURE:
<221> NAME/KEY: MOD_RES
<222> LOCATION: (18)..(18)
<223> OTHER INFORMATION: ACETYLATION

<400> SEQUENCE: 11

Ser Thr Gly Gly Lys Ala Pro Arg Lys Gln Leu Ala Ser Lys Ala Ala
1               5                   10                  15

Arg Lys Ser Ala
            20

<210> SEQ ID NO 12
<211> LENGTH: 1042
<212> TYPE: PRT
<213> ORGANISM: Artificial Sequence
<220> FEATURE:
<223> OTHER INFORMATION: LexA-Integrase-p300wt-HA

<400> SEQUENCE: 12

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
```

```
            145                 150                 155                 160
Gln Gly Asn Lys Val Glu Leu Leu Pro Glu Asn Ser Glu Phe Lys Pro
                    165                 170                 175
Ile Val Val Asp Leu Arg Gln Gln Ser Phe Thr Ile Glu Gly Leu Ala
                    180                 185                 190
Val Gly Val Ile Arg Asn Gly Asp Trp Leu Glu Phe Leu Asp Gly Ile
                    195                 200                 205
Asp Lys Ala Gln Glu Glu His Glu Lys Tyr His Ser Asn Trp Arg Ala
                    210                 215                 220
Met Ala Ser Asp Phe Asn Leu Pro Pro Val Val Ala Lys Glu Ile Val
225                 230                 235                 240
Ala Ser Cys Asp Lys Cys Gln Leu Lys Gly Glu Ala Met His Gly Gln
                    245                 250                 255
Val Asp Cys Ser Pro Gly Ile Trp Gln Leu Asp Cys Thr His Leu Glu
                    260                 265                 270
Gly Lys Val Ile Leu Val Ala Val His Val Ala Ser Gly Tyr Ile Glu
                    275                 280                 285
Ala Glu Val Ile Pro Ala Glu Thr Gly Gln Glu Thr Ala Tyr Phe Leu
                    290                 295                 300
Leu Lys Leu Ala Gly Arg Trp Pro Val Lys Thr Val His Thr Asp Asn
305                 310                 315                 320
Gly Ser Asn Phe Thr Ser Thr Thr Val Lys Ala Ala Cys Trp Trp Ala
                    325                 330                 335
Gly Ile Lys Gln Glu Phe Gly Ile Pro Tyr Asn Pro Gln Ser Gln Gly
                    340                 345                 350
Val Ile Glu Ser Met Asn Lys Glu Leu Lys Lys Ile Ile Gly Gln Val
                    355                 360                 365
Arg Asp Gln Ala Glu His Leu Lys Thr Ala Val Gln Met Ala Val Phe
                    370                 375                 380
Ile His Asn Phe Lys Arg Lys Gly Gly Ile Gly Gly Tyr Ser Ala Gly
385                 390                 395                 400
Glu Arg Ile Val Asp Ile Ile Ala Thr Asp Ile Gln Thr Lys Glu Leu
                    405                 410                 415
Gln Lys Gln Ile Thr Lys Ile Gln Asn Phe Arg Val Tyr Tyr Arg Asp
                    420                 425                 430
Ser Arg Asp Pro Val Trp Lys Gly Pro Ala Lys Leu Leu Trp Lys Gly
                    435                 440                 445
Glu Gly Ala Val Val Ile Gln Asp Asn Ser Asp Ile Lys Val Val Pro
                    450                 455                 460
Arg Arg Lys Ala Lys Ile Ile Arg Asp Tyr Gly Lys Gln Met Ala Gly
465                 470                 475                 480
Asp Asp Cys Val Ala Ser Arg Gln Asp Glu Asp Arg Arg Thr Ser
                    485                 490                 495
Arg Val Tyr Lys Tyr Cys Ser Lys Leu Ser Glu Val Phe Glu Gln Glu
                    500                 505                 510
Ile Asp Pro Val Met Gln Ser Leu Gly Tyr Cys Cys Gly Arg Lys Leu
                    515                 520                 525
Glu Phe Ser Pro Gln Thr Leu Cys Cys Tyr Gly Lys Gln Leu Cys Thr
                    530                 535                 540
Ile Pro Arg Asp Ala Thr Tyr Tyr Ser Tyr Gln Asn Arg Tyr His Phe
545                 550                 555                 560
Cys Glu Lys Cys Phe Asn Glu Ile Gln Gly Glu Ser Val Ser Leu Gly
                    565                 570                 575
```

```
Asp Asp Pro Ser Gln Pro Gln Thr Thr Ile Asn Lys Glu Gln Phe Ser
            580                 585                 590

Lys Arg Lys Asn Asp Thr Leu Asp Pro Glu Leu Phe Val Glu Cys Thr
        595                 600                 605

Glu Cys Gly Arg Lys Met His Gln Ile Cys Val Leu His His Glu Ile
610                 615                 620

Ile Trp Pro Ala Gly Phe Val Cys Asp Gly Cys Leu Lys Lys Ser Ala
625                 630                 635                 640

Arg Thr Arg Lys Glu Asn Lys Phe Ser Ala Lys Arg Leu Pro Ser Thr
                645                 650                 655

Arg Leu Gly Thr Phe Leu Glu Asn Arg Val Asn Asp Phe Leu Arg Arg
            660                 665                 670

Gln Asn His Pro Glu Ser Gly Glu Val Thr Val Arg Val His Ala
        675                 680                 685

Ser Asp Lys Thr Val Glu Val Lys Pro Gly Met Lys Ala Arg Phe Val
    690                 695                 700

Asp Ser Gly Glu Met Ala Glu Ser Phe Pro Tyr Arg Thr Lys Ala Leu
705                 710                 715                 720

Phe Ala Phe Glu Glu Ile Asp Gly Val Asp Leu Cys Phe Phe Gly Met
                725                 730                 735

His Val Gln Glu Tyr Gly Ser Asp Cys Pro Pro Asn Gln Arg Arg
            740                 745                 750

Val Tyr Ile Ser Tyr Leu Asp Ser Val His Phe Phe Arg Pro Lys Cys
        755                 760                 765

Leu Arg Thr Ala Val Tyr His Glu Ile Leu Ile Gly Tyr Leu Glu Tyr
770                 775                 780

Val Lys Lys Leu Gly Tyr Thr Thr Gly His Ile Trp Ala Cys Pro Pro
785                 790                 795                 800

Ser Glu Gly Asp Asp Tyr Ile Phe His Cys His Pro Pro Asp Gln Lys
                805                 810                 815

Ile Pro Lys Pro Lys Arg Leu Gln Glu Trp Tyr Lys Lys Met Leu Asp
            820                 825                 830

Lys Ala Val Ser Glu Arg Ile Val His Asp Tyr Lys Asp Ile Phe Lys
        835                 840                 845

Gln Ala Thr Glu Asp Arg Leu Thr Ser Ala Lys Glu Leu Pro Tyr Phe
850                 855                 860

Glu Gly Asp Phe Trp Pro Asn Val Leu Glu Glu Ser Ile Lys Glu Leu
865                 870                 875                 880

Glu Gln Glu Glu Glu Glu Arg Lys Arg Glu Asn Thr Ser Asn Glu
                885                 890                 895

Ser Thr Asp Val Thr Lys Gly Asp Ser Lys Asn Ala Lys Lys Lys Asn
            900                 905                 910

Asn Lys Lys Thr Ser Lys Asn Lys Ser Ser Leu Ser Arg Gly Asn Lys
        915                 920                 925

Lys Lys Pro Gly Met Pro Asn Val Ser Asn Asp Leu Ser Gln Lys Leu
    930                 935                 940

Tyr Ala Thr Met Glu Lys His Lys Glu Val Phe Phe Val Ile Arg Leu
945                 950                 955                 960

Ile Ala Gly Pro Ala Ala Asn Ser Leu Pro Pro Ile Val Asp Pro Asp
                965                 970                 975

Pro Leu Ile Pro Cys Asp Leu Met Asp Gly Arg Asp Ala Phe Leu Thr
            980                 985                 990
```

Leu Ala Arg Asp Lys His Leu Glu Phe Ser Ser Leu Arg Arg Ala Gln
            995                1000                1005

Trp Ser Thr Met Cys Met Leu Val Glu Leu His Thr Gln Ser Gln
    1010                1015                1020

Asp Arg Phe Val Tyr Thr Cys Asn Glu Cys Tyr Pro Tyr Asp Val
    1025                1030                1035

Pro Asp Tyr Ala
    1040

<210> SEQ ID NO 13
<211> LENGTH: 1042
<212> TYPE: PRT
<213> ORGANISM: Artificial Sequence
<220> FEATURE:
<223> OTHER INFORMATION: LexA-Integrase-p300mut-HA

<400> SEQUENCE: 13

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
                20                  25                  30

Gln Arg Leu Gly Phe Arg Ser Pro Asn Ala Ala Glu Glu His Leu Lys
            35                  40                  45

Ala Leu Ala Arg Lys Gly Val Ile Glu Ile Val Ser Gly Ala Ser Arg
        50                  55                  60

Gly Ile Arg Leu Leu Gln Glu Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu Glu Phe Leu Asp Gly Ile
        195                 200                 205

Asp Lys Ala Gln Glu Glu His Glu Lys Tyr His Ser Asn Trp Arg Ala
210                 215                 220

Met Ala Ser Asp Phe Asn Leu Pro Pro Val Val Ala Lys Glu Ile Val
225                 230                 235                 240

Ala Ser Cys Asp Lys Cys Gln Leu Lys Gly Glu Ala Met His Gly Gln
                245                 250                 255

Val Asp Cys Ser Pro Gly Ile Trp Gln Leu Asp Cys Thr His Leu Glu
            260                 265                 270

Gly Lys Val Ile Leu Val Ala Val His Val Ala Ser Gly Tyr Ile Glu
        275                 280                 285

Ala Glu Val Ile Pro Ala Glu Thr Gly Gln Glu Thr Ala Tyr Phe Leu
290                 295                 300

```
Leu Lys Leu Ala Gly Arg Trp Pro Val Lys Thr Val His Thr Asp Asn
305                 310                 315                 320

Gly Ser Asn Phe Thr Ser Thr Thr Val Lys Ala Ala Cys Trp Trp Ala
            325                 330                 335

Gly Ile Lys Gln Glu Phe Gly Ile Pro Tyr Asn Pro Gln Ser Gln Gly
        340                 345                 350

Val Ile Glu Ser Met Asn Lys Glu Leu Lys Lys Ile Ile Gly Gln Val
    355                 360                 365

Arg Asp Gln Ala Glu His Leu Lys Thr Ala Val Gln Met Ala Val Phe
370                 375                 380

Ile His Asn Phe Lys Arg Lys Gly Gly Ile Gly Gly Tyr Ser Ala Gly
385                 390                 395                 400

Glu Arg Ile Val Asp Ile Ile Ala Thr Asp Ile Gln Thr Lys Glu Leu
            405                 410                 415

Gln Lys Gln Ile Thr Lys Ile Gln Asn Phe Arg Val Tyr Tyr Arg Asp
        420                 425                 430

Ser Arg Asp Pro Val Trp Lys Gly Pro Ala Lys Leu Leu Trp Lys Gly
    435                 440                 445

Glu Gly Ala Val Val Ile Gln Asp Asn Ser Asp Ile Lys Val Val Pro
450                 455                 460

Arg Arg Lys Ala Lys Ile Ile Arg Asp Tyr Gly Lys Gln Met Ala Gly
465                 470                 475                 480

Asp Asp Cys Val Ala Ser Arg Gln Asp Glu Asp Arg Arg Thr Ser
            485                 490                 495

Arg Val Tyr Lys Tyr Cys Ser Lys Leu Ser Glu Val Phe Glu Gln Glu
        500                 505                 510

Ile Asp Pro Val Met Gln Ser Leu Gly Tyr Cys Cys Gly Arg Lys Leu
    515                 520                 525

Glu Phe Ser Pro Gln Thr Leu Cys Cys Tyr Gly Lys Gln Leu Cys Thr
530                 535                 540

Ile Pro Arg Asp Ala Thr Tyr Tyr Ser Tyr Gln Asn Arg Tyr His Phe
545                 550                 555                 560

Cys Glu Lys Cys Phe Asn Glu Ile Gln Gly Glu Ser Val Ser Leu Gly
            565                 570                 575

Asp Asp Pro Ser Gln Pro Gln Thr Thr Ile Asn Lys Glu Gln Phe Ser
        580                 585                 590

Lys Arg Lys Asn Asp Thr Leu Asp Pro Glu Leu Phe Val Glu Cys Thr
    595                 600                 605

Glu Cys Gly Arg Lys Met His Gln Ile Cys Val Leu His His Glu Ile
610                 615                 620

Ile Trp Pro Ala Gly Phe Val Cys Asp Gly Cys Leu Lys Lys Ser Ala
625                 630                 635                 640

Arg Thr Arg Lys Glu Asn Lys Phe Ser Ala Lys Arg Leu Pro Ser Thr
            645                 650                 655

Arg Leu Gly Thr Phe Leu Glu Asn Arg Val Asn Asp Phe Leu Arg Arg
        660                 665                 670

Gln Asn His Pro Glu Ser Gly Glu Val Thr Val Arg Val Val His Ala
    675                 680                 685

Ser Asp Lys Thr Val Glu Val Lys Pro Gly Met Lys Ala Arg Phe Val
690                 695                 700

Asp Ser Gly Glu Met Ala Glu Ser Phe Pro Tyr Arg Thr Lys Ala Leu
705                 710                 715                 720

Phe Ala Phe Glu Glu Ile Asp Gly Val Asp Leu Cys Phe Phe Gly Met
```

His Val Gln Glu Tyr Gly Ser Asp Cys Pro Pro Asn Gln Arg Arg
              725                 730                 735
                740                 745                 750

Val Tyr Ile Ser Tyr Leu Tyr Ser Val His Phe Phe Arg Pro Lys Cys
                755                 760                 765

Leu Arg Thr Ala Val Tyr His Glu Ile Leu Ile Gly Tyr Leu Glu Tyr
                770                 775                 780

Val Lys Lys Leu Gly Tyr Thr Thr Gly His Ile Trp Ala Cys Pro Pro
785                 790                 795                 800

Ser Glu Gly Asp Asp Tyr Ile Phe His Cys His Pro Pro Asp Gln Lys
                805                 810                 815

Ile Pro Lys Pro Lys Arg Leu Gln Glu Trp Tyr Lys Lys Met Leu Asp
                820                 825                 830

Lys Ala Val Ser Glu Arg Ile Val His Asp Tyr Lys Asp Ile Phe Lys
                835                 840                 845

Gln Ala Thr Glu Asp Arg Leu Thr Ser Ala Lys Glu Leu Pro Tyr Phe
                850                 855                 860

Glu Gly Asp Phe Trp Pro Asn Val Leu Glu Glu Ser Ile Lys Glu Leu
865                 870                 875                 880

Glu Gln Glu Glu Glu Glu Arg Lys Arg Glu Glu Asn Thr Ser Asn Glu
                885                 890                 895

Ser Thr Asp Val Thr Lys Gly Asp Ser Lys Asn Ala Lys Lys Lys Asn
                900                 905                 910

Asn Lys Lys Thr Ser Lys Asn Lys Ser Ser Leu Ser Arg Gly Asn Lys
                915                 920                 925

Lys Lys Pro Gly Met Pro Asn Val Ser Asn Asp Leu Ser Gln Lys Leu
                930                 935                 940

Tyr Ala Thr Met Glu Lys His Lys Glu Val Phe Phe Val Ile Arg Leu
945                 950                 955                 960

Ile Ala Gly Pro Ala Ala Asn Ser Leu Pro Pro Ile Val Asp Pro Asp
                965                 970                 975

Pro Leu Ile Pro Cys Asp Leu Met Asp Gly Arg Asp Ala Phe Leu Thr
                980                 985                 990

Leu Ala Arg Asp Lys His Leu Glu Phe Ser Ser Leu Arg Arg Ala Gln
                995                1000                1005

Trp Ser Thr Met Cys Met Leu Val Glu Leu His Thr Gln Ser Gln
                1010                1015                1020

Asp Arg Phe Val Tyr Thr Cys Asn Glu Cys Tyr Pro Tyr Asp Val
                1025                1030                1035

Pro Asp Tyr Ala
                1040

<210> SEQ ID NO 14
<211> LENGTH: 752
<212> TYPE: PRT
<213> ORGANISM: Artificial Sequence
<220> FEATURE:
<223> OTHER INFORMATION: LexA-p300wt-HA

<400> SEQUENCE: 14

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
                20                  25                  30

Gln Arg Leu Gly Phe Arg Ser Pro Asn Ala Ala Glu Glu His Leu Lys

```
                35                  40                  45
Ala Leu Ala Arg Lys Gly Val Ile Glu Ile Val Ser Gly Ala Ser Arg
 50                  55                  60

Gly Ile Arg Leu Leu Gln Glu Glu Glu Gly Leu Pro Leu Val Gly
 65                  70                  75                  80

Arg Val Ala Ala Gly Glu Pro Leu Leu Ala Gln Gln His Ile Glu Gly
                 85                  90                  95

His Tyr Gln Val Asp Pro Ser Leu Phe Lys Pro Asn Ala Asp Phe Leu
                100                 105                 110

Leu Arg Val Ser Gly Met Ser Met Lys Asp Ile Gly Ile Met Asp Gly
                115                 120                 125

Asp Leu Leu Ala Val His Lys Thr Gln Asp Val Arg Asn Gly Gln Val
                130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
                180                 185                 190

Val Gly Val Ile Arg Asn Gly Asp Trp Leu Glu Phe Thr Ser Arg Val
                195                 200                 205

Tyr Lys Tyr Cys Ser Lys Leu Ser Glu Val Phe Glu Gln Glu Ile Asp
                210                 215                 220

Pro Val Met Gln Ser Leu Gly Tyr Cys Cys Gly Arg Lys Leu Glu Phe
225                 230                 235                 240

Ser Pro Gln Thr Leu Cys Cys Tyr Gly Lys Gln Leu Cys Thr Ile Pro
                245                 250                 255

Arg Asp Ala Thr Tyr Tyr Ser Tyr Gln Asn Arg Tyr His Phe Cys Glu
                260                 265                 270

Lys Cys Phe Asn Glu Ile Gln Gly Glu Ser Val Ser Leu Gly Asp Asp
                275                 280                 285

Pro Ser Gln Pro Gln Thr Thr Ile Asn Lys Glu Gln Phe Ser Lys Arg
                290                 295                 300

Lys Asn Asp Thr Leu Asp Pro Glu Leu Phe Val Glu Cys Thr Glu Cys
305                 310                 315                 320

Gly Arg Lys Met His Gln Ile Cys Val Leu His His Glu Ile Ile Trp
                325                 330                 335

Pro Ala Gly Phe Val Cys Asp Gly Cys Leu Lys Lys Ser Ala Arg Thr
                340                 345                 350

Arg Lys Glu Asn Lys Phe Ser Ala Lys Arg Leu Pro Ser Thr Arg Leu
                355                 360                 365

Gly Thr Phe Leu Glu Asn Arg Val Asn Asp Phe Leu Arg Arg Gln Asn
                370                 375                 380

His Pro Glu Ser Gly Glu Val Thr Val Arg Val His Ala Ser Asp
385                 390                 395                 400

Lys Thr Val Glu Val Lys Pro Gly Met Lys Ala Arg Phe Val Asp Ser
                405                 410                 415

Gly Glu Met Ala Glu Ser Phe Pro Tyr Arg Thr Lys Ala Leu Phe Ala
                420                 425                 430

Phe Glu Glu Ile Asp Gly Val Asp Leu Cys Phe Phe Gly Met His Val
                435                 440                 445

Gln Glu Tyr Gly Ser Asp Cys Pro Pro Asn Gln Arg Arg Val Tyr
                450                 455                 460
```

```
Ile Ser Tyr Leu Asp Ser Val His Phe Phe Arg Pro Lys Cys Leu Arg
465                 470                 475                 480

Thr Ala Val Tyr His Glu Ile Leu Ile Gly Tyr Leu Glu Tyr Val Lys
                485                 490                 495

Lys Leu Gly Tyr Thr Thr Gly His Ile Trp Ala Cys Pro Pro Ser Glu
            500                 505                 510

Gly Asp Asp Tyr Ile Phe His Cys His Pro Asp Gln Lys Ile Pro
            515                 520                 525

Lys Pro Lys Arg Leu Gln Glu Trp Tyr Lys Lys Met Leu Asp Lys Ala
530                 535                 540

Val Ser Glu Arg Ile Val His Asp Tyr Lys Asp Ile Phe Lys Gln Ala
545                 550                 555                 560

Thr Glu Asp Arg Leu Thr Ser Ala Lys Glu Leu Pro Tyr Phe Glu Gly
                565                 570                 575

Asp Phe Trp Pro Asn Val Leu Glu Glu Ser Ile Lys Glu Leu Glu Gln
            580                 585                 590

Glu Glu Glu Glu Arg Lys Arg Glu Glu Asn Thr Ser Asn Glu Ser Thr
                595                 600                 605

Asp Val Thr Lys Gly Asp Ser Lys Asn Ala Lys Lys Lys Asn Asn Lys
            610                 615                 620

Lys Thr Ser Lys Asn Lys Ser Ser Leu Ser Arg Gly Asn Lys Lys Lys
625                 630                 635                 640

Pro Gly Met Pro Asn Val Ser Asn Asp Leu Ser Gln Lys Leu Tyr Ala
                645                 650                 655

Thr Met Glu Lys His Lys Glu Val Phe Phe Val Ile Arg Leu Ile Ala
                660                 665                 670

Gly Pro Ala Ala Asn Ser Leu Pro Pro Ile Val Asp Pro Asp Pro Leu
            675                 680                 685

Ile Pro Cys Asp Leu Met Asp Gly Arg Asp Ala Phe Leu Thr Leu Ala
            690                 695                 700

Arg Asp Lys His Leu Glu Phe Ser Ser Leu Arg Arg Ala Gln Trp Ser
705                 710                 715                 720

Thr Met Cys Met Leu Val Glu Leu His Thr Gln Ser Gln Asp Arg Phe
                725                 730                 735

Val Tyr Thr Cys Asn Glu Cys Tyr Pro Tyr Asp Val Pro Asp Tyr Ala
            740                 745                 750

<210> SEQ ID NO 15
<211> LENGTH: 752
<212> TYPE: PRT
<213> ORGANISM: Artificial Sequence
<220> FEATURE:
<223> OTHER INFORMATION: LexA-p300mut-HA

<400> SEQUENCE: 15

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
                20                  25                  30

Gln Arg Leu Gly Phe Arg Ser Pro Asn Ala Ala Glu Glu His Leu Lys
            35                  40                  45

Ala Leu Ala Arg Lys Gly Val Ile Glu Ile Val Ser Gly Ala Ser Arg
        50                  55                  60

Gly Ile Arg Leu Leu Gln Glu Glu Glu Glu Gly Leu Pro Leu Val Gly
65                  70                  75                  80
```

```
Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu Glu Phe Thr Ser Arg Val
        195                 200                 205

Tyr Lys Tyr Cys Ser Lys Leu Ser Glu Val Phe Glu Gln Glu Ile Asp
    210                 215                 220

Pro Val Met Gln Ser Leu Gly Tyr Cys Cys Gly Arg Lys Leu Glu Phe
225                 230                 235                 240

Ser Pro Gln Thr Leu Cys Cys Tyr Gly Lys Gln Leu Cys Thr Ile Pro
                245                 250                 255

Arg Asp Ala Thr Tyr Tyr Ser Tyr Gln Asn Arg Tyr His Phe Cys Glu
            260                 265                 270

Lys Cys Phe Asn Glu Ile Gln Gly Glu Ser Val Ser Leu Gly Asp Asp
        275                 280                 285

Pro Ser Gln Pro Gln Thr Thr Ile Asn Lys Glu Gln Phe Ser Lys Arg
    290                 295                 300

Lys Asn Asp Thr Leu Asp Pro Glu Leu Phe Val Glu Cys Thr Glu Cys
305                 310                 315                 320

Gly Arg Lys Met His Gln Ile Cys Val Leu His His Glu Ile Ile Trp
                325                 330                 335

Pro Ala Gly Phe Val Cys Asp Gly Cys Leu Lys Lys Ser Ala Arg Thr
            340                 345                 350

Arg Lys Glu Asn Lys Phe Ser Ala Lys Arg Leu Pro Ser Thr Arg Leu
        355                 360                 365

Gly Thr Phe Leu Glu Asn Arg Val Asn Asp Phe Leu Arg Arg Gln Asn
    370                 375                 380

His Pro Glu Ser Gly Glu Val Thr Val Arg Val Val His Ala Ser Asp
385                 390                 395                 400

Lys Thr Val Glu Val Lys Pro Gly Met Lys Ala Arg Phe Val Asp Ser
                405                 410                 415

Gly Glu Met Ala Glu Ser Phe Pro Tyr Arg Thr Lys Ala Leu Phe Ala
            420                 425                 430

Phe Glu Glu Ile Asp Gly Val Asp Leu Cys Phe Phe Gly Met His Val
        435                 440                 445

Gln Glu Tyr Gly Ser Asp Cys Pro Pro Asn Gln Arg Arg Val Tyr
    450                 455                 460

Ile Ser Tyr Leu Tyr Ser Val His Phe Phe Arg Pro Lys Cys Leu Arg
465                 470                 475                 480

Thr Ala Val Tyr His Glu Ile Leu Ile Gly Tyr Leu Glu Tyr Val Lys
                485                 490                 495
```

Lys Leu Gly Tyr Thr Thr Gly His Ile Trp Ala Cys Pro Pro Ser Glu
            500                 505                 510

Gly Asp Asp Tyr Ile Phe His Cys His Pro Pro Asp Gln Lys Ile Pro
            515                 520                 525

Lys Pro Lys Arg Leu Gln Glu Trp Tyr Lys Lys Met Leu Asp Lys Ala
        530                 535                 540

Val Ser Glu Arg Ile Val His Asp Tyr Lys Asp Ile Phe Lys Gln Ala
545                 550                 555                 560

Thr Glu Asp Arg Leu Thr Ser Ala Lys Glu Leu Pro Tyr Phe Glu Gly
                565                 570                 575

Asp Phe Trp Pro Asn Val Leu Glu Glu Ser Ile Lys Glu Leu Glu Gln
            580                 585                 590

Glu Glu Glu Glu Arg Lys Arg Glu Glu Asn Thr Ser Asn Glu Ser Thr
        595                 600                 605

Asp Val Thr Lys Gly Asp Ser Lys Asn Ala Lys Lys Lys Asn Asn Lys
            610                 615                 620

Lys Thr Ser Lys Asn Lys Ser Ser Leu Ser Arg Gly Asn Lys Lys Lys
625                 630                 635                 640

Pro Gly Met Pro Asn Val Ser Asn Asp Leu Ser Gln Lys Leu Tyr Ala
                645                 650                 655

Thr Met Glu Lys His Lys Glu Val Phe Phe Val Ile Arg Leu Ile Ala
            660                 665                 670

Gly Pro Ala Ala Asn Ser Leu Pro Pro Ile Val Asp Pro Asp Pro Leu
            675                 680                 685

Ile Pro Cys Asp Leu Met Asp Gly Arg Asp Ala Phe Leu Thr Leu Ala
690                 695                 700

Arg Asp Lys His Leu Glu Phe Ser Ser Leu Arg Arg Ala Gln Trp Ser
705                 710                 715                 720

Thr Met Cys Met Leu Val Glu Leu His Thr Gln Ser Gln Asp Arg Phe
                725                 730                 735

Val Tyr Thr Cys Asn Glu Cys Tyr Pro Tyr Asp Val Pro Asp Tyr Ala
                740                 745                 750

<210> SEQ ID NO 16
<211> LENGTH: 491
<212> TYPE: PRT
<213> ORGANISM: Artificial Sequence
<220> FEATURE:
<223> OTHER INFORMATION: LexA-IN

<400> SEQUENCE: 16

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

-continued

```
Leu Arg Val Ser Gly Met Ser Met Lys Asp Ile Gly Ile Met Asp Gly
            115                 120                 125
Asp Leu Leu Ala Val His Lys Thr Gln Asp Val Arg Asn Gly Gln Val
        130                 135                 140
Val Val Ala Arg Ile Asp Asp Glu Val Thr Val Lys Arg Leu Lys Lys
145                 150                 155                 160
Gln Gly Asn Lys Val Glu Leu Leu Pro Glu Asn Ser Glu Phe Lys Pro
                165                 170                 175
Ile Val Val Asp Leu Arg Gln Gln Ser Phe Thr Ile Glu Gly Leu Ala
            180                 185                 190
Val Gly Val Ile Arg Asn Gly Asp Trp Leu Glu Phe Leu Asp Gly Ile
        195                 200                 205
Asp Lys Ala Gln Glu Glu His Glu Lys Tyr His Ser Asn Trp Arg Ala
210                 215                 220
Met Ala Ser Asp Phe Asn Leu Pro Pro Val Val Ala Lys Glu Ile Val
225                 230                 235                 240
Ala Ser Cys Asp Lys Cys Gln Leu Lys Gly Glu Ala Met His Gly Gln
                245                 250                 255
Val Asp Cys Ser Pro Gly Ile Trp Gln Leu Asp Cys Thr His Leu Glu
            260                 265                 270
Gly Lys Val Ile Leu Val Ala Val His Val Ala Ser Gly Tyr Ile Glu
        275                 280                 285
Ala Glu Val Ile Pro Ala Glu Thr Gly Gln Glu Thr Ala Tyr Phe Leu
    290                 295                 300
Leu Lys Leu Ala Gly Arg Trp Pro Val Lys Thr Val His Thr Asp Asn
305                 310                 315                 320
Gly Ser Asn Phe Thr Ser Thr Thr Val Lys Ala Ala Cys Trp Trp Ala
                325                 330                 335
Gly Ile Lys Gln Glu Phe Gly Ile Pro Tyr Asn Pro Gln Ser Gln Gly
            340                 345                 350
Val Ile Glu Ser Met Asn Lys Glu Leu Lys Lys Ile Ile Gly Gln Val
        355                 360                 365
Arg Asp Gln Ala Glu His Leu Lys Thr Ala Val Gln Met Ala Val Phe
    370                 375                 380
Ile His Asn Phe Lys Arg Lys Gly Gly Ile Gly Gly Tyr Ser Ala Gly
385                 390                 395                 400
Glu Arg Ile Val Asp Ile Ile Ala Thr Asp Ile Gln Thr Lys Glu Leu
                405                 410                 415
Gln Lys Gln Ile Thr Lys Ile Gln Asn Phe Arg Val Tyr Tyr Arg Asp
            420                 425                 430
Ser Arg Asp Pro Val Trp Lys Gly Pro Ala Lys Leu Leu Trp Lys Gly
        435                 440                 445
Glu Gly Ala Val Val Ile Gln Asp Asn Ser Asp Ile Lys Val Val Pro
    450                 455                 460
Arg Arg Lys Ala Lys Ile Ile Arg Asp Tyr Gly Lys Gln Met Ala Gly
465                 470                 475                 480
Asp Asp Cys Val Ala Ser Arg Gln Asp Glu Asp
                485                 490
```

<210> SEQ ID NO 17
<211> LENGTH: 599
<212> TYPE: PRT
<213> ORGANISM: Artificial Sequence
<220> FEATURE:
<223> OTHER INFORMATION: LexA-HistoneH3-Gcn5wt-HA

<400> SEQUENCE: 17

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu Glu Phe Pro Gly Ile Arg
        195                 200                 205

Arg Pro Ala Ala Asn Tyr Leu Phe Asp Asp Glu Asp Thr Pro Pro Asn
    210                 215                 220

Pro Lys Lys Glu Ile Glu Phe Gln Leu Thr Thr Met Phe Met Ala Arg
225                 230                 235                 240

Thr Lys Gln Thr Ala Arg Lys Ser Thr Gly Gly Lys Ala Pro Arg Lys
                245                 250                 255

Gln Leu Ala Ser Lys Ala Ala Arg Lys Ser Ala Pro Ser Thr Gly Gly
            260                 265                 270

Val Lys Lys Pro His Arg Tyr Lys Pro Gly Thr Val Ala Leu Arg Glu
        275                 280                 285

Ile Arg Arg Phe Gln Lys Ser Thr Glu Pro Gly Ser Pro Ile Leu Gly
    290                 295                 300

Tyr Trp Lys Gly Arg Arg Asp His Pro Pro Lys Ser Asp Leu Ile Glu
305                 310                 315                 320

Gly Arg Gly Asp Pro Glu Val Lys Arg Val Lys Leu Glu Asn Asn Val
                325                 330                 335

Glu Glu Ile Gln Pro Glu Gln Ala Glu Thr Asn Lys Gln Glu Gly Thr
            340                 345                 350

Asp Lys Glu Asn Lys Gly Lys Phe Glu Lys Glu Thr Glu Arg Ile Gly
        355                 360                 365

Gly Ser Glu Val Val Thr Asp Val Glu Lys Gly Ile Val Lys Phe Glu
    370                 375                 380

Phe Asp Gly Val Glu Tyr Thr Phe Lys Glu Arg Pro Ser Val Val Glu
385                 390                 395                 400

Glu Asn Glu Gly Lys Ile Glu Phe Arg Val Val Asn Asn Asp Asn Thr

-continued

```
                405                 410                 415
Lys Glu Asn Met Met Val Leu Thr Gly Leu Lys Asn Ile Phe Gln Lys
            420                 425                 430

Gln Leu Pro Lys Met Pro Lys Glu Tyr Ile Ala Arg Leu Val Tyr Asp
        435                 440                 445

Arg Ser His Leu Ser Met Ala Val Ile Arg Lys Pro Leu Thr Val Val
    450                 455                 460

Gly Gly Ile Thr Tyr Arg Pro Phe Asp Lys Arg Glu Phe Ala Glu Ile
465                 470                 475                 480

Val Phe Cys Ala Ile Ser Ser Thr Glu Gln Val Arg Gly Tyr Gly Ala
            485                 490                 495

His Leu Met Asn His Leu Lys Asp Tyr Val Arg Asn Thr Ser Asn Ile
        500                 505                 510

Lys Tyr Phe Leu Thr Tyr Ala Asp Asn Tyr Ala Ile Gly Tyr Phe Lys
    515                 520                 525

Lys Gln Gly Phe Thr Lys Glu Ile Thr Leu Asp Lys Ser Ile Trp Met
530                 535                 540

Gly Tyr Ile Lys Asp Tyr Glu Gly Gly Thr Leu Met Gln Cys Asn Met
545                 550                 555                 560

Ala Ile Pro Gly Gly Arg Ile Phe Tyr Pro Tyr Asp Val Pro Asp
            565                 570                 575

Tyr Ala Gly Tyr Pro Tyr Asp Val Pro Asp Tyr Ala Gly Ser Tyr Pro
        580                 585                 590

Tyr Asp Val Pro Asp Tyr Ala
        595

<210> SEQ ID NO 18
<211> LENGTH: 599
<212> TYPE: PRT
<213> ORGANISM: Artificial Sequence
<220> FEATURE:
<223> OTHER INFORMATION: LexA-HistoneH3-Gcn5mut-HA

<400> SEQUENCE: 18

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro Leu Leu Ala Gln Gln His Ile Glu Gly
            85                  90                  95

His Tyr Gln Val Asp Pro Ser Leu Phe Lys Pro Asn Ala Asp Phe Leu
        100                 105                 110

Leu Arg Val Ser Gly Met Ser Met Lys Asp Ile Gly Ile Met Asp Gly
    115                 120                 125

Asp Leu Leu Ala Val His Lys Thr Gln Asp Val Arg Asn Gly Gln Val
130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
```

```
            165                 170                 175
Ile Val Val Asp Leu Arg Gln Gln Ser Phe Thr Ile Glu Gly Leu Ala
            180                 185                 190

Val Gly Val Ile Arg Asn Gly Asp Trp Leu Glu Phe Pro Gly Ile Arg
            195                 200                 205

Arg Pro Ala Ala Asn Tyr Leu Phe Asp Asp Glu Asp Thr Pro Pro Asn
            210                 215                 220

Pro Lys Lys Glu Ile Glu Phe Gln Leu Thr Thr Met Phe Met Ala Arg
225                 230                 235                 240

Thr Lys Gln Thr Ala Arg Lys Ser Thr Gly Gly Lys Ala Pro Arg Lys
                245                 250                 255

Gln Leu Ala Ser Lys Ala Ala Arg Lys Ser Ala Pro Ser Thr Gly Gly
                260                 265                 270

Val Lys Lys Pro His Arg Tyr Lys Pro Gly Thr Val Ala Leu Arg Glu
                275                 280                 285

Ile Arg Arg Phe Gln Lys Ser Thr Glu Pro Gly Ser Pro Ile Leu Gly
                290                 295                 300

Tyr Trp Lys Gly Arg Arg Asp His Pro Pro Lys Ser Asp Leu Ile Glu
305                 310                 315                 320

Gly Arg Gly Asp Pro Glu Val Lys Arg Val Lys Leu Glu Asn Asn Val
                325                 330                 335

Glu Glu Ile Gln Pro Glu Gln Ala Glu Thr Asn Lys Gln Glu Gly Thr
                340                 345                 350

Asp Lys Glu Asn Lys Gly Lys Phe Glu Lys Glu Thr Glu Arg Ile Gly
                355                 360                 365

Gly Ser Glu Val Val Thr Asp Val Glu Lys Gly Ile Val Lys Phe Glu
                370                 375                 380

Phe Asp Gly Val Glu Tyr Thr Phe Lys Glu Arg Pro Ser Val Val Glu
385                 390                 395                 400

Glu Asn Glu Gly Lys Ile Glu Phe Arg Val Val Asn Asn Asp Asn Thr
                405                 410                 415

Lys Glu Asn Met Met Val Leu Thr Gly Leu Lys Asn Ile Phe Gln Lys
                420                 425                 430

Gln Leu Pro Lys Met Pro Lys Glu Tyr Ile Ala Arg Leu Val Tyr Asp
                435                 440                 445

Arg Ser His Leu Ser Met Ala Val Ile Arg Lys Pro Leu Thr Val Val
                450                 455                 460

Gly Gly Ile Thr Tyr Arg Pro Phe Asp Lys Arg Glu Phe Ala Glu Ile
465                 470                 475                 480

Val Phe Cys Ala Ile Ser Ser Thr Glu Gln Val Arg Gly Tyr Gly Ala
                485                 490                 495

His Leu Met Asn His Leu Lys Asp Tyr Val Arg Asn Thr Ser Asn Ile
                500                 505                 510

Lys Tyr Phe Leu Thr Tyr Ala Asp Asn Tyr Ala Ile Gly Tyr Ala Lys
                515                 520                 525

Lys Gln Gly Phe Thr Lys Glu Ile Thr Leu Asp Lys Ser Ile Trp Met
                530                 535                 540

Gly Tyr Ile Lys Asp Tyr Glu Gly Gly Thr Leu Met Gln Cys Asn Met
545                 550                 555                 560

Ala Ile Pro Gly Gly Gly Arg Ile Phe Tyr Pro Tyr Asp Val Pro Asp
                565                 570                 575

Tyr Ala Gly Tyr Pro Tyr Asp Val Pro Asp Tyr Ala Gly Ser Tyr Pro
                580                 585                 590
```

Tyr Asp Val Pro Asp Tyr Ala
            595

<210> SEQ ID NO 19
<211> LENGTH: 511
<212> TYPE: PRT
<213> ORGANISM: Artificial Sequence
<220> FEATURE:
<223> OTHER INFORMATION: LexA-Gcn5wt-HA

<400> SEQUENCE: 19

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu Glu Phe Pro Gly Ile Arg
        195                 200                 205

Arg Pro Gly Ser Pro Ile Leu Gly Tyr Trp Lys Gly Arg Arg Asp His
    210                 215                 220

Pro Pro Lys Ser Asp Leu Ile Glu Gly Arg Gly Asp Pro Glu Val Lys
225                 230                 235                 240

Arg Val Lys Leu Glu Asn Asn Val Glu Glu Ile Gln Pro Glu Gln Ala
                245                 250                 255

Glu Thr Asn Lys Gln Glu Gly Thr Asp Lys Glu Asn Lys Gly Lys Phe
            260                 265                 270

Glu Lys Glu Thr Glu Arg Ile Gly Gly Ser Glu Val Val Thr Asp Val
        275                 280                 285

Glu Lys Gly Ile Val Lys Phe Glu Phe Asp Gly Val Glu Tyr Thr Phe
    290                 295                 300

Lys Glu Arg Pro Ser Val Val Glu Glu Asn Glu Gly Lys Ile Glu Phe
305                 310                 315                 320

Arg Val Val Asn Asn Asp Asn Thr Lys Glu Asn Met Met Val Leu Thr
                325                 330                 335

Gly Leu Lys Asn Ile Phe Gln Lys Gln Leu Pro Lys Met Pro Lys Glu
            340                 345                 350

```
Tyr Ile Ala Arg Leu Val Tyr Asp Arg Ser His Leu Ser Met Ala Val
        355                 360                 365

Ile Arg Lys Pro Leu Thr Val Val Gly Gly Ile Thr Tyr Arg Pro Phe
    370                 375                 380

Asp Lys Arg Glu Phe Ala Glu Ile Val Phe Cys Ala Ile Ser Ser Thr
385                 390                 395                 400

Glu Gln Val Arg Gly Tyr Gly Ala His Leu Met Asn His Leu Lys Asp
                405                 410                 415

Tyr Val Arg Asn Thr Ser Asn Ile Lys Tyr Phe Leu Thr Tyr Ala Asp
                420                 425                 430

Asn Tyr Ala Ile Gly Tyr Phe Lys Lys Gln Gly Phe Thr Lys Glu Ile
            435                 440                 445

Thr Leu Asp Lys Ser Ile Trp Met Gly Tyr Ile Lys Asp Tyr Glu Gly
    450                 455                 460

Gly Thr Leu Met Gln Cys Asn Met Ala Ile Pro Gly Gly Arg Ile
465                 470                 475                 480

Phe Tyr Pro Tyr Asp Val Pro Asp Tyr Ala Gly Tyr Pro Tyr Asp Val
                485                 490                 495

Pro Asp Tyr Ala Gly Ser Tyr Pro Tyr Asp Val Pro Asp Tyr Ala
                500                 505                 510

<210> SEQ ID NO 20
<211> LENGTH: 511
<212> TYPE: PRT
<213> ORGANISM: Artificial Sequence
<220> FEATURE:
<223> OTHER INFORMATION: LexA-Gcn5mut-HA

<400> SEQUENCE: 20

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
                20                  25                  30

Gln Arg Leu Gly Phe Arg Ser Pro Asn Ala Ala Glu Glu His Leu Lys
            35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
                100                 105                 110

Leu Arg Val Ser Gly Met Ser Met Lys Asp Ile Gly Ile Met Asp Gly
            115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
                180                 185                 190

Val Gly Val Ile Arg Asn Gly Asp Trp Leu Glu Phe Pro Gly Ile Arg
            195                 200                 205
```

```
Arg Pro Gly Ser Pro Ile Leu Gly Tyr Trp Lys Gly Arg Arg Asp His
    210                 215                 220

Pro Pro Lys Ser Asp Leu Ile Glu Gly Arg Gly Asp Pro Glu Val Lys
225                 230                 235                 240

Arg Val Lys Leu Glu Asn Asn Val Glu Ile Gln Pro Glu Gln Ala
                245                 250                 255

Glu Thr Asn Lys Gln Glu Gly Thr Asp Lys Glu Asn Lys Gly Lys Phe
                260                 265                 270

Glu Lys Glu Thr Glu Arg Ile Gly Gly Ser Glu Val Val Thr Asp Val
            275                 280                 285

Glu Lys Gly Ile Val Lys Phe Glu Phe Asp Gly Val Glu Tyr Thr Phe
        290                 295                 300

Lys Glu Arg Pro Ser Val Val Glu Glu Asn Gly Lys Ile Glu Phe
305                 310                 315                 320

Arg Val Val Asn Asn Asp Asn Thr Lys Glu Asn Met Met Val Leu Thr
                325                 330                 335

Gly Leu Lys Asn Ile Phe Gln Lys Gln Leu Pro Lys Met Pro Lys Glu
                340                 345                 350

Tyr Ile Ala Arg Leu Val Tyr Asp Arg Ser His Leu Ser Met Ala Val
            355                 360                 365

Ile Arg Lys Pro Leu Thr Val Val Gly Gly Ile Thr Tyr Arg Pro Phe
        370                 375                 380

Asp Lys Arg Glu Phe Ala Glu Ile Val Phe Cys Ala Ile Ser Ser Thr
385                 390                 395                 400

Glu Gln Val Arg Gly Tyr Gly Ala His Leu Met Asn His Leu Lys Asp
                405                 410                 415

Tyr Val Arg Asn Thr Ser Asn Ile Lys Tyr Phe Leu Thr Tyr Ala Asp
                420                 425                 430

Asn Tyr Ala Ile Gly Tyr Ala Lys Lys Gln Gly Phe Thr Lys Glu Ile
            435                 440                 445

Thr Leu Asp Lys Ser Ile Trp Met Gly Tyr Ile Lys Asp Tyr Glu Gly
        450                 455                 460

Gly Thr Leu Met Gln Cys Asn Met Ala Ile Pro Gly Gly Gly Arg Ile
465                 470                 475                 480

Phe Tyr Pro Tyr Asp Val Pro Asp Tyr Ala Gly Tyr Pro Tyr Asp Val
                485                 490                 495

Pro Asp Tyr Ala Gly Ser Tyr Pro Tyr Asp Val Pro Asp Tyr Ala
            500                 505                 510

<210> SEQ ID NO 21
<211> LENGTH: 297
<212> TYPE: PRT
<213> ORGANISM: Artificial Sequence
<220> FEATURE:
<223> OTHER INFORMATION: LexA-H3Histone

<400> SEQUENCE: 21

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
                20                  25                  30

Gln Arg Leu Gly Phe Arg Ser Pro Asn Ala Ala Glu Glu His Leu Lys
            35                  40                  45

Ala Leu Ala Arg Lys Gly Val Ile Glu Ile Val Ser Gly Ala Ser Arg
        50                  55                  60
```

Gly Ile Arg Leu Leu Gln Glu Glu Glu Gly Leu Pro Leu Val Gly
65                  70                  75                  80

Arg Val Ala Ala Gly Glu Pro Leu Leu Ala Gln Gln His Ile Glu Gly
            85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
            115                 120                 125

Asp Leu Leu Ala Val His Lys Thr Gln Asp Val Arg Asn Gly Gln Val
130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
            165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu Glu Phe Pro Gly Ile Arg
            195                 200                 205

Arg Pro Ala Ala Asn Tyr Leu Phe Asp Asp Glu Asp Thr Pro Pro Asn
210                 215                 220

Pro Lys Lys Glu Ile Glu Phe Gln Leu Thr Thr Met Phe Met Ala Arg
225                 230                 235                 240

Thr Lys Gln Thr Ala Arg Lys Ser Thr Gly Gly Lys Ala Pro Arg Lys
            245                 250                 255

Gln Leu Ala Ser Lys Ala Ala Arg Lys Ser Ala Pro Ser Thr Gly Gly
            260                 265                 270

Val Lys Lys Pro His Arg Tyr Lys Pro Gly Thr Val Ala Leu Arg Glu
            275                 280                 285

Ile Arg Arg Phe Gln Lys Ser Thr Glu
    290                 295

<210> SEQ ID NO 22
<211> LENGTH: 24
<212> TYPE: DNA
<213> ORGANISM: Artificial Sequence
<220> FEATURE:
<223> OTHER INFORMATION: synthetic primer

<400> SEQUENCE: 22
agactctccc ctgttgaagc tctt                                          24

<210> SEQ ID NO 23
<211> LENGTH: 27
<212> TYPE: DNA
<213> ORGANISM: Artificial Sequence
<220> FEATURE:
<223> OTHER INFORMATION: synthetic primer

<400> SEQUENCE: 23
tgaagattct gtaggggcca ctgtctt                                       27

<210> SEQ ID NO 24
<211> LENGTH: 37
<212> TYPE: DNA
<213> ORGANISM: Artificial Sequence
<220> FEATURE:
<223> OTHER INFORMATION: synthetic primer

<400> SEQUENCE: 24
gccgcgcgca tgcccaggtg cagctggtgc agtctgg					37

<210> SEQ ID NO 25
<211> LENGTH: 37
<212> TYPE: DNA
<213> ORGANISM: Artificial Sequence
<220> FEATURE:
<223> OTHER INFORMATION: synthetic primer

<400> SEQUENCE: 25
gccgcgcgca tgcccaggtc aacttaaggg agtctgg					37

<210> SEQ ID NO 26
<211> LENGTH: 37
<212> TYPE: DNA
<213> ORGANISM: Artificial Sequence
<220> FEATURE:
<223> OTHER INFORMATION: synthetic primer

<400> SEQUENCE: 26
gccgcgcgca tgccgaggtg cagctggtgg agtctgg					37

<210> SEQ ID NO 27
<211> LENGTH: 37
<212> TYPE: DNA
<213> ORGANISM: Artificial Sequence
<220> FEATURE:
<223> OTHER INFORMATION: synthetic primer

<400> SEQUENCE: 27
gccgcgcgca tgcccaggtg cagctgcagg agtcggg					37

<210> SEQ ID NO 28
<211> LENGTH: 37
<212> TYPE: DNA
<213> ORGANISM: Artificial Sequence
<220> FEATURE:
<223> OTHER INFORMATION: synthetic primer

<400> SEQUENCE: 28
gccgcgcgca tgccgaggtg cagctgttgc agtctgc					37

<210> SEQ ID NO 29
<211> LENGTH: 37
<212> TYPE: DNA
<213> ORGANISM: Artificial Sequence
<220> FEATURE:
<223> OTHER INFORMATION: synthetic primer

<400> SEQUENCE: 29
gccgcgcgca tgcccaggta cagctgcagc agtcagg					37

<210> SEQ ID NO 30
<211> LENGTH: 24
<212> TYPE: DNA
<213> ORGANISM: Artificial Sequence
<220> FEATURE:
<223> OTHER INFORMATION: synthetic primer

<400> SEQUENCE: 30
tgaggagacg gtgaccaggg tgcc					24

<210> SEQ ID NO 31
<211> LENGTH: 24
<212> TYPE: DNA

```
<213> ORGANISM: Artificial Sequence
<220> FEATURE:
<223> OTHER INFORMATION: synthetic primer

<400> SEQUENCE: 31
tgaagagacg gtgaccattg tccc                                              24

<210> SEQ ID NO 32
<211> LENGTH: 24
<212> TYPE: DNA
<213> ORGANISM: Artificial Sequence
<220> FEATURE:
<223> OTHER INFORMATION: synthetic primer

<400> SEQUENCE: 32
tgaggagacg gtgaccaggg ttcc                                              24

<210> SEQ ID NO 33
<211> LENGTH: 24
<212> TYPE: DNA
<213> ORGANISM: Artificial Sequence
<220> FEATURE:
<223> OTHER INFORMATION: synthetic primer

<400> SEQUENCE: 33
tgaggagacg gtgaccgtgg tccc                                              24

<210> SEQ ID NO 34
<211> LENGTH: 37
<212> TYPE: DNA
<213> ORGANISM: Artificial Sequence
<220> FEATURE:
<223> OTHER INFORMATION: synthetic primer

<400> SEQUENCE: 34
cggccgcgct agctgaggag acggtgacca gggtgcc                                37

<210> SEQ ID NO 35
<211> LENGTH: 37
<212> TYPE: DNA
<213> ORGANISM: Artificial Sequence
<220> FEATURE:
<223> OTHER INFORMATION: synthetic primer

<400> SEQUENCE: 35
cggccgcgct agctgaagag acggtgacca ttgtccc                                37

<210> SEQ ID NO 36
<211> LENGTH: 37
<212> TYPE: DNA
<213> ORGANISM: Artificial Sequence
<220> FEATURE:
<223> OTHER INFORMATION: synthetic primer

<400> SEQUENCE: 36
cggccgcgct agctgaggag acggtgacca gggttcc                                37

<210> SEQ ID NO 37
<211> LENGTH: 37
<212> TYPE: DNA
<213> ORGANISM: Artificial Sequence
<220> FEATURE:
<223> OTHER INFORMATION: synthetic primer

<400> SEQUENCE: 37
cggccgcgct agctgaggag acggtgaccg tggtccc                                37
```

<210> SEQ ID NO 38
<211> LENGTH: 23
<212> TYPE: DNA
<213> ORGANISM: Artificial Sequence
<220> FEATURE:
<223> OTHER INFORMATION: synthetic primer

<400> SEQUENCE: 38
gacatccaga tgacccagtc tcc                                              23

<210> SEQ ID NO 39
<211> LENGTH: 23
<212> TYPE: DNA
<213> ORGANISM: Artificial Sequence
<220> FEATURE:
<223> OTHER INFORMATION: synthetic primer

<400> SEQUENCE: 39
gatgttgtga tgactcagtc tcc                                              23

<210> SEQ ID NO 40
<211> LENGTH: 23
<212> TYPE: DNA
<213> ORGANISM: Artificial Sequence
<220> FEATURE:
<223> OTHER INFORMATION: synthetic primer

<400> SEQUENCE: 40
gaaattgtgt tgacgcagtc tcc                                              23

<210> SEQ ID NO 41
<211> LENGTH: 23
<212> TYPE: DNA
<213> ORGANISM: Artificial Sequence
<220> FEATURE:
<223> OTHER INFORMATION: synthetic primer

<400> SEQUENCE: 41
gacatcgtga tgacccagtc tcc                                              23

<210> SEQ ID NO 42
<211> LENGTH: 23
<212> TYPE: DNA
<213> ORGANISM: Artificial Sequence
<220> FEATURE:
<223> OTHER INFORMATION: synthetic primer

<400> SEQUENCE: 42
gaaacgacac tcacgcagtc tcc                                              23

<210> SEQ ID NO 43
<211> LENGTH: 23
<212> TYPE: DNA
<213> ORGANISM: Artificial Sequence
<220> FEATURE:
<223> OTHER INFORMATION: synthetic primer

<400> SEQUENCE: 43
gaaattgtgc tgactcagtc tcc                                              23

<210> SEQ ID NO 44
<211> LENGTH: 37
<212> TYPE: DNA
<213> ORGANISM: Artificial Sequence
<220> FEATURE:

```
<223> OTHER INFORMATION: synthetic primer

<400> SEQUENCE: 44
cggccgcgct agcacgtttg atttccacct tggtccc                              37

<210> SEQ ID NO 45
<211> LENGTH: 37
<212> TYPE: DNA
<213> ORGANISM: Artificial Sequence
<220> FEATURE:
<223> OTHER INFORMATION: synthetic primer

<400> SEQUENCE: 45
cggccgcgct agcacgtttg atctccagct tggtccc                              37

<210> SEQ ID NO 46
<211> LENGTH: 37
<212> TYPE: DNA
<213> ORGANISM: Artificial Sequence
<220> FEATURE:
<223> OTHER INFORMATION: synthetic primer

<400> SEQUENCE: 46
cggccgcgct agcacgtttg atatccactt tggtccc                              37

<210> SEQ ID NO 47
<211> LENGTH: 37
<212> TYPE: DNA
<213> ORGANISM: Artificial Sequence
<220> FEATURE:
<223> OTHER INFORMATION: synthetic primer

<400> SEQUENCE: 47
cggccgcgct agcacgtttg atctccacct tggtccc                              37

<210> SEQ ID NO 48
<211> LENGTH: 37
<212> TYPE: DNA
<213> ORGANISM: Artificial Sequence
<220> FEATURE:
<223> OTHER INFORMATION: synthetic primer

<400> SEQUENCE: 48
cggccgcgct agcacgttta atctccagtc gtgtccc                              37

<210> SEQ ID NO 49
<211> LENGTH: 23
<212> TYPE: DNA
<213> ORGANISM: Artificial Sequence
<220> FEATURE:
<223> OTHER INFORMATION: synthetic primer

<400> SEQUENCE: 49
cagtctgtgt tgacgcagcc gcc                                              23

<210> SEQ ID NO 50
<211> LENGTH: 23
<212> TYPE: DNA
<213> ORGANISM: Artificial Sequence
<220> FEATURE:
<223> OTHER INFORMATION: synthetic primer

<400> SEQUENCE: 50
cagtctgccc tgactcagcc tgc                                              23
```

```
<210> SEQ ID NO 51
<211> LENGTH: 23
<212> TYPE: DNA
<213> ORGANISM: Artificial Sequence
<220> FEATURE:
<223> OTHER INFORMATION: synthetic primer

<400> SEQUENCE: 51
tcctatgtgc tgactcagcc acc                                            23

<210> SEQ ID NO 52
<211> LENGTH: 23
<212> TYPE: DNA
<213> ORGANISM: Artificial Sequence
<220> FEATURE:
<223> OTHER INFORMATION: synthetic primer

<400> SEQUENCE: 52
tcttctgagc tgactcagga ccc                                            23

<210> SEQ ID NO 53
<211> LENGTH: 23
<212> TYPE: DNA
<213> ORGANISM: Artificial Sequence
<220> FEATURE:
<223> OTHER INFORMATION: synthetic primer

<400> SEQUENCE: 53
cacgttatac tgactcaacc gcc                                            23

<210> SEQ ID NO 54
<211> LENGTH: 23
<212> TYPE: DNA
<213> ORGANISM: Artificial Sequence
<220> FEATURE:
<223> OTHER INFORMATION: synthetic primer

<400> SEQUENCE: 54
caggctgtgc tcactcagcc gtc                                            23

<210> SEQ ID NO 55
<211> LENGTH: 23
<212> TYPE: DNA
<213> ORGANISM: Artificial Sequence
<220> FEATURE:
<223> OTHER INFORMATION: synthetic primer

<400> SEQUENCE: 55
aattttatgc tgactcagcc cca                                            23

<210> SEQ ID NO 56
<211> LENGTH: 37
<212> TYPE: DNA
<213> ORGANISM: Artificial Sequence
<220> FEATURE:
<223> OTHER INFORMATION: synthetic primer

<400> SEQUENCE: 56
cggccgcgct agcacctagg acggtgacct tggtccc                             37

<210> SEQ ID NO 57
<211> LENGTH: 37
<212> TYPE: DNA
<213> ORGANISM: Artificial Sequence
<220> FEATURE:
<223> OTHER INFORMATION: synthetic primer
```

```
<400> SEQUENCE: 57
cggccgcgct agcacctagg acggtcagct tggtccc                               37

<210> SEQ ID NO 58
<211> LENGTH: 37
<212> TYPE: DNA
<213> ORGANISM: Artificial Sequence
<220> FEATURE:
<223> OTHER INFORMATION: synthetic primer

<400> SEQUENCE: 58
cggccgcgct agcacctaaa acggtgagct gggtccc                               37

<210> SEQ ID NO 59
<211> LENGTH: 22
<212> TYPE: DNA
<213> ORGANISM: Artificial Sequence
<220> FEATURE:
<223> OTHER INFORMATION: synthetic primer

<400> SEQUENCE: 59
ggtggaggcg gttcaggcgg ag                                               22

<210> SEQ ID NO 60
<211> LENGTH: 23
<212> TYPE: DNA
<213> ORGANISM: Artificial Sequence
<220> FEATURE:
<223> OTHER INFORMATION: synthetic primer

<400> SEQUENCE: 60
cgatccgcca ccgccagagc cac                                              23

<210> SEQ ID NO 61
<211> LENGTH: 28
<212> TYPE: DNA
<213> ORGANISM: Artificial Sequence
<220> FEATURE:
<223> OTHER INFORMATION: synthetic primer

<400> SEQUENCE: 61
gcaccctggt caccgtctcc tcaggtgg                                         28

<210> SEQ ID NO 62
<211> LENGTH: 28
<212> TYPE: DNA
<213> ORGANISM: Artificial Sequence
<220> FEATURE:
<223> OTHER INFORMATION: synthetic primer

<400> SEQUENCE: 62
ggacaatggt caccgtctct tcaggtgg                                         28

<210> SEQ ID NO 63
<211> LENGTH: 28
<212> TYPE: DNA
<213> ORGANISM: Artificial Sequence
<220> FEATURE:
<223> OTHER INFORMATION: synthetic primer

<400> SEQUENCE: 63
gaaccctggt caccgtctcc tcaggtgg                                         28

<210> SEQ ID NO 64
<211> LENGTH: 28
```

```
<212> TYPE: DNA
<213> ORGANISM: Artificial Sequence
<220> FEATURE:
<223> OTHER INFORMATION: synthetic primer

<400> SEQUENCE: 64
ggaccacggt caccgtctcc tcaggtgg                                    28

<210> SEQ ID NO 65
<211> LENGTH: 32
<212> TYPE: DNA
<213> ORGANISM: Artificial Sequence
<220> FEATURE:
<223> OTHER INFORMATION: synthetic primer

<400> SEQUENCE: 65
ggagactggg tcatctggat gtccgatccg cc                               32

<210> SEQ ID NO 66
<211> LENGTH: 32
<212> TYPE: DNA
<213> ORGANISM: Artificial Sequence
<220> FEATURE:
<223> OTHER INFORMATION: synthetic primer

<400> SEQUENCE: 66
ggagactgag tcatcacaac atccgatccg cc                               32

<210> SEQ ID NO 67
<211> LENGTH: 32
<212> TYPE: DNA
<213> ORGANISM: Artificial Sequence
<220> FEATURE:
<223> OTHER INFORMATION: synthetic primer

<400> SEQUENCE: 67
ggagactgcg tcaacacaat ttccgatccg cc                               32

<210> SEQ ID NO 68
<211> LENGTH: 32
<212> TYPE: DNA
<213> ORGANISM: Artificial Sequence
<220> FEATURE:
<223> OTHER INFORMATION: synthetic primer

<400> SEQUENCE: 68
ggagactggg tcatcacgat gtccgatccg cc                               32

<210> SEQ ID NO 69
<211> LENGTH: 32
<212> TYPE: DNA
<213> ORGANISM: Artificial Sequence
<220> FEATURE:
<223> OTHER INFORMATION: synthetic primer

<400> SEQUENCE: 69
ggagactgcg tgagtgtcgt ttccgatccg cc                               32

<210> SEQ ID NO 70
<211> LENGTH: 32
<212> TYPE: DNA
<213> ORGANISM: Artificial Sequence
<220> FEATURE:
<223> OTHER INFORMATION: synthetic primer

<400> SEQUENCE: 70
```

```
ggagactgag tcagcacaat ttccgatccg cc                                         32

<210> SEQ ID NO 71
<211> LENGTH: 42
<212> TYPE: DNA
<213> ORGANISM: Artificial Sequence
<220> FEATURE:
<223> OTHER INFORMATION: synthetic primer

<400> SEQUENCE: 71
ggcggctgcg tcaacacaga ctgcgatccg ccaccgccag ag                              42

<210> SEQ ID NO 72
<211> LENGTH: 42
<212> TYPE: DNA
<213> ORGANISM: Artificial Sequence
<220> FEATURE:
<223> OTHER INFORMATION: synthetic primer

<400> SEQUENCE: 72
gcaggctgag tcagagcaga ctgcgatccg ccaccgccag ag                              42

<210> SEQ ID NO 73
<211> LENGTH: 42
<212> TYPE: DNA
<213> ORGANISM: Artificial Sequence
<220> FEATURE:
<223> OTHER INFORMATION: synthetic primer

<400> SEQUENCE: 73
ggtggctgag tcagcacata ggacgatccg ccaccgccag ag                              42

<210> SEQ ID NO 74
<211> LENGTH: 42
<212> TYPE: DNA
<213> ORGANISM: Artificial Sequence
<220> FEATURE:
<223> OTHER INFORMATION: synthetic primer

<400> SEQUENCE: 74
gggtcctgag tcagctcaga agacgatccg ccaccgccag ag                              42

<210> SEQ ID NO 75
<211> LENGTH: 42
<212> TYPE: DNA
<213> ORGANISM: Artificial Sequence
<220> FEATURE:
<223> OTHER INFORMATION: synthetic primer

<400> SEQUENCE: 75
ggcggttgag tcagtataac gtgcgatccg ccaccgccag ag                              42

<210> SEQ ID NO 76
<211> LENGTH: 42
<212> TYPE: DNA
<213> ORGANISM: Artificial Sequence
<220> FEATURE:
<223> OTHER INFORMATION: synthetic primer

<400> SEQUENCE: 76
gacggctgag tcagcacaga ctgcgatccg ccaccgccag ag                              42

<210> SEQ ID NO 77
<211> LENGTH: 42
<212> TYPE: DNA
<213> ORGANISM: Artificial Sequence
```

-continued

```
<220> FEATURE:
<223> OTHER INFORMATION: synthetic primer

<400> SEQUENCE: 77
tggggctgag tcagcataaa attcgatccg ccaccgccag ag                          42

<210> SEQ ID NO 78
<211> LENGTH: 297
<212> TYPE: PRT
<213> ORGANISM: Artificial Sequence
<220> FEATURE:
<223> OTHER INFORMATION: LexA-AcK9H3Histone (PISA 2.0) PROTEIN
<220> FEATURE:
<221> NAME/KEY: ACT_SITE
<222> LOCATION: (247)..(247)

<400> SEQUENCE: 78
```

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu Glu Phe Pro Gly Ile Arg
        195                 200                 205

Arg Pro Ala Ala Asn Tyr Leu Phe Asp Asp Glu Asp Thr Pro Pro Asn
    210                 215                 220

Pro Lys Lys Glu Ile Glu Phe Gln Leu Thr Thr Met Phe Met Ala Arg
225                 230                 235                 240

Thr Lys Gln Thr Ala Arg Lys Ser Thr Gly Gly Lys Ala Pro Arg Lys
                245                 250                 255

Gln Leu Ala Ser Lys Ala Ala Arg Lys Ser Ala Pro Ser Thr Gly Gly
            260                 265                 270

Val Lys Lys Pro His Arg Tyr Lys Pro Gly Thr Val Ala Leu Arg Glu
        275                 280                 285

Ile Arg Arg Phe Gln Lys Ser Thr Glu
    290                 295

```
<210> SEQ ID NO 79
```

<211> LENGTH: 900
<212> TYPE: DNA
<213> ORGANISM: Artificial Sequence
<220> FEATURE:
<223> OTHER INFORMATION: LexA-AcK9H3Histone (PISA 2.0) DNA

<400> SEQUENCE: 79

```
atgaaagcgc tgaccgcgcg ccagcaggaa gtgtttgatc tgattcgcga tcatattagc      60
cagaccggca tgccgccgac ccgcgcggaa attgcgcagc gcctgggctt tcgcagcccg     120
aacgcggcgg aagaacatct gaaagcgctg gcgcgcaaag gcgtgattga aattgtgagc     180
ggcgcgagcc gcggcattcg cctgctgcag gaagaagaag aaggcctgcc gctggtgggc     240
cgcgtggcgg cgggcgaacc gctgctggcg cagcagcata ttgaaggcca ttatcaggtg     300
gatccgagcc tgtttaaacc gaacgcggat tttctgctgc gcgtgagcgg catgagcatg     360
aaagatattg gcattatgga tggcgatctg ctggcggtgc ataaaaccca ggatgtgcgc     420
aacggccagg tggtggtggc gcgcattgat gatgaagtga ccgtgaaacg cctgaaaaaa     480
cagggcaaca aagtggaact gctgccgaaa acagcgaatt taaaccgat tgtggtggat      540
ctgcgccagc agagctttac cattgaaggc ctggcggtgg gcgtgattcg caacggcgat     600
tggctggaat ttccgggcat tcgccgcccg gcggcgaact atctgtttga tgatgaagat     660
accccgccga cccgaaaaa agaaattgaa tttcagctga ccaccatgtt tatggcgcgc     720
accaaacaga ccgcgcgcgc gtgctagagc accggcggca aagcgccgcg caaacagctg     780
gcgagcaaag cggcgcgcaa agcgcgccg agcaccggcg gcgtgaaaaa accgcatcgc     840
tataaaccgg gcaccgtggc gctgcgcgaa attcgccgct ttcagaaaag caccgaataa     900
```

<210> SEQ ID NO 80
<211> LENGTH: 7
<212> TYPE: PRT
<213> ORGANISM: Artificial Sequence
<220> FEATURE:
<223> OTHER INFORMATION: ScFv-58F CDRH1

<400> SEQUENCE: 80

Gly Phe Thr Phe Ser Asn Tyr
1               5

<210> SEQ ID NO 81
<211> LENGTH: 8
<212> TYPE: PRT
<213> ORGANISM: Artificial Sequence
<220> FEATURE:
<223> OTHER INFORMATION: ScFv-58F CDRH2

<400> SEQUENCE: 81

Arg Leu Lys Ser Asn Asn Tyr Ala
1               5

<210> SEQ ID NO 82
<211> LENGTH: 11
<212> TYPE: PRT
<213> ORGANISM: Artificial Sequence
<220> FEATURE:
<223> OTHER INFORMATION: ScFv-58F CDRH3

<400> SEQUENCE: 82

Arg Asn Gly Pro Ser Ser Arg Ala Met Asp Tyr
1               5                   10

<210> SEQ ID NO 83

```
<211> LENGTH: 12
<212> TYPE: PRT
<213> ORGANISM: Artificial Sequence
<220> FEATURE:
<223> OTHER INFORMATION: ScFv-58F CDRL1

<400> SEQUENCE: 83

Arg Ala Ser Ser Ser Val Ser Ser Ser Tyr Leu His
1               5                   10

<210> SEQ ID NO 84
<211> LENGTH: 7
<212> TYPE: PRT
<213> ORGANISM: Artificial Sequence
<220> FEATURE:
<223> OTHER INFORMATION: ScFv-58F CDRL2

<400> SEQUENCE: 84

Ser Thr Ser Asn Leu Ala Ser
1               5

<210> SEQ ID NO 85
<211> LENGTH: 9
<212> TYPE: PRT
<213> ORGANISM: Artificial Sequence
<220> FEATURE:
<223> OTHER INFORMATION: ScFv-58F CDRL3

<400> SEQUENCE: 85

Gln Gln Tyr Ser Gly Tyr Pro Trp Thr
1               5

<210> SEQ ID NO 86
<211> LENGTH: 7
<212> TYPE: PRT
<213> ORGANISM: Artificial Sequence
<220> FEATURE:
<223> OTHER INFORMATION: VH-112A CDR1

<400> SEQUENCE: 86

Gly Tyr Thr Phe Thr Asn His
1               5

<210> SEQ ID NO 87
<211> LENGTH: 6
<212> TYPE: PRT
<213> ORGANISM: Artificial Sequence
<220> FEATURE:
<223> OTHER INFORMATION: VH-112A CDR2

<400> SEQUENCE: 87

Asn Pro Ser Thr Gly Tyr
1               5

<210> SEQ ID NO 88
<211> LENGTH: 10
<212> TYPE: PRT
<213> ORGANISM: Artificial Sequence
<220> FEATURE:
<223> OTHER INFORMATION: VH-112A CDR3

<400> SEQUENCE: 88

Tyr Tyr Gly Ser Ser Tyr Ala Met Asp Tyr
1               5                   10

<210> SEQ ID NO 89
<211> LENGTH: 7
```

```
<212> TYPE: PRT
<213> ORGANISM: Artificial Sequence
<220> FEATURE:
<223> OTHER INFORMATION: VH-12A CDR1

<400> SEQUENCE: 89

Gly Phe Asn Ile Lys Asp Thr
1               5

<210> SEQ ID NO 90
<211> LENGTH: 6
<212> TYPE: PRT
<213> ORGANISM: Artificial Sequence
<220> FEATURE:
<223> OTHER INFORMATION: VH-12A CDR2

<400> SEQUENCE: 90

Asp Pro Ala Asn Gly Asn
1               5

<210> SEQ ID NO 91
<211> LENGTH: 3
<212> TYPE: PRT
<213> ORGANISM: Artificial Sequence
<220> FEATURE:
<223> OTHER INFORMATION: VH-12A CDR3

<400> SEQUENCE: 91

Leu Leu Trp
1

<210> SEQ ID NO 92
<211> LENGTH: 122
<212> TYPE: PRT
<213> ORGANISM: Artificial Sequence
<220> FEATURE:
<223> OTHER INFORMATION: ScFv-58F VH

<400> SEQUENCE: 92

Glu Val Lys Val Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Ser Glu Ser Ser
65                  70                  75                  80

Val Tyr Leu Gln Met Asn Asn Leu Arg Ala Glu Asp Thr Gly Ile Tyr
            85                  90                  95

Tyr Cys Thr Arg Arg Asn Gly Pro Ser Ser Arg Ala Met Asp Tyr Trp
        100                 105                 110

Gly Gln Gly Thr Thr Val Thr Val Ser Ser
    115                 120

<210> SEQ ID NO 93
<211> LENGTH: 111
<212> TYPE: PRT
<213> ORGANISM: Artificial Sequence
<220> FEATURE:
<223> OTHER INFORMATION: ScFv-58F VL

<400> SEQUENCE: 93
```

```
Asp Ile Leu Met Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
                20                  25                  30

Tyr Leu His Trp Tyr Gln Gln Lys Ser Gly Ala Ser Pro Lys Leu Trp
            35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Trp Thr Ser Gly Gly Gly Thr Lys Leu Glu Ile Lys Arg Ser Gly
            100                 105                 110
```

<210> SEQ ID NO 94
<211> LENGTH: 15
<212> TYPE: PRT
<213> ORGANISM: Artificial Sequence
<220> FEATURE:
<223> OTHER INFORMATION: linker

<400> SEQUENCE: 94

```
Gly Gly Gly Gly Ser Gly Gly Gly Gly Ser Gly Gly Gly Gly Ser
1               5                   10                  15
```

<210> SEQ ID NO 95
<211> LENGTH: 45
<212> TYPE: DNA
<213> ORGANISM: Artificial Sequence
<220> FEATURE:
<223> OTHER INFORMATION: linker nuclotide sequence

<400> SEQUENCE: 95

```
ggtggaggcg gttcaggcgg aggtggctct ggcggtggcg gatcg            45
```

<210> SEQ ID NO 96
<211> LENGTH: 18
<212> TYPE: PRT
<213> ORGANISM: Artificial Sequence
<220> FEATURE:
<223> OTHER INFORMATION: linker

<400> SEQUENCE: 96

```
Gly Ser Thr Ser Gly Ser Gly Lys Pro Gly Ser Gly Glu Gly Ser Ser
1               5                   10                  15

Ser Thr
```

<210> SEQ ID NO 97
<211> LENGTH: 351
<212> TYPE: DNA
<213> ORGANISM: Artificial Sequence
<220> FEATURE:
<223> OTHER INFORMATION: VH-12A (VH-12X)

<400> SEQUENCE: 97

```
caggttcagc ttcagcagtc tggggcagag cttgtgaagc caggggcctc agtcaagttg      60
tcctgcacag cttctggctt caacattaaa gacacctata tgcactgggt gaagcagagg     120
cctgaacagg gcctgagtg gattggaagg attgatcctg cgaatggtaa tactaaatat     180 gaccccgaagt tccagggcaa ggccactata acagcagaca catcctccaa cacagcctac     240
```

```
ctgcagctca gcagcctgac atctgaggac actgccgtct attactgtgc tagtctacta      300
tggtggggcc aagggactct ggtcactgtc tctgcagcta gcgtttcgag c               351

<210> SEQ ID NO 98
<211> LENGTH: 372
<212> TYPE: DNA
<213> ORGANISM: Artificial Sequence
<220> FEATURE:
<223> OTHER INFORMATION: VH-112A

<400> SEQUENCE: 98
caggtccacg tgaagcagtc tggggctgag ctggtgaggc ctggggcctc agtgaagatt      60
tcctgcaagg cttttggcta caccttcaca aaccatcata taaactgggt gaagcagagg      120
cctggacagg gtctggaatg gattggatac attaatccta gcactggtta tactgagtac      180
aatcagaagt tcaaggacaa ggccacattg actgcagaca atcctccag cacagcctac       240 atgcaactga gcagcctgac atctgaggac tctgcagtct attactgtgc aagttactac      300
ggtagtagct atgctatgga ctactgggt caaggaacct cagtcaccgt ctcctcagct       360
agcgtttcga gc                                                         372

<210> SEQ ID NO 99
<211> LENGTH: 768
<212> TYPE: DNA
<213> ORGANISM: Artificial Sequence
<220> FEATURE:
<223> OTHER INFORMATION: ScFv-58F

<400> SEQUENCE: 99
gatattttga tgactcagtc tccagcaatc atgtctgcat ctccagggga aaaggtcacc      60
atgacctgca gggccagctc aagtgtaagt tccagttact gcactggta ccagcagaag       120 tcaggtgcct cccccaaact ctggatttat agcacatcca acttggcttc tggagtccct      180
gctcgcttca gtggcagtgg gtctgggacc tcttactctc tcacaatcag cagtgtggag      240
gctgaagatg ctgccactta ttactgccag cagtacagtg gttacccgtg gacgtccggt      300
ggaggcacca agctggaaat aaaacgttcc ggagggtcga ccagcggttc tgggaaacca     360
ggttccggtg aaggctcgag cagtaccgaa gtgaaagttg aggagtctgg aggaggcttg     420
gtgcaacctg gaggatccat gaaactctcc tgtgtcgcct ctggattcac tttcagtaac     480
tactggatga actgggtccg ccagtctcca gagaaggggc ttgagtgggt tgctgaaatt     540
agattgaaat ctaataatta tgcaacacat tatgcggagt ctgtgaaagg gaggttcacc     600
atctcaagag atgattccga aagtagtgtc tacctgcaaa tgaacaactt aagagctgaa     660
gacactggca tttattactg taccaggagg aatggaccct cctcccgggc tatggactac     720
tggggtcaag gaaccacggt caccgtctcc tcagctagcg tttcgagc                  768
```